(12) United States Patent
Strakhova et al.

(10) Patent No.: US 8,420,083 B2
(45) Date of Patent: Apr. 16, 2013

(54) ANTIBODIES TO RECEPTOR FOR ADVANCED GLYCATION END PRODUCTS (RAGE) AND USES THEREOF

(75) Inventors: Marina I. Strakhova, Vernon Hills, IL (US); Jill-Desiree Brederson, Evanston, IL (US)

(73) Assignee: Abbvie Inc., North Chicago, IL (US)

( * ) Notice: Subject to any disclaimer, the term of this patent is extended or adjusted under 35 U.S.C. 154(b) by 112 days.

(21) Appl. No.: 12/914,426

(22) Filed: Oct. 28, 2010

(65) Prior Publication Data
US 2011/0104174 A1 May 5, 2011

Related U.S. Application Data

(60) Provisional application No. 61/256,949, filed on Oct. 31, 2009.

(51) Int. Cl.
*A61K 39/395* (2006.01)
*C07K 16/18* (2006.01)
*C07K 16/28* (2006.01)

(52) U.S. Cl.
USPC ............... 424/130.1; 424/139.1; 424/141.1; 424/143.1; 530/387.1; 530/387.9; 530/388.1; 530/388.22

(58) Field of Classification Search .................. None
See application file for complete search history.

(56) References Cited

U.S. PATENT DOCUMENTS

| | | |
|---|---|---|
| 4,526,938 A | 7/1985 | Churchill et al. |
| 4,816,397 A | 3/1989 | Boss et al. |
| 4,816,567 A | 3/1989 | Cabilly et al. |
| 4,880,078 A | 11/1989 | Inoue et al. |
| 4,946,778 A | 8/1990 | Ladner et al. |
| 4,980,286 A | 12/1990 | Morgan et al. |
| 5,128,326 A | 7/1992 | Balazs et al. |
| 5,223,409 A | 6/1993 | Ladner et al. |
| 5,225,539 A | 7/1993 | Winter |
| 5,258,498 A | 11/1993 | Huston et al. |
| 5,290,540 A | 3/1994 | Prince et al. |
| 5,403,484 A | 4/1995 | Ladner et al. |
| 5,427,908 A | 6/1995 | Dower et al. |
| 5,516,637 A | 5/1996 | Huang et al. |
| 5,530,101 A | 6/1996 | Queen et al. |
| 5,565,332 A | 10/1996 | Hoogenboom et al. |
| 5,571,698 A | 11/1996 | Ladner et al. |
| 5,580,717 A | 12/1996 | Dower et al. |
| 5,585,089 A | 12/1996 | Queen et al. |
| 5,624,821 A | 4/1997 | Winter et al. |
| 5,627,052 A | 5/1997 | Schrader |
| 5,648,260 A | 7/1997 | Winter et al. |
| 5,658,727 A | 8/1997 | Barbas et al. |
| 5,679,377 A | 10/1997 | Bernstein et al. |
| 5,693,762 A | 12/1997 | Queen et al. |
| 5,698,426 A | 12/1997 | Huse |
| 5,714,350 A | 2/1998 | Co et al. |
| 5,714,352 A | 2/1998 | Jakobovits |
| 5,723,323 A | 3/1998 | Kauffman et al. |
| 5,733,743 A | 3/1998 | Johnson et al. |
| 5,750,753 A | 5/1998 | Kimae et al. |
| 5,763,192 A | 6/1998 | Kauffman et al. |
| 5,766,886 A | 6/1998 | Studnicka et al. |
| 5,780,225 A | 7/1998 | Wigler et al. |
| 5,807,715 A | 9/1998 | Morrison et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,855,913 A | 1/1999 | Hanes et al. |
| 5,874,064 A | 2/1999 | Edwards et al. |
| 5,912,015 A | 6/1999 | Bernstein et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,994,619 A | 11/1999 | Stice et al. |
| 5,998,209 A | 12/1999 | Jokobovits et al. |
| 6,019,968 A | 2/2000 | Platz et al. |
| 6,075,181 A | 6/2000 | Kucherlapati et al. |
| 6,091,001 A | 7/2000 | Jakobovits et al. |

(Continued)

FOREIGN PATENT DOCUMENTS

| | | |
|---|---|---|
| EP | 229246 B1 | 8/1993 |
| EP | 592106 A1 | 4/1994 |

(Continued)

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*

(Continued)

*Primary Examiner* — Christine J Saoud
*Assistant Examiner* — Jon M Lockard
(74) *Attorney, Agent, or Firm* — McAndrews, Held & Malloy Ltd.

(57) ABSTRACT

The present application relates to antibodies, such as monoclonal antibodies, and in particular CDR grafted, humanized versions thereof, for the treatment and diagnosis of pain and other neuroinflammatory conditions associated with the Receptor for Advanced Glycation End Products (RAGE).

12 Claims, 12 Drawing Sheets

U.S. PATENT DOCUMENTS

| | | | |
|---|---|---|---|
| 6,114,598 | A | 9/2000 | Kucherlapati et al. |
| 6,130,364 | A | 10/2000 | Jakobovits et al. |
| 6,180,370 | B1 | 1/2001 | Queen et al. |
| 6,204,023 | B1 | 3/2001 | Robinson et al. |
| 6,350,861 | B1 | 2/2002 | Co et al. |
| 6,660,843 | B1 | 12/2003 | Feige et al. |
| 6,699,658 | B1 | 3/2004 | Wittrup et al. |
| 7,612,181 | B2 | 11/2009 | Wu et al. |
| 2002/0137134 | A1 | 9/2002 | Gerngross |
| 2003/0185827 | A1 | 10/2003 | Rodriguez et al. |
| 2003/0186374 | A1 | 10/2003 | Hufton et al. |
| 2004/0018590 | A1 | 1/2004 | Gerngross et al. |
| 2004/0053865 | A1 | 3/2004 | Hart et al. |
| 2005/0042664 | A1 | 2/2005 | Wu et al. |
| 2005/0108791 | A1 | 5/2005 | Edgerton |
| 2006/0104968 | A1 | 5/2006 | Bookbinder et al. |
| 2007/0286858 | A1 | 12/2007 | Clancy et al. |
| 2009/0010934 | A1 | 1/2009 | Deckmyn et al. |
| 2010/0028359 | A1 | 2/2010 | Gu et al. |

FOREIGN PATENT DOCUMENTS

| | | | |
|---|---|---|---|
| EP | 239400 | B1 | 8/1994 |
| EP | 1176195 | A1 | 1/2002 |
| EP | 519596 | B1 | 2/2005 |
| WO | WO9002809 | A1 | 3/1990 |
| WO | WO9005144 | A1 | 5/1990 |
| WO | WO9014424 | A1 | 11/1990 |
| WO | WO9014430 | A1 | 11/1990 |
| WO | WO9014443 | A1 | 11/1990 |
| WO | WO9105548 | A1 | 5/1991 |
| WO | WO9109967 | A1 | 7/1991 |
| WO | WO9110737 | A1 | 7/1991 |
| WO | WO9110741 | A1 | 7/1991 |
| WO | WO9117271 | A1 | 11/1991 |
| WO | WO9201047 | A1 | 1/1992 |
| WO | WO9202551 | A1 | 2/1992 |
| WO | WO9203461 | A1 | 3/1992 |
| WO | WO9209690 | A2 | 6/1992 |
| WO | WO9211272 | A1 | 7/1992 |
| WO | WO9215679 | A1 | 9/1992 |
| WO | WO9218619 | A1 | 10/1992 |
| WO | WO9219244 | A2 | 11/1992 |
| WO | WO9220791 | A1 | 11/1992 |
| WO | WO9222324 | A1 | 12/1992 |
| WO | WO9301288 | A1 | 1/1993 |
| WO | WO9306213 | A1 | 4/1993 |
| WO | WO9311236 | A1 | 6/1993 |
| WO | WO9402602 | A1 | 2/1994 |
| WO | WO9418219 | A1 | 8/1994 |
| WO | WO9515982 | A2 | 6/1995 |
| WO | WO9520401 | A1 | 8/1995 |
| WO | WO9620698 | A2 | 7/1996 |
| WO | WO9633735 | A1 | 10/1996 |
| WO | WO9634096 | A1 | 10/1996 |
| WO | WO9720032 | A1 | 6/1997 |
| WO | WO9729131 | A1 | 8/1997 |
| WO | WO9732572 | A2 | 9/1997 |
| WO | WO9744013 | A1 | 11/1997 |
| WO | WO9816654 | A1 | 4/1998 |
| WO | WO9824893 | A2 | 6/1998 |
| WO | WO9831346 | A1 | 7/1998 |
| WO | WO9831700 | A1 | 7/1998 |
| WO | WO9850433 | A2 | 11/1998 |
| WO | WO9906834 | A2 | 2/1999 |
| WO | WO9915154 | A1 | 4/1999 |
| WO | WO9920253 | A1 | 4/1999 |
| WO | WO9925044 | A1 | 5/1999 |
| WO | WO9945031 | A2 | 9/1999 |
| WO | WO9953049 | A1 | 10/1999 |
| WO | WO9954342 | A1 | 10/1999 |
| WO | WO9966903 | A2 | 12/1999 |
| WO | WO0009560 | A2 | 2/2000 |
| WO | WO0037504 | A2 | 6/2000 |
| WO | WO0056772 | A1 | 9/2000 |
| WO | WO0183525 | A2 | 11/2001 |
| WO | WO02072636 | A2 | 9/2002 |
| WO | WO03016466 | A2 | 2/2003 |
| WO | WO03035835 | A2 | 5/2003 |
| WO | WO2004078140 | A2 | 9/2004 |
| WO | WO2005100584 | A2 | 10/2005 |
| WO | WO2007062852 | A2 | 6/2007 |
| WO | WO2007109749 | A2 | 9/2007 |
| WO | WO2008082651 | A2 | 7/2008 |
| WO | WO2008150949 | A1 | 12/2008 |
| WO | WO2009136382 | A2 | 11/2009 |

OTHER PUBLICATIONS

Abe R., et al., "Regulation of Human Melanoma growth and Metastasis by AGE-AGE Receptor Interactions," Journal of Investigative Dermatology, 2004, vol. 122 (2), pp. 461-467.

Ahmed K.A., et al., "Role of N-(carboxymethyl)lysine in the Development of Ischemic Heart Disease in type 2 Diabetes Mellitus," Journal of Clinical Biochemistry and Nutrition, 2007, vol. 41 (2), pp. 97-105.

Ames R.S., et al., "Conversion of Murine Fabs Isolated from a Combinatorial Phage Display Library to Full Length Immunoglobulins," Journal of Immunological Methods, 1995, vol. 184, pp. 177-186.

Arancio O., et al., "RAGE Potentiates Abeta-Induced Perturbation of Neuronal function in Transgenic Mice," EMBO Journal, 2004, vol. 23 (20), pp. 4096-4105.

Ausubel, et al., Current Protocols in Molecular Biology, 1993, Table of Contents.

Azzazy H.M., et al., "Phage Display Technology: Clinical Applications and Recent Innovations," Clinical Biochemistry, 2002, vol. 35 (6), pp. 425-445.

Babcook J.S., et al., "A Novel Strategy for Generating Monoclonal Antibodies from Single, Isolated lymphocytes Producing Antibodies of Defined Specificities," Proceedings of the National Academy of Sciences, 1996, vol. 93, pp. 7843-7848.

Barbas C.F., et al., "Assembly of Combinatorial Antibody Libraries on Phage Surfaces: The Gene III Site," The Proceedings of the National Academy of Sciences of the United States of America, 1991, vol. 88, pp. 7978-7982.

Barghorn S., et al., "Globular Amyloid [beta7-peptidel-42 oligomer—A Homogenous and Stable Neuropathological Protein in Alzheimer's Disease.," Journal of Neurochemistry, 2005, vol. 95 (3), pp. 834-847.

Baynes J.W., "Role of Oxidative Stress in Development of Complications in Diabetes," Diabetes, 1991, vol. 40 (4), pp. 405-412.

Bennett G.J., et al., "A Peripheral Mononeuropathy in Rat that Produces Disorders of Pain Sensation like those Seen in Man," Pain, 1988, vol. 33 (1), pp. 87-107.

Better M., et al., "*Escherichia coli* Secretion of an Active Chimeric Antibody Fragment," Science, 1988, vol. 240, pp. 1041-1043.

Bierhaus A., et al., "Loss of Pain Perception in Diabetes is Dependent on a Receptor of the Immunoglobulin Superfamily," The Journal of Clinical Investigation, 2004, vol. 114 (12), pp. 1741-1751.

Bird R.E., et al., "Single-Chain Antigen Binding Proteins," Science, 1988, vol. 242 (4877), pp. 423-426.

Boussac M., et al., "Calcium-Dependent Secretion in Human Neutrophils: A Proteomic Approach," Electrophoresis, 2000, vol. 21 (3), pp. 665-672.

Brinkmann U., et al., "Phage Display of Disulfide-stabilized Fv Fragments," Journal of Immunological Methods, 1995, vol. 182, pp. 41-50.

Buchwald H., et al., "Long-term, Continuous Intravenous Heparin Administration by an Implantable Infusion Pump in Ambulatory Patients with Recurrent Venous Thrombosis," Surgery, 1980, vol. 88, pp. 507-516.

Burton D.R., et al., "Human Antibodies from Combinatorial Libraries," Advances in Immunology, 1994, vol. 57, pp. 191-280.

Carter P., et al., "Humanization of an Anti-p185 HER2 Antibody for Human Cancer Therapy," Proceedings of the National Academy of Sciences of the United States of America, 1992, vol. 89, pp. 4285-4289.

Chavakis T., et al., "The Pattern Recognition Receptor (Rage) is a Counterreceptor for Leukocyte Integrins: A Novel Pathway for Inflammatory Cell Recruitment," The Journal of Experimental Medicine, 2003, vol. 198 (10), pp. 1507-1515.

Chothia C., et al., "Canonical Structures for the Hypervariable Regions of Immunoglobulins," Journal of Molecular Biology, 1987, vol. 196 (4), pp. 901-917.

Chothia C., et al., "Conformations of Immunoglobulin Hypervariable Regions," Nature, 1989, vol. 342 (6252), pp. 877-883.

Chothia C., et al., "Structural Repertoire of the Human VH Segments," Journal of Molecular Biology, 1992, vol. 227 (3), pp. 799-817.

Clackson T., et al., "Making Antibody Fragments Using Phage Display Libraries," Nature, 1991, vol. 352 (6336), pp. 624-628.

Cleek R.L., et al., "Biodegradable Polymeric Carriers for a bFGF Antibody for Cardiovascular Application," Proc. Intl. Symp. Control. Rel. Bioact. Mater., 1997, vol. 24, pp. 853-854.

Co M.S., et al., "Genetically Engineered Deglycosylation of the Variable Domain Increases the Affinity of an Anti-CD33 Monoclonal Antibody," Molecular Immunology, 1993, vol. 30 (15), pp. 1361-1367.

Deane R., et al., "RAGE Mediates Amyloid-beta Peptide Transport Across the Blood-brain Barrier and Accumulation in Brain," Nature Medicine, 2003, vol. 9 (7), pp. 907-913.

Devriese A. S., et al., "Inhibition of the Interaction of AGE-RAGE prevents Hyperglycemia-Induced fibrosis of the Peritoneal Membrane," Journal of the American Society of Nephrology, 2003, vol. 14 (8), pp. 2109-2118.

Donato R., "S100: A Multigenic Family of Calcium-Modulated Proteins of the Ef-Hand Type with Intracellular and Extracellular Functional Roles," The International Journal of Biochemistry & Cell Biology, 2001, vol. 33 (7), pp. 637-668.

Drinda S., et al., "Identification of the Receptor for Advanced Glycation end Products in Synovial tissue of Patients with Rheumatoid Arthritis," Rheumatology International, 2005, vol. 25 (6), pp. 411-413.

During M. J., et al., "Controlled Release of Dopamine from a Polymeric Brain Implant: In Vivo Characterization," Annals of Neurology, 1989, vol. 25 (4), pp. 351-356.

Fanger M.W., et al., "Production and Use of Anti-FcR Bispecific Antibodies," Immunomethods, 1994, vol. 4 (1), pp. 72-81.

Flyvbjerg A., et al., "Long-term Renal effects of a Neutralizing RAGE Antibody in Obese type 2 Diabetic Mice," Diabetes, 2004, vol. 53 (1), pp. 166-172.

Foell D., et al., "Expression of the Pro-Inflammatory Protein S100A12 (EN-RAGE) in Rheumatoid and Psoriatic Arthritis," Rheumatology, 2003, vol. 42 (11), pp. 1383-1389.

Foell D., et al., "Neutrophil derived human S100A12 (EN-RAGE) is strongly expressed during chronic active inflammatory bowel disease," Gut, 2003, 52 (6), 847-853.

Foell D., et al., "S100A12 (EN-RAGE) in Monitoring Kawasaki Disease," Lancet, 2003, vol. 361 (9365), pp. 1270-1272.

Foote J., et al., "Antibody Framework Residues Affecting the Conformation of the Hypervariable Loops," Journal of Molecular Biology, 1992, vol. 224 (2), pp. 487-499.

Fuchs P., et al., "Targeting Recombinant Antibodies to the Surface of Escherichia coli: Fusion to a Peptidoglycan Associated Lipoprotein," BioTechnology, 1991, vol. 9 (12), pp. 1369-1372.

Garrard L.J., et al., "Fab Assembly and Enrichment in a Monovalent Phage Display System," BioTechnology, 1991, vol. 9 (12), pp. 1373-1377.

Gavilondo J.V., et al., "Antibody Engineering at the Millennium," Biotechniques, 2000, vol. 29 (1), pp. 128-145.

Giege R., et al., "An introduction to the crystallogenesis of biological macromolecules,": Crystallization of Nucleic Acids and Proteins, 2nd Edition, Ducruix A., et al., eds., Oxford University Press, 1999, 18 pages.

Gillies S.D., et al., "High-Level Expression of Chimeric Antibodies Using Adapted cDNA Variable Region Cassettes," Journal of Immunological Methods, 1989, vol. 125 (1-2), pp. 191-202.

Goldspiel B.R., et al., "Human Gene therapy," Clinical Pharmacy, 1993, vol. 12 (7), pp. 488-505.

Goodson, "Medical Applications of Controlled Release," Langer and Wise, Eds., 1984, 2, 115-138.

Gram H., et al., "In Vitro Selection and Affinity Maturation of Antibodies from a Naïve Combinatorial Immunoglobulin Library," Proceedings of the National Academy of Sciences, 1992, vol. 89 (8), pp. 3576-3580.

Green L. L., et al., "Regulation of B Cell Development by Variable Gene Complexity in Mice Reconstituted with Human Immunoglobulin Yeast Artificial Chromosomes," Journal of Experimental Medicine, 1998, vol. 188 (3), pp. 483-495.

Green L.L., et al., "Antigen-Specific Human Monoclonal Antibodies from Mice Engineered with Human Ig Heavy and Light Chain YACs," Nature Genetics, 1994, vol. 7 (1), pp. 13-21.

Griffiths A.D., et al., "Human Anti-Self Antibodies with High Specificity from Phage Display Libraries," European Molecular Biology Organization, 1993, vol. 12 (2), pp. 725-734.

Hammerling G.J., et al., "Monoclonal Antibodies and T-Cell Hybridomas" 1981, pp. 563-681.

Harlow E., et al., "Antibodies: A Laboratory Manual", Cold Spring Harbor Laboratory, 1988, Table of Contents.

Haslbeck K.M., et al., "The Age/Rage/Nf-(Kappa)B Pathway May Contribute to the Pathogenesis of Polyneuropathy in Impaired Glucose Tolerance (IGT)," Experimental and Clinical Endocrinology & Diabetes, 2005, vol. 113 (5), pp. 288-291.

Hawkins R.E., et al., "Selection of Phage Antibodies by Binding Affinity Mimicking Affinity Maturation," Journal of Molecular Biology, 1992, vol. 226 (3), pp. 889-896.

Hay B.N., et al., "Bacteriophage Cloning and Escherichia coli Expression of a Human IgM Fab," Human Antibodies and Hybridomas, 1992, vol. 3 (2), pp. 81-85.

Hein G., et al., "Are Advanced Glycation End-Product-Modified Proteins of Pathogenetic Importance in Fibromyalgia?," Rheumatology, 2002, vol. 41 (10), pp. 1163-1167.

Hofmann M.A., et al., "RAGE Mediates a Novel Proinflammatory Axis: A Central Cell Surface Receptor for S100/Calgranulin Polypeptides," Cell, 1999, vol. 97, pp. 889-901.

Holliger P., et al., ""Diabodies": Small Bivalent and Bispecific Antibody Fragments," Proceedings of the National Academy of Sciences of the USA, 1993, vol. 90 (14), pp. 6444-6448.

Hoogenboom H.R., et al., "Designing and Optimizing Library Selection Strategies for Generating High-Affinity Antibodies," Trends in Biotechnology, 1997, vol. 15 (2), pp. 62-70.

Hoogenboom H.R., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.

Hoogenboom H.R., et al., "Natural and Designer Binding Sites Made by Phage Display Technology," Immunology Today, 2000, vol. 21 (8), pp. 371-378.

Howard M.A., et al., "Intracerebral Drug Delivery in Rats with Lesion-Induced Memory Deficits," Journal of Neurosurgery, 1989, vol. 71 (1), pp. 105-112.

Huang C.Y., et al., "COX-2 and iNOS are Critical in Advanced Glycation End Product-activated Chondrocytes in Vitro," European Journal of Clinical Investigation, 2009, vol. 39 (5), pp. 417-428.

Hudson B.I., et al., "Identification, Classification, and Expression of Rage Gene Splice Variants," FASEB Journal, 2008, vol. 22 (5), pp. 1572-1580.

Hurty C.A., et al., "Evaluation of the Tissue Reactions in the Skin and Body Wall of Koi (Cyprinus carpio) to Five Suture Materials," Veterinary Record, 2002, vol. 151 (11), pp. 324-328.

Huse W.D., et al., "Generation of a Large Combinatorial Library of the Immunoglobulin Repertoire in Phage Lambda," Science, 1989, vol. 246 (4935), pp. 1275-1281.

Huston J.S., et al., "Protein Engineering of Antibody Binding Sites: Recovery of Specific Activity in an Anti-Digoxin Single-Chain Fv Analogue Produced in Escherichia coli," Proceedings of the National Academy of Sciences of the USA, 1988, vol. 85 (16), pp. 5879-5883.

Huston J.S., et al., "Protein Engineering of Single-Chain Fv Analogs and Fusion Proteins," Methods in Enzymology, 1991, vol. 203, pp. 46-88.

Jefferis R., "Glycosylation of Recombinant Antibody Therapeutics," Biotechnology Program, 2005, vol. 21 (1), pp. 11-16.

Jensen I.J., et al., "Renal effects of a Neutralising RAGE-Antibody in Long-term Streptozotocin-Diabetic Mice," Journal of Endocrinology, 2006, vol. 188 (3), pp. 493-501.

Johnsson B., et al., "Comparison of Methods for Immobilization to Carboxymethyl Dextran Sensor Surfaces by Analysis of the Specific Activity of Monoclonal Antibodies," Journal of Molecular Recognition, 1995, vol. 8 (1-2), pp. 125-131.

Johnsson B., et al., "Immobilization of Proteins to a Carboxymethyldextran-Modified Gold Surface for Biospecific Interaction Analysis in Surface Plasmon Resonance Sensors," Analytical Biochemistry, 1991, vol. 198 (2), pp. 268-277.

Joliot A., et al., "Antennapedia Homeobox Peptide Regulates Neural Morphogenesis," Proceedings of the National Academy of Sciences, 1991, vol. 88 (5), pp. 1864-1868.

Jones P.T., et al., "Replacing the Complementarity-Determining Regions in a Human Antibody with those from a Mouse," Nature, 1986, vol. 321 (6069), pp. 522-525.

Jonsson U., et al., "Introducing a Biosensor Based Technology for Real-Time Biospecific Interaction Analysis," Annales de Biologie Clinique, 1993, vol. 51 (1), pp. 19-26.

Jonsson U., et al., "Real-Time Biospecific Interaction Analysis Using Surface Plasmon Resonance and a Sensor Chip Technology," Biotechniques, 1991, vol. 11 (5), pp. 620-627.

Kabat E.A., et al., "Attempts to Locate Complementarity-Determining Residues in the variable Positions of Light and Heavy Chains," Annals New York Academy of Sciences, 1971, vol. 190, pp. 382-393.

Kabat E.A., et al., ed., "Sequences of Proteins of Immunological Interest," 1991, 5 th Edition, Table of Contents.

Kabat E.A., et al., Sequences of Proteins of Immunological Interest, 1987, Table of Contents.

Kabat., "Sequences of Proteins of Immunological Interest," 1983, Table of Contents.

Kaufman R.J., et al., "Amplification and Expression of Sequences Cotransfected with a Modular Dihydrofolate Reductase Complementary DNA Gene," Journal of Molecular Biology, 1982, vol. 159 (4), pp. 601-621.

Kawakami M., et al., "Experimental Lumbar Radiculopathy. Immunohistochemical and Quantitative Demonstrations of Pain Induced by Lumbar Nerve Root Irritation of the Rat," Spine, 1994, vol. 19 (16), pp. 1780-1794.

Kellermann S.A., et al., "Antibody Discovery: The Use of Transgenic Mice to Generate Human Monoclonal Antibodies for Therapeutics," Current Opinion in Biotechnology, 2002, vol. 13 (6), pp. 593-597.

Kettleborough C.A., et al., "Isolation of Tumor Cell-specific Single-chain Fv from Immunized Mice using Phage-antibody Libraries and the Re-construction of Whole Antibodies from these Antibody Fragments," European Journal of Immunology, 1994, vol. 24 (4), pp. 952-958.

Kipriyanov S.M., et al., "Recombinant Single-Chain Fv Fragments Carrying C-Terminal Cysteine Residues: Production of Bivlent and Biotinylated Miniantibodies," Molecular Immunology, 1994, vol. 31 (14), pp. 1047-1058.

Kipriyanov S.M., et al., "Single-Chain Antibody Streptavidin Fusions: Tetrameric Bifunctional scFv-Complexes with Biotin Binding Activity and Enhanced Affinity to Antigen," Human Antibodies and Hybridomas, 1995, vol. 6 (3), pp. 93-101.

Kohler G., et al., "Continuous Cultures of Fused Cells Secreting Antibody of Predefined Specificity," Nature, 1975, vol. 256 (5517), pp. 495-497.

Kokkola R., et al., "High Mobility Group Box Chromosomal Protein 1: A Novel Proinflammatory Mediator in Synovitis," Arthritis & Rheumatism, 2002, vol. 46 (10), pp. 2598-2603.

Kontermann R., et al., eds., Antibody Engineering, Springer-Verlag Berlin Heidelberg, 2001, Table of Contents.

Kriegler M., Gene Transfer and Expression: A Laboratory Manual, Stockton Press, 1990, Table of Contents.

Lam X.M., et al., "Microencapsulation of Recombinant Humanized Monoclonal Antibody for Local Delivery," Proceedings of the 24th International Symposium on Controlled Release of Bioactive Materials, 1997, vol. 24, pp. 759-760.

Langer R., et al., "Chemical and Physical Structure of Polymers as Carriers for Controlled Rlease of Bioactive Agents: A Review," Journal of Macromolecular Science—Reviews in Macromolecular Chemistry & Physics, 1983, vol. C23 (1), pp. 61-126.

Langer R., "New Methods of Drug Delivery," Science, 1990, vol. 249 (4976), pp. 1527-1533.

Leclerc E., et al., "Binding of S100 Proteins to Rage: An Update," Biochimica et Biophysica Acta, 2009, vol. 1793 (6), pp. 993-1007.

Leclerc E., et al., "S100B and S100A6 differentially Modulate Cell Survival by Interacting with Distinct RAGE (receptor for advanced glycation end products) Immunoglobulin Domains," Journal of Biological Chemistry, 2007, vol. 282 (43), pp. 31317-31331.

Levy R.D., et al., "Inhibition of Calcification of Bioprosthetic Heart Valves by Local Controlled-Release Diphosphonate," Science, 1985, vol. 228 (4696), pp. 190-192.

Liliensiek B., et al., "Receptor for Advanced Glycation end Products (RAGE) Regulates Sepsis but not the Adaptive Immune Response," Journal of Clinical Investigation, 2004, vol. 113 (11), pp. 1641-1650.

Little M., et al., "Of Mice and Men: Hybridoma and Recombinant Antibodies," Immunology Today, 2000, vol. 21 (8), pp. 364-370.

MacCallum R.M., et al., "Antibody-Antigen Interactions: Contact Analysis and Binding Site Topography," The Journal of Molecular Biology, 1996, vol. 262, pp. 732-745.

Marchalonis J.J., et al., "Evolutionary Factors in the Emergence of the Combinatorial Germline Antibody Repertoire," Advances in Experimental Medicine and Biology, 2001, vol. 484, pp. 13-30.

McCafferty J., et al., "Phage Antibodies: Filamentous Phage Displaying Antibody Variable Domains," Nature, 1990, vol. 348, pp. 552-554.

Mendez M.J., et al., "Functional Transplant of Megabase Human Immunoglobulin Loci Recapitulates Human Antibody Response in Mice," Nature Genetics, 1997, vol. 15 (2), pp. 146-156.

Misur I., et al., "Advanced Glycation Endproducts in Peripheral Nerve in Type 2 Diabetes with Neuropathy," Acta Diabetol, 2004, vol. 41 (4), pp. 158-166.

Mizushima S., et al., "pEF-BOS, a Powerful Mammalian Expression Vector," Nucleic Acids Research, 1990, vol. 18 (17), pp. 5322.

Morgan R.A., et al., "Human Gene Therapy," Annual Review of Biochemistry, 1993, vol. 62, 191-217.

Morrison S.L., et al., "Chimeric Human Antibody Molecules: Mouse Antigen-Binding Domains with Human Constant Region Domains," Proceedings of National Academy of Sciences, 1984, vol. 81 (21), pp. 6851-6855.

Morrison S.L., "Transfectomas Provide Novel Chimeric Antibodies," Science, 1985, vol. 229 (4719), pp. 1202-1207.

Mulligan R.C., "The Basic Science of Gene Therapy," Science (New York, N.Y.), 1993, vol. 260 (5110), pp. 926-932.

Mullinax R.L., et al., "Expressoin of a Heterodimeric Fab Antibody Protein in One Cloning Step," Bio Techniques, 1992, vol. 12 (6), pp. 864-869.

Myint K., et al., "RAGE Control of Diabetic Nephropathy in a Mouse Model Effects of RAGE Gene Disruption and Administration of Low?Molecular Weight Heparin," Diabetes, 2006, vol. 55 (9), pp. 2510-2522.

Neuberger M.S., et al., "Recombinant Antibodies Possessing Novel Effector Functions," Nature, 1984, vol. 312 (5995), pp. 604-608.

Niederberger E., et al., "The IKK-NF-kappaB Pathway: A Source for Novel Molecular Drug Targets in Pain Therapy?," FASEB Journal, 2008, vol. 22 (10), pp. 3432-3442.

Ning S., et al., "Intratumoral Radioimmunotherapy of a Human Colon Cancer Xenograft Using a Sustained-Release Gel," Radiotherapy & Oncology: The Journal of the European Society for Therapeutic Radiology and Oncology, 1996, vol. 39 (2), pp. 179-189.

Oi V.T., et al., "Chimeric Antibodies," BioTechniques, 1986, vol. 4 (3), pp. 214-221.

Ostendorp T., et al., "Expression and Purification of the Soluble Isoform of Human Receptor for Advanced Glycation End Products (sRAGE) from *Pichia pastoris*," Biochemical and Biophysical Research Communications, 2006, vol. 347 (1), pp. 4-11.

Ostendorp T., et al., "Structural and Functional Insights into RAGE Activation by Multimeric S100B," EMBO Journal, 2007, vol. 26 (16), pp. 3868-3878.

Padlan E.A., "A Possible Procedure for Recucing the Immunogenicity of Antibody Variable Domains While Preserving Their Ligand-Binding Properties," Molecular Immunology, 1991, vol. 28 (4-5), pp. 489-498.

Padlan E.A., et al., "Identification of Specificity-Determining Residues in Antibodies," The FASEB Journal : Official Publication of the Federation of American Societies for Experimental Biology, 1995, vol. 9 (1), pp. 133-139.

Persic L., et al., "An Integrated Vector System for the Eukaryotic Expression of Antibodies or their Fragments After Selection from Phage Display Libraries," Gene, 1997, vol. 187 (1), pp. 9-18.

Poljak R.J., "Production and Structure of Diabodies," Structure, 1994, vol. 2 (12), pp. 1121-1123.

Presta L.G., et al., "Humanization of an Antibody Directed Against IgE," Journal of Immunology, 1993, vol. 151 (5), pp. 2623-2632.

Ramasamy R., et al., "Advanced Glycation End Products and Rage: A Common Thread in Aging, Diabetes, Neurodegeneration, and Inflammation," Glycobiology, 2005, vol. 15 (7), pp. 16R-28R.

Ramasamy R., et al., "Glycation and RAGE: Common Links in the Pathogenesis of Microvascular and Macrovascular Complications of Diabetes," Canadian Journal of Diabetes, 2006, vol. 30 (4), pp. 422-429.

Remington, "The Science and Practice of Pharmacy," Table of Contents, 1995.

Rhodin J., et al., "Animal Model of Amyloid-β Induced Vascular Inflammation and Prevention by Estrogen and Other Agents," 7th World Congress for Microcirculation, Sydney, Australia, Aug. 19-22, 2001, 543-547.

Riechmann L., et al., "Reshaping Human Antibodies for Therapy," Nature, 1988, vol. 332 (6162), pp. 323-327.

Roberts R.W., et al., "RNA-Peptide Fusions for the in Vitro Selection of Peptides and Proteins," PNAS USA, 1997, vol. 94(23), pp. 12297-12302.

Robinson, "Gene Therapy—Proceeding from Laboratory to Clinic," TIBTECH, 1993, 11 (5), 155-215.

Robinson J.R., Sustained and Controlled Release Drug Delivery Systems, Marcel Dekker, Inc., 1978, Table of Contents.

Roguska M.A., et al., "Humanization of Murine Monoclonal Antibodies through Variable Domain Resurfacing," Proceedings of the National Academy of Sciences, 1994, vol. 91 (3), pp. 969-973.

Ruster M., et al., "Detection of Elevated N Epsilon-Carboxymethyllysine Levels in Muscular Tissue and in Serum of Patients with Fibromyalgia," Journal of Rheumatology, 2005, vol. 34 (6), pp. 460-463.

Sambrook J., et al., eds., Molecular Cloning: A Laboratory Manual, 3rd Edition, Cold Spring Harbor Laboratory, 2001, Table of Contents.

Sambrook J., et al., "Expression of Cloned Genes in *Escherichia coli*," in: Molecular Cloning: A Laboratory Manual, Second Edition, TOC, Cold Spring Harbor Laboratory Press, 1989.

Sasaki N., et al., "Advanced Glycation end Products (AGE) and their Receptor (RAGE) in the Brain of Patients with Creutzfeldt-Jakob disease with Prion Plaques," Neuroscience Letters, 2002, vol. 326 (2), pp. 117-120.

Saudek C.D., et al., "A Preliminary Trial of the Programmable Implantable Medication System for Insulin Delivery," The New England Journal of Medicine, 1989, vol. 321 (9), pp. 574-579.

Sawai H., et al., "Direct Production of the Fab Fragment Derived from the Sperm Immobilizing Antibody using Polymerase Chain Reaction and Cdna Expression Vectors," American Journal of Reproductive Immunology, 1995, vol. 34 (1), pp. 26-34.

Schafer B.W., et al., "The S100 Family of Ef-Hand Calcium-Binding Proteins: Functions and Pathology," Trends in Biochemical Sciences, 1996, vol. 21 (4), pp. 134-140.

Schmidt A.M., et al., "Activation of Receptor for Advanced Glycation end Products: a Echanism for Chronic Vascular Dysfunction in Diabetic Vasculopathy and Atherosclerosis," Circulation Research, 1999, vol. 84 (5), pp. 489-497.

Schmidt A.M., et al., "The Multiligand Receptor RAGE as a Progression Factor Amplifying Immune and Inflammatory Responses," Journal of Clinical Investigation, 2001, vol. 108 (7), pp. 949-955.

Sefton M.V., et al., "Implantable Pumps," Critical Reviews in Biomedical Engineering, 1987, vol. 14 (3), pp. 201-240.

Shapiro G.S., et al., "DNA Target Motifs of Somatic Mutagenesis in Antibody Genes," Critical Reviews in Immunology, 2002, vol. 22 (3), pp. 183-200.

Shields R.L., et al., "Lack of Fucose on Human Igg1 N-Linked Oligosaccharide Improves Binding to Human Fc[Gamma]RIII and Antibody-Dependent Cellular toxicity," Journal of Biological Chemistry, 2002, vol. 277 (30), pp. 26733-26740.

Shu L., et al., "Secretion of a Single-Gene-Encoded Immunoglobulin from Myeloma Cells," Proceedings of the National Academy of Sciences USA, 1993, vol. 90 (17), pp. 7995-7999.

Sims M.J., et al., "A Humanized CD18 Antibody Can Block Function Without Cell Destruction," Journal of Immunology, 1993, vol. 151 (4), pp. 2296-2308.

Skerra A., et al., "Assembly of a Functional Immunoglobulin Fv Fragment in *Escherichia coli*," Science, 1988, vol. 240, pp. 1038-1041.

Smolen V.F., et al., eds., Controlled Drug Bioavailability: Drug Product Design and Performance, vol. 1, John Wiley & Sons, 1984, Table of Contents.

Song Y.K., et al., "Antibody Mediated Lung Targeting of Long-Circulating Emulsions," PDA Journal of Pharmaceutical Science and Technology, 1995, vol. 50 (6), pp. 372-397.

Studnicka G.M., et al., "Human-Engineered Monoclonal Antibodies Retain full Specific Binding Activity by Preserving Non-CDR Complementarity-Modulating Residues," Protein Engineering, 1994, vol. 7 (6), pp. 805-814.

Sugimoto K., et al., "Localization in Human Diabetic Peripheral Nerve of N(Epsilon)-Carboxymethyllysine-Protein Adducts, an Advanced Glycation Endproduct," Diabetologia, 1997, vol. 40 (12), pp. 1380-1387.

Sugimoto K., et al., "Role of Advanced Glycation End Products in Diabetic Neuropathy," Current Pharmaceutical Design, 2008, vol. 14 (10), pp. 953-961.

Takeda S., et al., "Construction of Chimaeric Processed Immunoglobulin Genes Containing Mouse Variable and Human Constant Region Sequences," Nature, 1985, vol. 314 (6010), pp. 452-454.

Tanga F.Y., et al., "Role of Astrocytic S100Beta in Behavioral Hypersensitivity in Rodent Models of Neuropathic Pain," Neuroscience, 2006, vol. 140 (3), pp. 1003-1010.

Tanji N., et al., "Expression of Advanced Glycation end Products and their Cellular Receptor RAGE in Diabetic Nephropathy and Nondiabetic Renal Disease," Journal of the American Society of Nephrology, 2000, vol. 11 (9), pp. 1656-1666.

Taylor L.D., et al., "A Transgenic Mouse that Expresses a Diversity of Human Sequence Heavy and Light Chain Immnoglobulins," Nucleic Acids Research, 1992, vol. 20 (23), 6287-6295.

Thornalley P.J., "Glycation in Diabetic Neuropathy: Characteristics, Consequences, Causes, and Therapeutic Options," International Review of Neurobiology, 2002, vol. 50, pp. 37-57.

Tolstoshev P., "Gene Therapy, Concepts, Current Trials and Future Directions," Annual Review of Pharmacology and Toxicology, 1993, vol. 32, pp. 573-596.

Toth C., et al., "RAGE, Diabetes, and the Nervous System," Current Molecular Medicine, 2007, vol. 7 (8), pp. 766-776.

Toth C., et al., "Receptor for Advanced Glycation End Products (RAGEs) and Experimental Diabetic Neuropathy," Diabetes, 2008, vol. 57 (4), pp. 1002-1017.

Umana P., et al., "Engineered Glycoforms of an Antineuroblastoma Igg1 with Optimized Antibody-Dependent Cellular Cytotoxic Activity," Nature Biotechnology, 1999, vol. 17 (2), pp. 176-180.

Urlaub G., et al., "Isolation of Chinese Hamster Cell Mutants Deficient in Dihydrofolate Reductase Activity," Proceedings of the National Academy of Sciences of the USA, 1980, vol. 77 (7), pp. 4216-4220.

Verhoeyen M., et al., "Reshaping Human Antibodies: Grafting an Antilysozyme Activity," Science, 1988, vol. 239, pp. 1534-1536.

Wallick S.C., et al., "Glycosylation of a VH Residue of a Monoclonal Antibody Against a(1-46) Dextran Increases Its Affinity for Antigen," The Journal of Experimental Medicine, 1988, vol. 168 (3), pp. 1099-1109.

Ward E.S., et al., "Binding Activities of a Repertoire of Single Immunoglobulin Variable Domains Secreted from *Escherichia coli*," Nature, 1989, vol. 341 (6242), pp. 544-546.

Weldon D.T., et al., "New insights into the Neuropathology and Cell Biology of Alzheimer's disease," Geriatrics, 1997, vol. 53 (2), pp. S13-S16.

Winnacker, et al., "From Genes to Clones, Introduction to Gene Technology," Verlagsgesellschaft, 1987, TOC.

Wright A., et al., "Antibody Variable Region Glycosylation: Position Effects on Antigen Binding and Carbohydrate Structure," The EMBO Journal, 1991, vol. 10 (10), pp. 2717-2723.

Wu G.Y., et al., "Delivery Systems for Gene Therapy," Biotherapy, 1991, vol. 3 (1), pp. 87-95.

Wu G.Y., et al., "Receptor-Mediated in Vitro Gene Transformation by a Soluble DNA Carrier System," The Journal of Biological Chemistry, 1987, vol. 262 (10), pp. 4429-4432.

Xie J., et al., "Hexameric Calgranulin C (S100A12) binds to the Receptor for Advanced Glycated end Products (RAGE) using Symmetric Hydrophobic Target-Binding Patches," Journal of Biological Chemistry, 2007, vol. 282 (6), pp. 4218-4231.

Yan S.D., et al., "Cellular Cofactors Potentiating Induction of Stress and Cytotoxicity by Amyloid Beta-Peptide," Biochimica et Biophysica Acta, 2000, vol. 1502 (1), pp. 145-157.

Yan S.D., et al., "What's the RAGE? The Receptor for Advanced Glycation end Products (RAGE) and the Dark side of Glucose.," European Journal of Clinical Investigation, 1997, vol. 27 (3), pp. 179-181.

Yan S.S., et al., "Suppression of Experimental Autoimmune Encephalomyelitis by Selective Blockade of Encephalitogenic T-cell Infiltration of the Central nervous System," Nature Medicine, 2003, vol. 9 (3), pp. 287-293.

Zimmer D.B., et al., "The S100 Protein Family: History, Function, and Expression," Brain Research Bulletin, 1995, vol. 37 (4), pp. 417-429.

\* cited by examiner

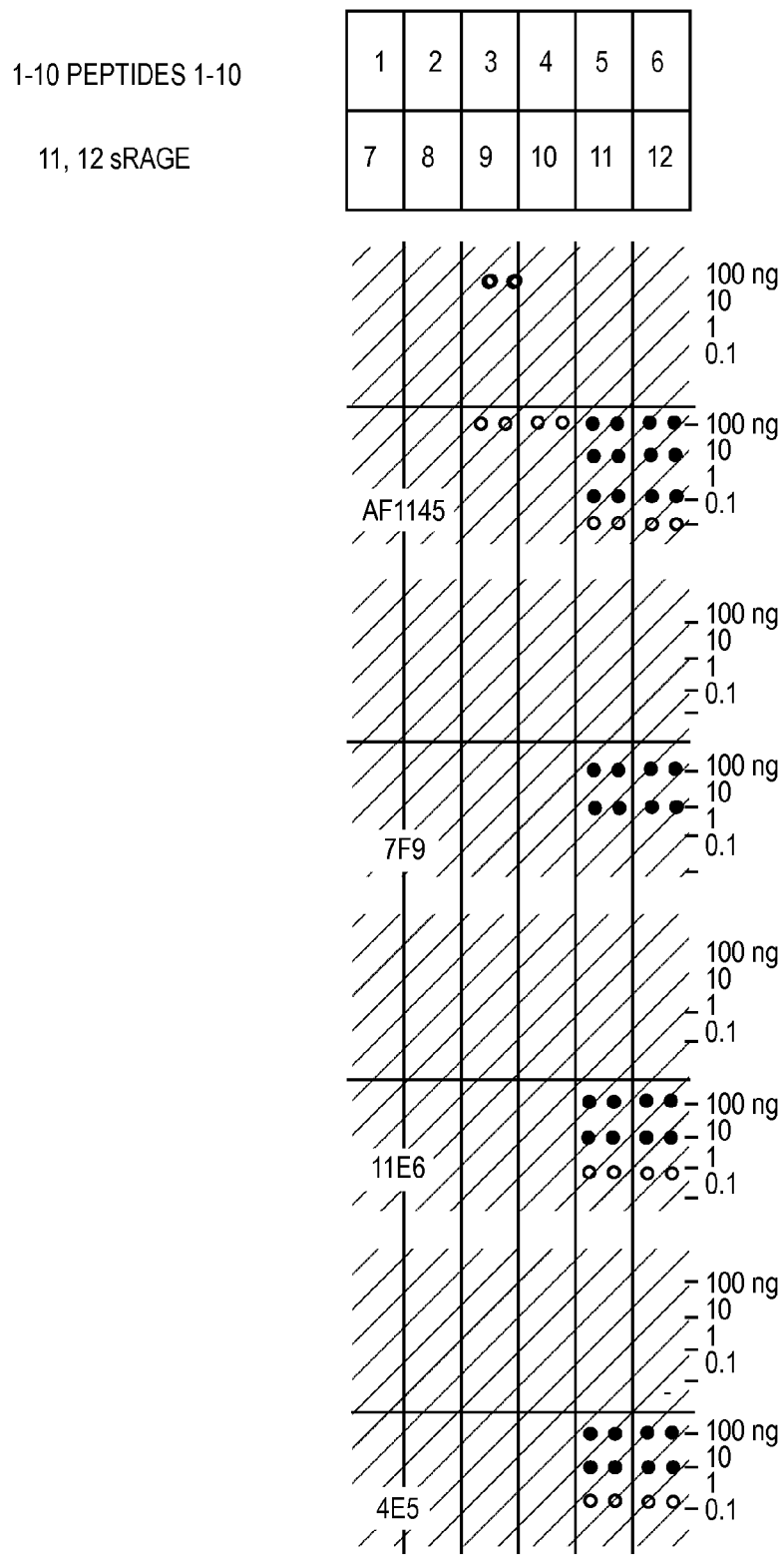

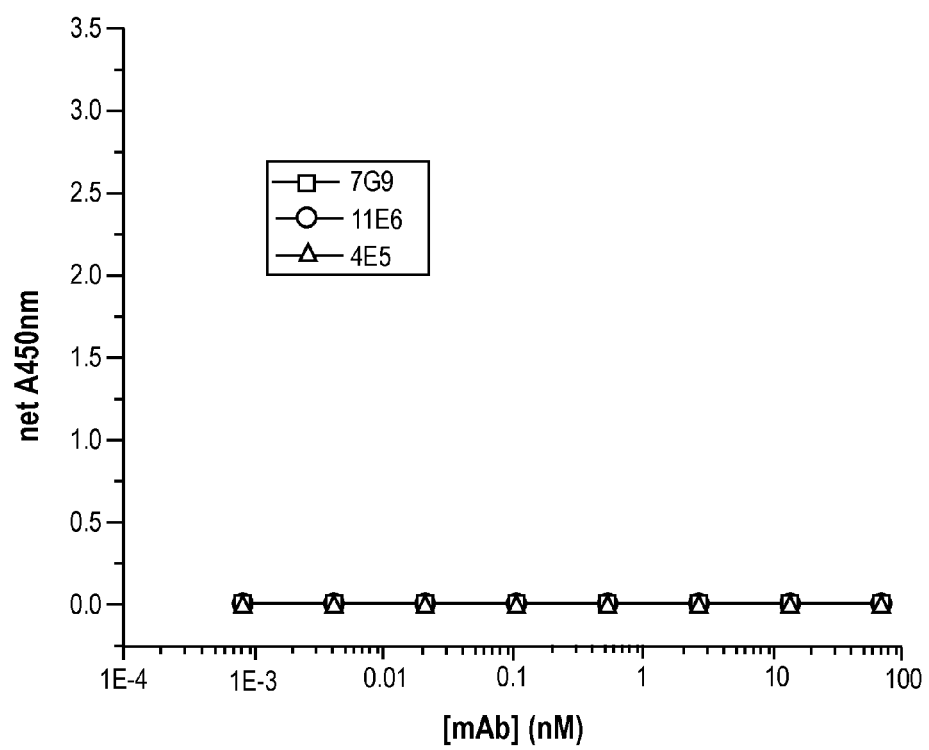

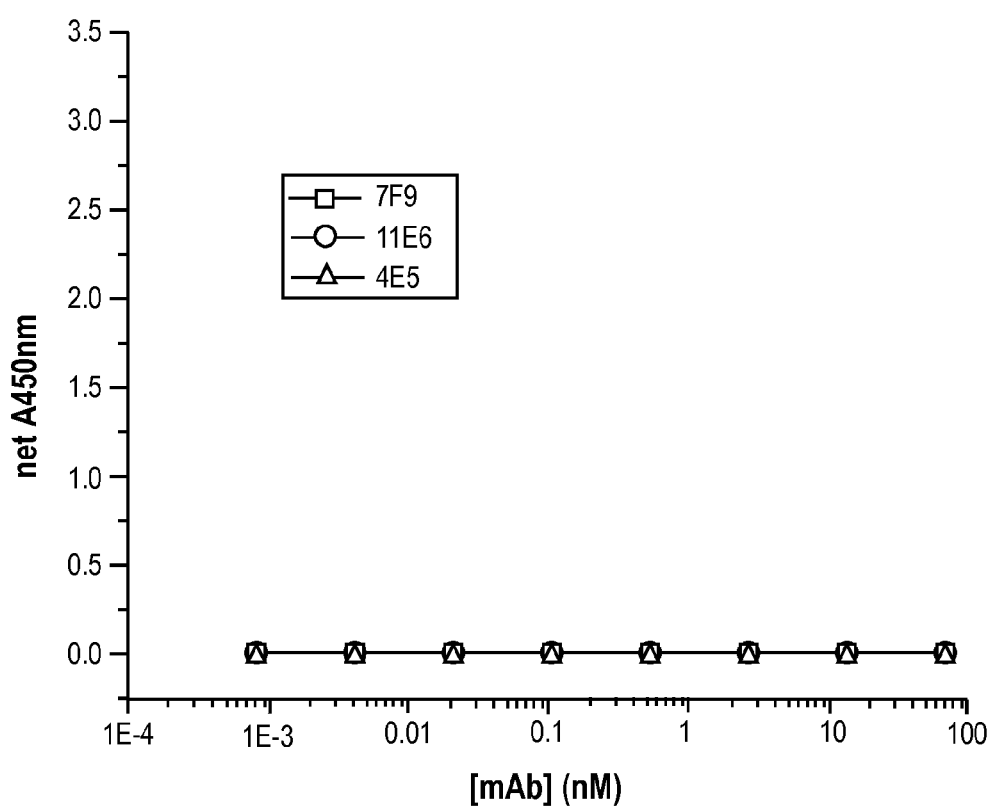

US 8,420,083 B2

ANTIBODIES TO RECEPTOR FOR ADVANCED GLYCATION END PRODUCTS (RAGE) AND USES THEREOF

RELATED APPLICATION INFORMATION

This application claims the benefit of U.S. Application No. 61/256,949 filed on Oct. 31, 2009, the contents of which are herein incorporated by reference.

TECHNICAL FIELD

The present application relates to antibodies, particularly monoclonal antibodies, and in particular CDR grafted, humanized versions thereof, for the treatment and diagnosis of pain and other neuroinflammatory conditions associated with the Receptor for Advanced Glycation End Products (RAGE).

BRIEF DESCRIPTION OF SEQUENCE LISTING

A sequence listing in accordance with 37 C.F.R. §§1.821-1.825 is attached to the present invention and contained in a file named "10216USO1.txt" (119 Kb, created Oct. 20, 2010) and is hereby incorporated herein by reference.

BACKGROUND INFORMATION

Chronic pathological pain remains an area of significant unmet medical need. Current treatments, such as duloxetine, are efficacious only in a limited subset of patients and are associated with dose-limiting side effects, such as nausea and somnolence. Advanced Glycation End products (AGEs) and one of their receptors (RAGE) have been implicated in the ethiology of chronic pain syndromes, including those of diabetic neuropathy and fibromyalgia.

The Receptor for Advanced Glycation Endproducts (RAGE) is a multi-ligand receptor of the immunoglobulin superfamily. Extracellular domain of RAGE includes one N-terminal V-type and two $C_2$-type immunoglobulin domains usually termed C1 and C2. Ligands of RAGE include AGEs (the products of nonenzymatic glycation and oxidation of proteins and lipids such as carboxymethyl lysine (CML) adducts), Aβ, S100/calgranulins and amphoterin. Different ligands have been shown to bind to different domains within RAGE. For example, S100b, HMGB1 and amyloid Aβ are reported to bind to the V-domain, as evidenced by various groups (Ostendorp et al. *EMBO J.* 2007; 26(16): 3868-3878; Leclerc E et al, *J Biol. Chem.* 2007; 282 (43): 31317-31331; WO 2007/109749 (A2). Ligands of C1 (first $C_2$-like) domain and C2 (second $C_2$-like) domain were reported to include S100A12 (also called ENRAGE or Calgranulin C) and Aβ in case of C1 (Hofmann M A et al. *Cell,* 1999; 97: 889-901), and S100A6 (Leclerc E et al, *J Biol. Chem.* 2007; 282 (43): 31317-31331). In some cases, the precise location of binding of a ligand to RAGE remains unclear.

SUMMARY OF THE INVENTION

The present invention provides a method of treatment of chronic pain using anti-RAGE antibodies; representative anti-RAGE antibodies of the invention may comprise at least one of the antibody variable region amino acid sequences shown in SEQ ID NOs: 9, 13, 17 and 21, or individual CDRs thereof or related CDR sequences, as specified in more detail below.

Included in the present invention are anti-RAGE antibodies that bind specifically to RAGE and comprise a light chain variable region having an amino acid sequence that is at least 90% identical to any of SEQ ID NOs: 13 and 21, or is a RAGE-binding fragment of an antibody comprised in said sequences.

Also included are anti-RAGE antibodies that bind specifically to RAGE and comprise a heavy chain variable region having an amino acid sequence that is at least 90% identical to any of SEQ ID NOs: 9 and 17, or is a RAGE-binding fragment of an antibody comprised in said sequences.

A particular embodiment of the present invention is represented by several monoclonal antibodies that are able to bind to the C-domain of RAGE, and to block the binding of Aβ-globulomers. More specifically the present invention describes monoclonal antibody 11E6, which binds to the C-2 domain of RAGE, does not bind to peptides with amino acid sequences used to generate polyclonal antibodies, and is able to neutralize in vivo the effect of Aβ1-40 on cerebral vasculature in mice.

The anti-RAGE antibodies of the invention include antibodies that bind specifically to the C-domain of RAGE.

The anti-RAGE antibodies of the invention include an anti-RAGE antibody or a RAGE-binding fragment as described above, which is selected from the group consisting of chimeric antibody, a CDR-grafted or humanized antibody, a single chain antibody, a fusion protein, and a human antibody.

In various embodiments, the antibodies of the invention are recombinant antibodies or monoclonal antibodies. Particular neutralizing antibodies of the present application are referred to herein as mAb7F9, mAb11E6, and mAb4E5 and functional antibody fragments thereof, and other antibodies and functional antibody fragments with equivalent properties to mAb7F9, mAb11E6, and mAb4E5, such as high affinity binding to RAGE with low dissociation kinetics and high neutralizing capacity, are intended as part of the present invention. The human antibodies of the present application, however, may include amino acid residues not encoded by human germline immunoglobulin immunogenic RAGE polypeptide or fragment thereof that may be determined by any method known in the art. For example, the binding affinity can be measured by competitive ELISAs, RIAs, BIAcore or KinExA technology. The dissociation rate also can be measured by BIAcore or KinExA technology. The binding affinity and dissociation rate are measured by surface plasmon resonance using, e.g., BIAcore.

One of the monoclonal antibodies of the present application, the mAb11E6 antibody, has at least 90% amino acid sequence identity with a sequence comprising a heavy chain variable region (VH region) comprising the sequence of SEQ ID NO: 9; and SEQ ID NOs: 10, 11, and 12 which are residues 31-35, 50-66, and 99-109 of SEQ ID NO: 9, respectively. The mAb11E6 antibody of the present invention has at least 90% amino acid sequence identity with a sequence comprising a light chain variable region (VL region) comprising the sequence of SEQ ID NO: 13, and SEQ ID NOs: 14, 15, and 16 which are residues 24-34, 50-56, 89-97 of SEQ ID NO: 13, respectively. The mAb11E6 binds to the C-2 domain of RAGE, does not bind to peptides with amino acid sequences used to generate polyclonal antibodies, and is able to neutralize in vivo the effect of Aβ1-40 on cerebral vasculature in mice.

Another of the monoclonal antibodies of the present application, the mAb4E5 antibody, has at least 90% amino acid sequence identity with a sequence comprising a heavy chain variable region (VH region) comprising the sequence of SEQ ID NO: 17; and SEQ ID NOs: 18, 19, and 20 which are residues 31-35, 50-66, and 99-109 of SEQ ID NO: 17, respectively. The mAb4E5 antibody of the present invention has at least 90% amino acid sequence identity with a sequence comprising a light chain variable region (VL region) comprising the sequence of SEQ ID NO: 21, and SEQ ID NOs: 22, 23, and 24 which are residues 24-34, 50-56, 89-97 of SEQ ID NO: 21, respectively.

It is also intended that the isolated monoclonal antibodies that interact with RAGE of the present application may be a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Protein glycosylation depends on the amino acid sequence of the protein of interest, as well as the host cell in which the protein is expressed. Different organisms may produce different glycosylation enzymes (eg., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid.

The antibodies of the present application comprise a heavy chain constant region, such as an IgG1, IgG2, IgG3, IgG4, IgA, IgE, IgM or IgD constant region. Furthermore, the antibody can comprise a light chain constant region, either a kappa light chain constant region or a lambda light chain constant region. Particularly, the antibody comprises a kappa light chain constant region. Alternatively, the antibody portion can be, for example, a Fab fragment or a single chain Fv fragment. Replacements of amino acid residues in the Fc portion to alter antibody effector function are known in the art (Winter, et al. U.S. Pat. Nos. 5,648,260; 5,624,821). The Fc portion of an antibody mediates several important effector functions, e.g. cytokine induction, ADCC, phagocytosis, complement dependent cytotoxicity (CDC) and half-life/clearance rate of antibody and antigen-antibody complexes. In some cases these effector functions are desirable for therapeutic antibodies but in other cases might be unnecessary or even deleterious, depending on the therapeutic objectives. Certain human IgG isotypes, particularly IgG1 and IgG3, mediate ADCC and CDC via binding to Fcγ Rs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

BRIEF DESCRIPTION OF THE FIGURES

FIG. 2 shows characterization of monoclonal antibodies 7F9, 11E6, and 4E5 by dot blot binding.

FIGS. 3A-3C show ELISA binding experiments of monoclonal antibodies of the invention to different RAGE fragments.

SEQUENCE LISTING

Figure 1A:
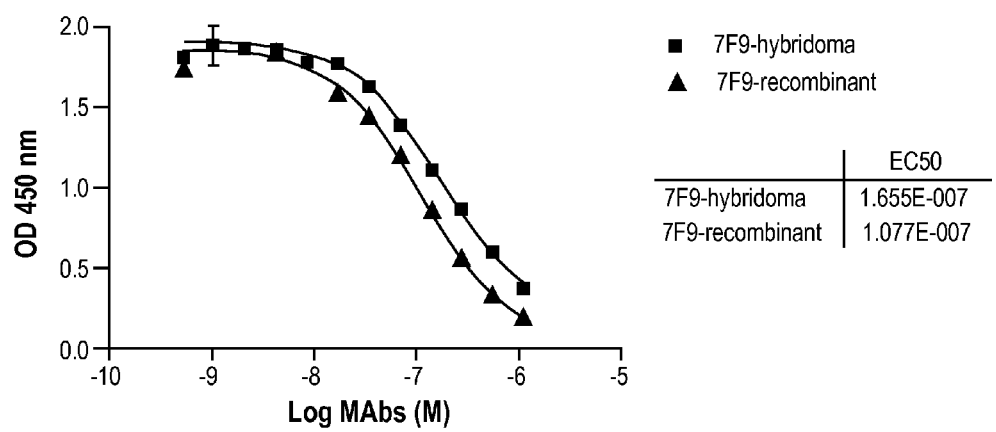
FIGS. 1A-1C show ELISA binding of recombinant and hybridoma-derived anti-human RAGE monoclonal antibodies 7F9, 11E6, and 4E5 to recombinant human RAGE.

SEQ ID NO: 1: amino acid sequence of mAb VH 7F9
SEQ ID NO: 2: amino acid sequence of mAb VH 7F9 CDR-H1
SEQ ID NO: 3: amino acid sequence of mAb VH 7F9 CDR-H2
SEQ ID NO: 4: amino acid sequence of mAb VH 7F9 CDR-H3
SEQ ID NO: 5: amino acid sequence of mAb VL 7F9
SEQ ID NO: 6: amino acid sequence of mAb VL 7F9 CDR-L1
SEQ ID NO: 7: amino acid sequence of mAb VL 7F9 CDR-L2
SEQ ID NO: 8: amino acid sequence of mAb VL 7F9 CDR-L3
SEQ ID NO: 9: amino acid sequence of mAb VH 11E6
SEQ ID NO: 10: amino acid sequence of mAb VH 11E6 CDR-H1
SEQ ID NO: 11: amino acid sequence of mAb VH 11E6 CDR-H2
SEQ ID NO: 12: amino acid sequence of mAb VH 11E6 CDR-H3
SEQ ID NO: 13: amino acid sequence of mAb VL 11E6
SEQ ID NO: 14: amino acid sequence of mAb VL 11E6 CDR-L1
SEQ ID NO: 15: amino acid sequence of mAb VL 11E6 CDR-L2
SEQ ID NO: 16: amino acid sequence of mAb VL 11E6 CDR-L3
SEQ ID NO: 17: amino acid sequence of mAb VH 4E5
SEQ ID NO: 18: amino acid sequence of mAb VH 4E5 CDR-H1
SEQ ID NO: 19: amino acid sequence of mAb VH 4E5 CDR-H2
SEQ ID NO: 20: amino acid sequence of mAb VH 4E5 CDR-H3
SEQ ID NO: 21: amino acid sequence of mAb VL 4E5

SEQ ID NO: 22: amino acid sequence of mAb VL 4E5 CDR-L1
SEQ ID NO: 23: amino acid sequence of mAb VL 4E5 CDR-L2
SEQ ID NO: 24: amino acid sequence of mAb VL 4E5 CDR-L3
SEQ ID NO: 25: amino acid sequence of human Ig gamma1 heavy chain constant region
SEQ ID NO: 26: amino acid sequence of human Ig kappa light chain constant region
SEQ ID NO: 27: Full plasmid nucleotide sequence of Construct #1 (bold) encoding OmpA-[RAGE (23-340)]-6His
SEQ ID NO: 28: Full plasmid nucleotide sequence of Construct #2 (bold) encoding 6His-(Thr)-[RAGE (24-129)]
SEQ ID NO: 29: Full plasmid nucleotide sequence of Construct #3 (bold) encoding 6His-(Thr)-[RAGE (24-234)]
SEQ ID NO: 30: Full plasmid nucleotide sequence of Construct #4 (bold) encoding 6His-(Thr)-[RAGE (24-336)]
SEQ ID NO: 31: Full plasmid nucleotide sequence of Construct #5 (bold) encoding 6His-(Thr)-[RAGE (130-234)]
SEQ ID NO: 32: Full plasmid nucleotide sequence of Construct #6 (bold) encoding 6His-(Thr)-[RAGE (130-336)]
SEQ ID NO: 33: Full plasmid nucleotide sequence of Construct #7 (bold) encoding 6His-(Thr)-[RAGE (235-336)]
SEQ ID NO: 34: encoded amino acid sequence RAGE protein #1
SEQ ID NO: 35: encoded amino acid sequence RAGE protein #2
SEQ ID NO: 36: encoded amino acid sequence RAGE protein #3
SEQ ID NO: 37: encoded amino acid sequence RAGE protein #4
SEQ ID NO: 38: encoded amino acid sequence RAGE protein #5
SEQ ID NO: 39: encoded amino acid sequence RAGE protein #6
SEQ ID NO: 40: encoded amino acid sequence RAGE protein #7
SEQ ID NO:41: Ig gamma-1 constant region mutant amino acid sequence
SEQ ID NO:42: Ig gamma-2 constant region amino acid sequence
SEQ ID NO:43: framework amino acid sequence VH7-4.1/JH6 FR1
SEQ ID NO:44: framework amino acid sequence VH7-4.1/JH6 FR2 and VH1-2/JH6 FR2
SEQ ID NO:45: framework amino acid sequence VH7-4.1/JH6 FR3
SEQ ID NO:46: framework amino acid sequence VH7-4.1/JH6 FR4 and VH1-2/JH6 FR4
SEQ ID NO:47: framework amino acid sequence VH1-2/JH6 FR1
SEQ ID NO:48: framework amino acid sequence VH1-2/JH6 FR3
SEQ ID NO:49: framework amino acid sequence 1-12/L5/JK2 FR1
SEQ ID NO:50: framework amino acid sequence 1-12/L5/JK2 FR2
SEQ ID NO:51: framework amino acid sequence 1-12/L5/JK2 FR3
SEQ ID NO:52: framework amino acid sequence 1-12/L5/JK2 FR4 and 3-15/L2/JK2 FR4
SEQ ID NO:53: framework amino acid sequence 3-15/L2/JK2 FR1
SEQ ID NO:54: framework amino acid sequence 3-15/L2/JK2 FR2
SEQ ID NO:55: framework amino acid sequence 3-15/L2/JK2 FR3
SEQ ID NO:56: CDR-grafted amino acid sequence VH 11E6.1-GL
SEQ ID NO:57: CDR-grafted amino acid sequence VH 11E6.2-GL
SEQ ID NO:58: CDR-grafted amino acid sequence VL 11E6.1-GL
SEQ ID NO:59: CDR-grafted amino acid sequence VL 11E6.2-GL
SEQ ID NO: 60: amino acid sequence of hRAGE
SEQ ID NO: 61: amino acid sequence of a husRAGE fragment
SEQ ID NO: 62: humanized antibody sequence VH h11E6.1
SEQ ID NO: 63: humanized antibody sequence VL h11E6.1
SEQ ID NO: 64: humanized antibody sequence VL h11E6.2
SEQ ID NO: 65: humanized antibody sequence VL h11E6.3
SEQ ID NO: 66: humanized antibody sequence VL h11E6.4
SEQ ID NO: 67: humanized antibody sequence VH h11E6.5
SEQ ID NO: 68: humanized antibody sequence VH h11E6.9
SEQ ID NO: 69: humanized antibody sequence VH h11E6.16
SEQ ID NO:70: amino acid sequence of RAGE-derived peptide NtermR31
SEQ ID NO:71: amino acid sequence of RAGE-derived peptide 1
SEQ ID NO:72: amino acid sequence of RAGE-derived peptide 2
SEQ ID NO:73: amino acid sequence of RAGE-derived peptide 3
SEQ ID NO:74: amino acid sequence of RAGE-derived peptide 4
SEQ ID NO:75: amino acid sequence of RAGE-derived peptide 5
SEQ ID NO:76: amino acid sequence of RAGE-derived peptide 6
SEQ ID NO:77: amino acid sequence of RAGE-derived peptide 7
SEQ ID NO:78: amino acid sequence of RAGE-derived peptide 8
SEQ ID NO:79: amino acid sequence of RAGE-derived peptide 9
SEQ ID NO:80: amino acid sequence of RAGE-derived peptide 10
SEQ ID NO:81: nucleotide sequence of oligonucleotide primers
SEQ ID NO:82: nucleotide sequence of oligonucleotide primers
SEQ ID NO:83: nucleotide sequence of oligonucleotide primers
SEQ ID NO:84: nucleotide sequence of oligonucleotide primers
SEQ ID NO:85: nucleotide sequence of oligonucleotide primers
SEQ ID NO:86: nucleotide sequence of oligonucleotide primers
SEQ ID NO:87: nucleotide sequence of oligonucleotide primers
SEQ ID NO:88: nucleotide sequence of oligonucleotide primers
SEQ ID NO:89: nucleotide sequence of oligonucleotide primers
SEQ ID NO:90: nucleotide sequence of oligonucleotide primers
SEQ ID NO:91: nucleotide sequence of oligonucleotide primers
SEQ ID NO:92: nucleotide sequence of oligonucleotide primers SEQ ID NO:93: nucleotide sequence of oligonucleotide primers
SEQ ID NO:94: nucleotide sequence of oligonucleotide primers
SEQ ID NO:95: amino acid sequence of a His tag (His His His His His His)
SEQ ID NO:96: amino acid sequence of a His tag (His His His His His His Thr)
SEQ ID NO:97: amino acid sequence—Gly Gly Gly Gly Ser

DETAILED DESCRIPTION

1. General Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, selected terms are defined below.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The term "Receptor for Advanced Glycation Endproducts (RAGE)" designates a multiligand receptor in the immunoglobulin family, which binds soluble Aβ peptide, S100b, and HMGB1 (also known as amphoterin) among others. RAGE mediates patho-physiologically relevant cellular changes in response to binding to these ligands. Transgenic animals overexpressing RAGE and human APP display early abnormalities in spatial learning and memory, indicating that RAGE is a cofactor for Aβ-induced neuronal perturbation in Alzheimer-type pathologies, and suggesting that RAGE is a potential therapeutic target to ameliorate cellular dysfunction.

The structure of RAGE has not been solved. Homology to other proteins leads to a model where RAGE has several domains. These domains are named in analogy to immunoglobulins: (i) V-like domain at the N-terminus: this equivalent domain in immunoglobulins binds antigen and represents the only binding region within these proteins. In RAGE, this domain binds to some ligands like S100 (Ostendorp et al. *EMBO J.* 26, 3875, 2007; Leclerc et al. *JBC* 282, 31317, 2007). A monoclonal antibody binding to the v-like domain in RAGE competes with binding of different ligands S100b, HMGB1, and amyloid β (WO 2007/109749 (A2)) implying that these ligands would also bind to RAGE via this same domain. (ii) First C2-like domain: Two domains within RAGE have homology to the C2 domains of immunoglobulins; one of these domains has been called C1 (nomenclature also used by Ostendorp et al. Biochem Biophys Res Comm 2006; 347: 4-11). Several ligands binding to this domain have been described, for instance, S100A12 (also called ENRAGE or Calgranulin C), which binds with an affinity of $K_d$=90 nM (Hofmann et al. *Cell* 97, 889, 1999; Xie et al. *JBC,* 282, 4218, 2007). Aβ competes with S100A12 for this domain, suggesting that Aβ also binds to the C1-domain. (iii) Second C2-like domain: this domain is called C2 (also used by Ostendorp et al. *Biochem Biophys Res Comm* 2006; 347: 4-11). RAGE ligand S100A6 binds to the C2 domain and an antibody generated against a peptide from the C2 domain was shown to compete against S100A6 for this binding; the antibody lead to reduced signal transduction in SH-SY5Y (Leclerc et al. *JBC* 282, 31317, 2007).

A "RAGE domain" may be defined in line with different definitions provided in the state of the art:

According to Xie et al. 2007, *J. Biol. Chem.*, Vol. 282:4218-4231 the following definition of h RAGE domains applies:
  the V domain (amino acids 24-129 of SEQ ID NO:60),
  the C1 domain (amino acids 130-234 of SEQ ID NO:60),
  the C2 domain (amino acids 235-336 of SEQ ID NO:60), According to a more recent definition by Hudson et al, *The FASEB Journal.* 2008; 22:1572-1580, h RAGE (404 amino acid residues according to SEQ ID NO:60) has an extracellular region (amino acids 1-342 of SEQ ID NO:60) composed of
  a signal peptide (amino acids 1-22 of SEQ ID NO:60), followed by three immunoglobulin-like domains, including
    an Ig-like V-type domain (amino acids 23-116 of SEQ ID NO:60) and two Ig-like C2-type 1/2 domains (amino acids 124-221 of SEQ ID NO:60; also designated C1 domain; and amino acids 227-317 of SEQ ID NO:60; also designated C2 domain);

a single transmembrane domain (amino acids 343-363 of SEQ ID NO:60), and a short cytoplasmic tail (amino acids 364-404 of SEQ ID NO:60).

In view of the high degree of identity, in particular with respect to the definition of domains V, C1 and C2, and unless otherwise stated, each of the definitions may be applied in order to define the binding characteristics of the binding proteins of the present invention.

As indicated above, RAGE is capable of binding different ligands via different domains. Results from competition experiments with other ligands seem to indicate that Aβ binds to the C1-domain (Hofmann et al. *Cell* 97, 889, 1999 or Xie et al. *JBC*, 282, 4218, 2007). As non-limiting examples of RAGE ligands there may be mentioned:

Advanced glycation end products (AGEs), (Baynes J. W., 1991, *Diabetes*. 1991, 40:405-412; Ahmed K. A., 2007, *J Clin Biochem Nutr.* 41 (2):97-105);

Members of the S100/calgranulin family (e.g., calgranulin C (also known as ENRAGE and S100A12), S100A1, S100A4, S100A11, S100A13, S100B, and S100P);

Amyloid-β-peptide (Aβ), as for example Aβ 1-40 peptide

Amyloid-β globulomers; as for example Aβ1-42, Aβ12-42, Aβ20-42 globulomers (see Barghorn et al., Globular amyloid β peptide 1-42 oligomer—a homogenous and stable neuropathological protein in Alzheimer's disease) *Journal of Neurochemistry*. 95(3):834-847, November 2005; WO 2007/062852; WO 2008/150949; all incorporated by reference);

eukocyte integrins (e.g., Mac-1)

The term "RAGE" as used herein, particularly refers to human RAGE, also designated "hRAGE" or "huRAGE". Unless otherwise stated the term "RAGE" also encompasses RAGE molecules isolated or obtained from other, different from human, species, as for example, rodents, like mice or rats; or bovine RAGE molecules.

The term "sRAGE" refers to a soluble form of RAGE, derived from the extra cellular domain of RAGE. For example, a sRAGE molecule derived from human RAGE, also designated as husRAGE comprises amino acid residues 1 to 331 (see SEQ ID NO: 61) of human RAGE (see SEQ ID NO: 60).

"Biological activity" as used herein, refers to all inherent biological properties of RAGE as defined herein.

The terms "specific binding" or "specifically binding", as used herein, in reference to the interaction of an antibody, a protein, or a peptide with a second chemical species, mean that the interaction is dependent upon the presence of a particular structure (e.g., an "antigenic determinant" or "epitope" as defined below) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below. An antibody is said to be "capable of binding" a molecule if it is capable of specifically reacting with the molecule to thereby bind the molecule to the antibody.

A "monoclonal antibody" as used herein is intended to refer to a preparation of antibody molecules, which share a common heavy chain and common light chain amino acid sequence, in contrast with "polyclonal" antibody preparations that contain a mixture of different antibodies. Monoclonal antibodies can be generated by several novel technologies like phage, bacteria, yeast or ribosomal display, as well as classical methods exemplified by hybridoma-derived antibodies (e.g., an antibody secreted by a hybridoma prepared by hybridoma technology, such as the standard Kohler and Milstein hybridoma methodology ((1975) *Nature* 256:495-497).

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG 4, IgA1 and IgA2) or subclass.

The term "antigen-binding portion" or "antigen-binding fragment" of an antibody (or simply "antibody portion" or "antibody fragment"), as used herein, refers to one or more fragments of an antibody that retain the ability to specifically bind to an antigen (e.g., RAGE). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

The term "antibody construct" as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) *Proc. Natl. Acad. Sci. USA* 90:6444-6448; Poljak, R. J., et al. (1994) *Structure* 2:1121-1123). An immunoglobulin constant domain refers to a heavy or light chain constant domain. Human IgG heavy chain and light chain constant domain amino acid sequences are known in the art and represented in Table 1.

the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds human RAGE is substantially free of antibodies that specifically bind antigens other than human RAGE). An isolated antibody that specifically binds human RAGE may, however, have cross-reactivity to other antigens, such as RAGE molecules from other species. More-

TABLE 1

Sequence of human IgG heavy chain constant domain and light chain constant domain

| Protein | Sequence Identifier | Sequence<br>123456789012345678901234567890 |
|---|---|---|
| Ig gamma-1 constant region | SEQ ID NO: 25 | ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK |
| Ig gamma-1 constant region mutant | SEQ ID NO: 41 | ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPEAAGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK |
| Ig gamma-2 constant region | SEQ ID NO: 42 | ASTKGPSVFPLAPCSRSTSESTAALGCLVK<br>DYFPEPVTVSWNSGALTSGVHTFPAVLQSS<br>GLYSLSSVVTVPSSNFGTQTYTCNVDHKPS<br>NTKVDKTVERKCCVECPPCPAPPVAGPSVF<br>LFPPKPKDTLMISRTPEVTCVVVDVSHEDP<br>EVQFNWYVDGVEVHNAKTKPREEQFNSTFR<br>VVSVLTVVHQDWLNGKEYKCKVSNKGLPAP<br>IEKTISKTKGQPREPQVYTLPPSREEMTKN<br>QVSLTCLVKGFYPSDIAVEWESNGQPENNY<br>KTTPPMLDSDGSFFLYSKLTVDKSRWQQGN<br>VFSCSVMHEALHNHYTQKSLSLSPGK |
| Ig Kappa constant region | SEQ ID NO: 26 | TVAAPSVFIFPPSDEQLKSGTASVVCLLNN<br>FYPREAKVQWKVDNALQSGNSQESVTEQDS<br>KDSTYSLSSTLTLSKADYEKHKVYACEVTH<br>QGLSSPVTKSFNRGEC |

Still further, an antibody or antigen-binding portion thereof may be part of larger immunoadhesion molecules, formed by covalent or noncovalent association of the antibody or antibody portion with one or more other proteins or peptides. Examples of such immunoadhesion molecules include use of over, an isolated antibody may be substantially free of other cellular material and/or chemicals.

The term "human antibody", as used herein, is intended to include antibodies having variable and constant regions derived from human germline immunoglobulin sequences.

The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (Hoogenboom H. R., (1997) *TIB Tech.* 15:62-70; Azzazy H., and Highsmith W. E., (2002) *Clin. Biochem.* 35:425-445; Gavilondo J. V., and Larrick J. W. (2002) *BioTechniques* 29:128-145; Hoogenboom H., and Chames P. (2000) *Immunology Today* 21:371-378), antibodies isolated from an animal (e.g., a mouse) that is transgenic for human immunoglobulin genes (see e.g., Taylor, L. D., et al. (1992) *Nucl. Acids Res.* 20:6287-6295; Kellermann S-A., and Green L. L. (2002) *Current Opinion in Biotechnology* 13:593-597; Little M. et al (2000) *Immunology Today* 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies which comprise heavy and light chain variable region sequences from one species and constant region sequences from another species, such as antibodies having murine heavy and light chain variable regions linked to human constant regions. The chimeric antibody can be produced through recombinant molecular biological techniques, or may be physically conjugated together.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 50, 55, 60, 65, 70, 75 or 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 50, 55, 60, 65, 70, 75 or 80%, particularly, at least 85%, at least 90%, at least 95%, at least 98%, at least 99% or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., *Sequences of Proteins of Immunological Interest* (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, *J. Mol. Biol.* 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs.

Other boundaries defining CDRs overlapping with the Kabat CDRs have been described by Padlan (*FASEB J.* 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although particular embodiments use Kabat or Chothia defined CDRs.

As used herein, the term "canonical" residue refers to a residue in a CDR or framework that defines a particular canonical CDR structure as defined by Chothia et al. (*J. Mol. Biol.* 196:901-907 (1987); Chothia et al., *J. Mol. Biol.* 227: 799 (1992), both are incorporated herein by reference). According to Chothia et al., critical portions of the CDRs of many antibodies have nearly identical peptide backbone conformations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a particular embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the invention the human heavy chain and light chain acceptor sequences are selected from the sequences described in Table 2 and Table 3. Different combinations for human framework sequences FR1 to FR4 are stated in said tables.

TABLE 2

Human heavy chain acceptor sequences

| SEQ ID NO | Protein region | Sequence 123456789012345678901234567890012 |
|---|---|---|
| 43 | VH7-4.1/JH6 FR1 | QVQLVQSGSELKKPGASVKVSCKASGYTFT |
| 44 | VH7-4.1/JH6 FR2 | WVRQAPGQGLEWMG |
| 45 | VH7-4.1/JH6 FR3 | RFVFSLDTSVSTAYLQICSLKAEDTAVYYCAR |
| 46 | VH7-4.1/JH6 FR4 | WGQGTTVTVSS |
| 47 | VH1-2/JH6 FR1 | QVQLVQSGAEVKKPGASVKVSCKASGYTFT |
| 44 | VH1-2/JH6 FR2 | WVRQAPGQGLEWMG |
| 48 | VH1-2/JH6 FR3 | RVTMTRDTSISTAYMELSRLRSDDTAVYYCAR |
| 46 | VH1-2/JH6 FR4 | WGQGTTVTVSS |

TABLE 3

Human light chain acceptor sequences

| SEQ ID NO | Protein region | Sequence 123456789012345678901234567890012 |
|---|---|---|
| 49 | 1-12/L5/JK2 FR1 | DIQMTQSPSSVSASVGDRVTITC |
| 50 | 1-12/L5/JH2 FR2 | WYQQKPGKAPKLLIY |
| 51 | 1-12/L5/JH2 FR3 | GVPSRFSGSGSGTDFTLTISSLQPEDFATYYC |
| 52 | 1-12/L5/JH2 FR4 | FGQGTKLEIKR |
| 53 | 3-15/L2/JH2 FR1 | EIVMTQSPATLSLSPGERATLSC |
| 54 | 3-15/L2/JH2 FR2 | WYQQKPGQAPRLLIY |
| 55 | 3-15/L2/JH2 FR3 | GIPARFSGSGSGTDFTLTISSLQSEDFAVYYC |
| 52 | 3-15/L2/JH2 FR4 | FGQGTKLEIKR |

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., *Crit. Rev. Immunol.* 22(3): 183-200 (2002); Marchalonis et al., *Adv Exp Med. Biol.* 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

The term "humanized antibody" generally refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

In particular, the term "humanized antibody" as used herein, is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 50, 55, 60, 65, 70, 75 or 80%, particularly at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. Particularly, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgY, IgM, IgG, IgD, IgA and IgE, and any isotype, including without limitation IgA1, IgA2, IgG1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a particular embodiment, such mutations, however, will not be extensive. Usually, at least 50, 55, 60, 65, 70, 75 or 80%, particularly at least 85%, more particularly at least 90%, and in particular at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, *From Genes to Clones* (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, *J. Mol. Biol.* 224:487-499, which is incorporated herein by reference). Vernier zone residues form a layer underlying the CDRs and may impact on the structure of CDRs and the affinity of the antibody.

The term "inhibition of binding" of RAGE to one of his ligands as used herein encompasses partial (as for example by about 1 to 10% or more, in particular about 20%, 30%, 40%, 50%, 60%, 70%, 80%, 85%, 90%, or 95% or more) or complete reduction of said ligand binding activity. Said "inhibition of binding" may be determined by any suitable method available in the art, preferably by any method as exemplified herein, as for example HTRF assays described herein.

As used herein, the term "neutralizing" refers to neutralization of biological activity of a target protein when a binding protein specifically binds the target protein. Neutralizing may be the result of different ways of binding of said binding protein to the target. For example, neutralizing may be caused by binding of the binding protein in a region of the target, which does not affect receptor binding to the target molecule. Alternatively binding of a binding protein may result in a blockade of the receptor binding to the target, which blockade finally neutralizes the target protein activity. Each of said different mechanism may occur according to the invention.

Particularly a neutralizing binding protein is a neutralizing antibody whose binding to RAGE results in neutralization of a biological activity of RAGE. Particularly the neutralizing binding protein binds RAGE and reduces a biologically activity of RAGE by at least about 1 to 10%, at least about 20%, 30%, 40%, 50%, 60%, 70%, 80%, 85% or more. Neutralization of a biological activity of RAGE by a neutralizing binding protein can be assessed by measuring one or more indicators of RAGE biological activity well known in the art.

An "inhibition of soluble Aβ1-40 peptide-induced reduction of cerebral blood volume" determined in vivo in an animal model relates to a partial or complete inhibition, as for example by at least about 1 to 10%, at least about 15%, 20%, 30%, 40%, 50%, 60%, 70%, 80%, 85% or more, if compared to a non-treated control, or in particular, if compared to a negative, monoclonal or polyclonal, immunoglobulin-isotype control.

An "improvement of the cerebral blood volume" as in vivo in an animal model over-expressing human APP, relates to a statistically significant improvement of CBV, if compared to a non-treated control, or in particular, if compared to a negative, monoclonal or polyclonal, immunoglobulin-isotype control.

A "reduction of amyloid plaque number and/or amyloid plaque area" as measured in vivo in an animal model over-expressing human APP relates to a partial or complete reduction, as for example by at least about 1 to 10%, at least about 15%, 20%, 30%, 40%, 50%, 60%, 70%, 80%, 85% or more, if compared to a non-treated control, or in particular, if compared to a negative, monoclonal or polyclonal, immunoglobulin-isotype control.

An "inhibition of aggregated Aβ1-40 peptide-induced dynamin cleavage of hippocampal neurons in vitro; relates to a partial or complete inhibition, as for example by at least about 1 to 10%, at least about 15%, 20%, 30%, 40%, 50%, 60%, 70%, 80%, 85% or more, if compared to a non-treated control, or in particular, if compared to a negative, monoclonal or polyclonal, immunoglobulin-isotype control.

A "reversal of Aβ1-42 globulomer-induced reduction of synaptic transmission" in vitro, relates to a partial or complete reversal, as for example by at least about 1 to 10%, at least about 15%, 20%, 30%, 40%, 50%, 60%, 70%, 80%, 85% or more, if compared to a non-treated control, or in particular, if compared to a negative, monoclonal or polyclonal, immunoglobulin-isotype control.

A "neutralizing monoclonal antibody" as used herein is intended to refer to a preparation of antibody molecules, which upon binding to the specific antigen are able to compete and inhibit the binding of the natural ligand for said antigen. In a particular embodiment of the present application, the neutralizing antibodies of the present invention are capable of competing with RAGE for binding to at least one of its ligands, in particular a ligand selected from Aβ-peptides, Aβ-globulomers, S100b and Amphoterin, and to prevent RAGE biological activity or function.

The term "activity" includes activities such as the binding specificity/affinity of an antibody for an antigen, for example, an anti-RAGE antibody that binds to an RAGE antigen and/or the neutralizing potency of an antibody, for example, an anti-RAGE antibody whose binding to RAGE neutralizes the biological activity of RAGE.

The term "hyperalgesia" refers to an increased response to a stimulus which is normally painful. Hyperalgesia reflects increased pain on suprathreshold stimulation.

The term "allodynia" refers to pain due to a stimulus which does not normally provoke pain.

The term "neuropathic pain" is pain initiated or caused by a primary lesion or dysfunction in the nervous system.

The term "attenuation of established hyperalgesia" includes reduction in behavioral responses to applied mechanical, thermal or chemical stimuli to animals in vivo model of neuropathic or inflammatory pain. It is important to note that the attenuation of established hyperalgesia is distinct from prevention of development of hyperalgesia.

The "biological function" or "activity" of RAGE may be described as that of a signal transducing cell surface receptor for Aβ or a receptor that mediates transport of proteins into or through the cell.

The term "epitope" or "antigenic determinant" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnsson, B., et al. (1991) *Anal. Biochem.* 198:268-277.

The term "$k_{on}$", as used herein, is intended to refer to the on rate constant for association of an antibody to the antigen to form the antibody/antigen complex as is known in the art.

The term "$k_{off}$", as used herein, is intended to refer to the off rate constant for dissociation of an antibody from the antibody/antigen complex as is known in the art.

The term "$K_d$", as used herein, is intended to refer to the dissociation constant of a particular antibody-antigen interaction as is known in the art.

The term "labelled binding protein" as used herein, refers to a protein with a label incorporated that provides for the identification of the binding protein. Particularly, the label is a detectable marker, e.g., incorporation of a radiolabelled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. Particularly the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, *Crystallization of Nucleic Acids and Proteins, a Practical Approach*, 2nd ea., pp. 20 1-16, Oxford University Press, New York, N.Y., (1999)."

The term "polynucleotide" as referred to herein shall mean a polymeric form of two or more nucleotides, either ribonucleotides or deoxynucleotides or a modified form of either type of nucleotide. The term includes single and double stranded forms of DNA but particularly is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences, which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Particularly host cells include prokaryotic and eukaryotic cells selected from any of the Kingdoms of life. Particular eukaryotic cells include protist, fungal, plant and animal cells. In particular host cells include but are not limited to the prokaryotic cell line *E. coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "regulate" and "modulate" are used interchangeably, and, as used herein, refers to a change or an alteration in the activity of a molecule of interest (e.g., the biological activity of RAGE). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of RAGE). For example, a modulator may cause an increase or decrease in the magnitude of a certain activity or function of a molecule compared to the magnitude of the activity or function observed in the absence of the modulator.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, RAGE polypeptides or polypeptides, nucleic acids, carbohydrates, or any other molecules that bind to RAGE.

The term "antagonist", as used herein, refer to a modulator that, when contacted with a molecule of interest causes a decrease in the magnitude of a certain activity or function of the molecule compared to the magnitude of the activity or function observed in the absence of the antagonist. Exemplary antagonists include, but are not limited to, proteins, peptides, antibodies, peptibodies, carbohydrates or small organic molecules. Peptibodies are described, e.g., in WO01/83525.

Particular antagonists of interest include those that block or modulate the biological or immunological activity of RAGE. Antagonists of RAGE may include, but are not limited to, proteins, nucleic acids, carbohydrates, or any other molecules, which bind to RAGE, particularly monoclonal antibodies that interact with the RAGE molecule. It should be noted that the interaction with RAGE may result in binding and neutralization of other ligands/cell membrane components, and may be useful for additive or synergistic functioning against multiple diseases.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

2. Uses of RAGE Antibodies

Ligands of RAGE include S100/calgranulins, HMGB1 and MAC-1, among others. Activation of RAGE by its ligands triggers signaling cascades that involve MAP kinases and nuclear translocation of nuclear factor kappa B (NF-κB) (Ramasamy et al. *Glycobiology*, 2005; 15(7): 16R-28R). S100/calgranulins are expressed by polymorphonuclear leukocytes, dendritic cells (DC), macrophages (MP), and lymphocytes (Zimmer et al., *Brain Res Bull.* 1995; 37(4): 417-429; Schafer and Heinzmann, Trends Biochem Sci, 1996 21(4):134-40; Donato, *Int J Biochem Cell Biol.* 2001; 33(7): 637-68). Many of these proteins were shown to play a role in diseases that have a clear inflammatory component. For example, S100A12 was shown to be released by neutrophils at sites of inflammation, and was shown to play a role in the Kawasaki disease (Leclerc et al. *Biochem Biophys Acta*, 2009; 1793: 993-1007, Boussac et al. *Electrophoresis*, 2000; 21(3):665-72; Foell et al. *Lancet*, 2003; 21(3):665-672). Another ligand of RAGE, MAC-1 (CD11b/CD18) promotes leucocyte extravasation into inflamed tissue in a RAGE-dependent manner (Chavakis et al. *J Exp Med*, 2003; 198(10): 1507-15). Along the same lines, pro-inflammatory cytokine HMGB1 is upregulated in synovial tissues of patients with rheumatoid arthritis (Kokkola et al. *Arthritis Rheum*, 2002; 46(10):2598-603). On the other hand, S100B protein is increased in the lumbar spinal cords of both rats and mice following 14 days after the lumbar L5 spinal nerve transaction (Tanga et al. *Neuroscience*, 2006; 140(3):1003-10). Overexpression of S100B in the transgenic mice leads to a significantly decreased tactile threshold responses. Conversely, in the S100B knock-out mice tactile thresholds (reduced response to non-noxious stimuli) are significantly increased implicating S100B protein in the pathophysiology of neuropathic pain (Tanga et al. *Neuroscience*, 2006; 140(3): 1003-10). Well-documented role of some 5100 proteins in inflammatory processes and provides a rationale for therapeutic interventions that target. RAGE. Two general outcomes of RAGE-mediated cellular activation are induction of a proinflammatory phenotype and upregulation of the receptor itself by activated NF-κB (Ramasamy et al. Glycobiology, 2005; 15(7): 16R-28R).

Evidence of involvement of RAGE and AGEs in diabetic neuropathy has been recently established. Clinical evidence suggests that ligands of RAGE, RAGE itself, activated NF-κB, and IL-6 are colocalized in sural nerve biopsies of patients with diabetes mellitus, and those with impaired glucose tolerance-related diabetic peripheral neuropathy, but not in biopsies of control patients (Bierhaus et al, *J. Clin. Invest.* 2004; 114:1741-1751; Haslbeck et al, *Exp Clin Endocrinol Diabetes.* 2005 May; 113(5):288-91). CML (protein-bound $N^\epsilon$-(carboxymethyl)lysine, an AGE adduct) could be detected in axons, Schwann cells, and endoneurial microvessels of human peripheral nerves. The staining intensity was shown to be significantly increased in diabetic patients and to correlate with myelinated fiber loss (Sugimoto et al, Diabetologia. 1997 December; 40(12):1380-7). In addition, pronounced AGE immunoreactivity was detected in the axons and myelin sheaths of 90% of type 2 diabetic patients, but not in control subjects. The intensity of the axonal AGE immunoreactivity was shown to correlate with the severity of perineurial thickening, microvascular luminal narrowing, and axonal loss characteristic of diabetic neuropathy (Misur et al, Acta Diabetol. 2004 December; 41(4):158-66). The use of RAGE expression as a biomarker for human pathological pain conditions has also been reported. Expression of RAGE, a ligand of RAGE (Nε-carboxymethyllysine), and a signaling molecule associated with RAGE activation (NF-κB) were reported increased in muscle tissue from patients with Fibromyalgia Syndrome, as compared to healthy controls (Ruster et al., *Scand J Rheumatol* 2005; 34:460-463; Hein & Franke, *Rheumatology* (Oxford). 2002 October; 41(10):1163-7).

RAGE expression has been investigated in tissues from normal mice, and from mice with streptozotocin (STZ)-induced diabetic neuropathy. Expression of RAGE is mostly absent in sensory tissues of healthy rodents. RAGE expression in mice is increased in tissues involved in sensory processing following STZ-induced diabetic neuropathy (Toth et al., *Current Molecular Medicine* 2007, 7, 766-776). RAGE expression was reported increased in skin (subcutaneous tissues, blood vessels, and epidermal nerve fibers), in sural nerve glial cells, and in neurons in dorsal root ganglia, spinal cord and hippocampus (Toth et al., Current Molecular Medicine 2007, 7, 766-776). The functional effects of RAGE activation in models of chronic pain are much less understood.

In human patients, diabetic neuropathy often results in a loss of sensation, which has been attributed to loss of sensory nerve fiber innervations in the tissue(s) where sensation is lost. In a mouse model of STZ-induced diabetic neuropathy, RAGE knockout mice, like their wild-type counterparts, have a measurable loss of nerve fiber innervations in the footpads of the hindpaw (Bierhaus et al., *J. Clin. Invest.* 2004, 114: 1741-1751). Nociceptive threshold in the diabetic-RAGE mice was unaltered compared to wild-type, suggesting that RAGE contributes to the functional sensory deficits associated with diabetic neuropathy (Bierhaus et al., *J. Clin. Invest.* 2004, 114:1741-1751). In a pharmacological study, soluble RAGE attenuated thermal hyperalgesia in diabetic (STZ) mice (Bierhaus et al., *J. Clin. Invest.* 2004, 114:1741-1751). In addition to anti-nociceptive efficacy in neuropathic pain models, it is possible that RAGE antibodies will contribute to attenuation of pain resulting from inflammation. For example, the chronic constriction injury model of pain (Bennett, G J & Xie, Y K, *Pain*. 1988 April; 33(1):87-107), is neuropathic in origin, and has a strong peripheral inflammatory component resulting from chromic gut sutures loosely tied around the nerve (Kawakami, M., et al., *Spine* (Phila Pa. 1976). 1994 Aug. 15; 19(16):1780-94; Hurty, C A et al., *Vet Rec.* 2002 Sep. 14; 151(11):324-8).

Given their ability to bind to human RAGE, the neutralizing antibodies of the present application, or portions thereof, can be used to detect human RAGE (e.g., in a biological sample, such as serum or plasma), using a conventional immunoassay, such as an enzyme linked immunosorbent assays (ELISA), a radioimmunoassay (RIA) or tissue immunohistochemistry. The present application provides a method for detecting human RAGE in a biological sample comprising contacting a biological sample with an antibody, or antibody portion, of the invention and detecting either the antibody (or antibody portion) bound to human RAGE or unbound antibody (or antibody portion), to thereby detect human RAGE in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbellifer one, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{131}I$, $^{177}Lu$, $^{166}Ho$, $^{153}Sm$.

The antibodies and antibody portions of the present application particularly are capable of neutralizing human RAGE activity both in vitro and in vivo. Accordingly, such antibodies and antibody portions of the invention can be used to inhibit RAGE binding to its ligands and therefore neutralize the resulting activity.

In another embodiment, the present application provides a method for reducing RAGE activity in a subject, advantageously from a subject suffering from a disease or disorder in which RAGE resulting activity is detrimental. The present application provides methods for reducing RAGE activity in a subject suffering from such a disease or disorder, by preventing RAGE binding to at least one of its ligands, through the use of the monoclonal antibodies of the present application. The antibodies of the present invention, in particular, the humanized antibodies disclosed herein, can be administered to a human subject for therapeutic purposes.

As used herein, the term "a disorder in which RAGE activity is detrimental" is intended to include diseases and other disorders in which the presence of RAGE or its resulting activity in a subject suffering from the disorder has been shown to be or is suspected of being either responsible for the pathophysiology of the disorder or a factor that contributes to a worsening of the disorder. Accordingly, a disorder in which RAGE activity is detrimental is a disorder in which reduction of RAGE activity is expected to alleviate the symptoms and/or progression of the disorder. Non-limiting examples of disorders that can be treated with the antibodies of the invention include those disorders discussed in the section below pertaining to pharmaceutical compositions of the antibodies of the invention.

In addition to pain including chronic pain, diabetic neuropathy and fibromyalgia syndrome, it is recognized that RAGE plays an important role in the pathology associated with a variety of diseases involving neurological diseases selected from the group comprising amytropic lateral sclerosis, brachial plexus injury, brain injury, including traumatic brain injury, cerebral palsy, Friedrich's Ataxia, Guillain Barre, leukodystrophies, multiple sclerosis, post polio, spina bifida, spinal cord injury, spinal muscle atrophy, spinal tumors, stroke, transverse myelititis, dementia, senile dementia, mild cognitive impairment, Alzheimer's disease and related dementia, Huntington's chorea, tardive dyskinesia, hyperkinesias, manias, Morbus Parkinson, steel-Richard syndrome, Down's syndrome, myasthenia gravis, nerve trauma, vascular amyloidosis, cerebral hemorrhage I with amyloidosis, brain inflammation, Friedrich's ataxia, acute confusion disorder, amyotrophic lateral sclerosis, glaucoma, Alzheimer's disease, diabetic nephropathy, sepsis, rheumatoid arthritis and related inflammatory diseases. Diabetes and resulting complications like diabetic retinopathy, nephropathy, vascular complications; atherosclerotic complications, pulmonary fibrosis, cancer—especially melanomas, other amyloidoses. (See for example the following references: Amyloidosis, cancer, arthritis, Crohn's disease, chronic and acute inflammatory diseases: Schmidt A M et al: *J Clin Invest*. 2001 October; 108(7):949-55; cardiovascular diseases, diabetes, diabetic complications: Yan S D et al: *Eur J Clin Invest*. 1997 March; 27(3):179-81; Prion-associated diseases: Sasaki N et al: *Neurosci Lett*. 2002 Jun. 28; 326(2):117-20; vascularitis, nephropathies, retinopathies and neuropathies: Thornalley P J.: *Int Rev Neurobiol.* 2002; 50:37-57; Alzheimer disease: Weldon D T et al: *Geriatrics.* 1997 September; 52 Suppl 2:S13-6; Yan S D et al: *Biochim Biophys Acta.* 2000 Jul. 26; 1502(1):145-57; rheumatoid arthritis, osteoarthritis: Drinda S et al: *Rheumatol Int.* 2004 Mar. 26; bowel disease: Foell D et al: *Gut.* 2003 June; 52(6):847-53; multiple sclerosis: Yan S S et al: *Nat. Med.* 2003 March; 9(3):287-93; psoriasis: Foell D et al: *Rheumatology* (Oxford). 2003 November; 42(11):1383-9: lupus: Tanji N et al: *J Am Soc Nephrol.* 2000 September; 11(9):1656-66; general autoimmune diseases, sepsis: Liliensiek B et al: *J Clin Invest.* 2004 June; 113(11):1641-50; arteriosclerosis and restenosis: Schmidt A M et al: *Circ Res.* 1999 Mar. 19; 84(5):489-97; U.S. patent application Ser. No. 12/437,715 and WO 2009/136382, which are herein incorporated by reference).

Also, DVD immunoglobulins, or dual-specific antibodies between any one of the partners described above may be of use. Such antibody preparations as described above may be useful for the treatment of such diseases.

The antibodies of the present application may also be combined with peptides allowing the trans-membrane transfer to include targeting of intracellular target proteins. Such peptide sequences may include, but are not limited to, tat, antennapedia, poly-args, some anti-microbial peptides. Such peptides may allow transfer through membranes, including cellular plasma membranes, but also epithelia and endothelial membranes, including the blood-brain-barrier, gut mucosa, meninges, and others.

An antibody, or antibody portion, of the present application also can be administered with one or more additional small molecule therapeutic agents useful in the treatment of disorders in which RAGE activity is involved as discussed in the foregoing paragraphs. It should be understood that the antibodies of the present application or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent that affects the viscosity of the composition.

The present invention encompasses a number of embodiments, a non-exhaustive list of which are included below. Other embodiments not listed below shall be apparent upon further reading of this description. However, by way of example, such specific embodiments include:

1. An isolated binding protein that dissociates from human RAGE with a $K_D$ of $1 \times 10^{-7}$ M or less and a $k_{off}$ rate constant of $1 \times 10^{-2}$ s$^{-1}$ or less, both determined by surface plasmon resonance.

1A. i) The binding protein of embodiment 1, that binds to human RAGE and modulates, in particular inhibits, the ability of RAGE to bind to at least one of its ligands, as determined in a standard in vitro assay, as for example, a HTRF assay.

ii) The binding protein of embodiment 1, which is capable of inhibiting a RAGE-mediated biological activity.

iii) A binding protein, in particular, according to one of the preceding embodiments, having at least one of the following biological activities:

a. inhibition of soluble Aβ1-40 peptide-induced reduction of cerebral blood volume (CBV) in vivo in an animal model, like C57BL/6 female mice, as for example described in more detail in the experimental part, in particular example 7 and references cited therein;

b. improvement of the cerebral blood volume in vivo in an animal model over-expressing human APP, like the transgenic Tg2576 mouse model;

c. reduction of amyloid plaque number and/or amyloid plaque area in vivo in an animal model over-expressing human APP, like the transgenic Tg2576 mouse model;

d. inhibition of aggregated Aβ1-40 peptide-induced dynamin cleavage of hippocampal neurons in vitro, like hippocampal neurons as obtained from embryonic rats; and e. reversal of Aβ1-42 globulomer-induced reduction of synaptic transmission in vitro, determined in hippocampal slice cultures.

2. The binding protein of embodiment 1, wherein the ligand is selected from Aβ peptides, Aβ-globulomers, S100b and Amphoterin.

3. The binding protein of one of the preceding embodiments, which is a neutralizing binding protein.

4. The binding protein of one of the preceding embodiments, which is capable of blocking, in particular inhibiting, the binding of Aβ globulomer to human RAGE.

5. The binding protein of one of the preceding embodiments wherein said wherein said Aβ globulomer is Aβ1-42.

6. The binding protein of one of the preceding embodiments, wherein said binding protein interacts with at least one, as for example 2, 3, 4, 5, 6, 7, 8, 9, 10, 11, or 12 amino acid residues of the C1- and/or C2-domain of human RAGE.

7. The binding protein according to one of the preceding embodiments, which is a humanized antibody.

8. The binding protein according to one of the preceding embodiments, comprising an antigen binding domain, said binding protein capable of binding an epitope of a human RAGE molecule, said antigen binding domain comprising at least one CDR comprising an amino acid sequence selected from the CDR-H3 group of amino acid sequences selected from the group consisting of SEQ ID NOs: 12 and 20; and modified CDR amino acid sequences having a sequence identity of at least 50%, as for example at least 55, 60, 65, 70, 75, 80, 85, 90, 95% identity, to one of said sequences; the CDR-L3 group of amino acid sequences selected from the group consisting of SEQ ID NOs: 8, 16 and 24; and modified CDR amino acid sequences having a sequence identity of at least 50%, as for example at least 55, 60, 65, 70, 75, 80, 85, 90, 95% identity, to one of said sequences.

9. A binding protein comprising an antigen binding domain, said binding protein capable of binding an epitope of a human RAGE molecule, said antigen binding domain comprising at least one CDR comprising an amino acid sequence selected from the group consisting of: the CDR-H3 group of amino acid sequences consisting of SEQ ID NOs: 12 and 20; and modified CDR amino acid sequences having a sequence identity of at least 50%, as for example at least 55, 60, 65, 70, 75, 80, 85, 90, 95% identity, to one of said sequences; the CDR-L3 group of amino acid sequences selected from the group consisting of SEQ ID NOs: 8, 16 and 24; and modified CDR amino acid sequences having a sequence identity of at least 50%, as for example at least 55, 60, 65, 70, 75, 80, 85, 90, 95% identity, to one of said sequences.

10. The binding protein according to one of the preceding embodiments, further comprising at least one CDR comprising an amino acid sequence selected from the CDR-H1 group consisting of SEQ ID NOs: 10 and 18; or selected from the CDR-H2 group consisting of SEQ ID NOs: 11 and 19; or selected from the CDR-L1 group consisting of SEQ ID NOs: 14, and 22; or selected from the CDR-L2 group consisting of SEQ ID NOs: 15 and 23; and modified CDR amino acid sequences having a sequence identity of at least 50%, as for example at least 55, 60, 65, 70, 75, 80, 85, 90, 95 or 99% identity, to one of said sequences.

11. The binding protein according to any one of the preceding embodiments, wherein said at least one CDR comprises an amino acid sequence selected from the group consisting of:

| | |
|---|---|
| SEQ ID NO: 10 | Residues 31-35 of SEQ ID NO: 9 |
| SEQ ID NO: 11 | Residues 50-66 of SEQ ID NO: 9 |
| SEQ ID NO: 12 | Residues 97-109 of SEQ ID NO: 9 |
| SEQ ID NO: 14 | Residues 24-34 of SEQ ID NO: 13 |
| SEQ ID NO: 15 | Residues 50-56 of SEQ ID NO: 13 |
| SEQ ID NO: 16 | Residues 89-97 of SEQ ID NO: 13 |
| SEQ ID NO: 18 | Residues 31-35 of SEQ ID NO: 17 |
| SEQ ID NO: 19 | Residues 50-66 of SEQ ID NO: 17 |
| SEQ ID NO: 20 | Residues 99-109 of SEQ ID NO: 17 |
| SEQ ID NO: 22 | Residues 24-34 of SEQ ID NO: 21 |
| SEQ ID NO: 23 | Residues 50-56 of SEQ ID NO: 21 |
| SEQ ID NO: 24 | Residues 89-97 of SEQ ID NO: 21 |

12. The binding protein according to embodiment 11, comprising at least 3 CDRs which are selected from a variable domain CDR set comprising:

| VH 11E6 set | | |
|---|---|---|
| VH 11E6 CDR-H1 | Residues 31-35 of SEQ ID NO: 9 | SEQ ID NO: 10 |
| VH 11E6 CDR-H2 | Residues 50-66 of SEQ ID NO: 9 | SEQ ID NO: 11 |
| VH 11E6 CDR-H3 | Residues 99-109 of SEQ ID NO: 9 | SEQ ID NO: 12 |
| VL 11E6 set | | |
| VL 11E6 CDR-L1 | Residues 24-34 of SEQ ID NO: 13 | SEQ ID NO: 14 |
| VL 11E6 CDR-L2 | Residues 50-56 of SEQ ID NO: 13 | SEQ ID NO: 15 |
| VL 11E6 CDR-L3 | Residues 89-97 of SEQ ID NO: 13 | SEQ ID NO: 16 |
| VH 4E5 set | | |
| VH 4E5 CDR-H1 | Residues 31-35 of SEQ ID NO: 17 | SEQ ID NO: 18 |
| VH 4E5 CDR-H2 | Residues 50-66 of SEQ ID NO: 17 | SEQ ID NO: 19 |
| VH 4E5 CDR-H3 | Residues 99-109 of SEQ ID NO: 17 | SEQ ID NO: 20 |
| VL 4E5 set | | |
| VL 4E5 CDR-L1 | Residues 24-34 of SEQ ID NO: 21 | SEQ ID NO: 22 |
| VL 4E5 CDR-L2 | Residues 50-56 of SEQ ID NO: 21 | SEQ ID NO: 23 |
| VL 4E5 CDR-L3 | Residues 89-97 of SEQ ID NO: 21 | SEQ ID NO: 24 | or a variable domain set wherein at least one of said 3 CDRs is a modified CDR amino acid sequence having a sequence identity of at least 50%, as for example at least 55, 60, 65, 70, 75, 80, 85, 90, 95% identity, to the parent sequence.

13. The binding protein according to embodiment 12, comprising at least two variable domain CDR sets.

14. The binding protein according to embodiment 13, wherein said at least two variable domain CDR sets are from at least one of the below sets:

(a) VH 4E5 set and VL 4E5 set; or
(b) VH 11E6 set and VL 11E6 set.

15. The binding protein according to one of the preceding embodiments, further comprising a human acceptor framework.

16. The binding protein according to embodiment 15, wherein said human acceptor framework comprises at least one amino acid sequence selected from the group consisting of SEQ ID NOs: 43, 44, 45, 46, 47, 48, 49, 50, 51, 52, 53 54 and 55.

17. The binding protein of any one of the preceding embodiments comprising at least one heavy chain variable domain selected from the group consisting of: SEQ ID NOs: 56 and 57; and/or at least one light chain variable domain selected from the group consisting of: SEQ ID NOs: 58 and 59.

18. The binding protein of embodiment 17, wherein said binding protein comprises two variable domains, wherein the two variable domains have amino acid sequences of: SEQ ID NOs: 56 and 58; 56 and 59; 57 and 58; or 57 and 59.

19. The binding protein according to any one of the embodiment 16 to 18, wherein said human acceptor framework comprises at least one framework region amino acid substitution at a key residue, said key residue selected from the group consisting of a residue adjacent to a CDR; a glycosylation site residue; a rare residue; a residue capable of interacting with a RAGE epitope; a residue capable of interacting with a CDR; a canonical residue; a contact residue between heavy chain variable region and light chain variable region; a residue within a Vernier zone; an N-terminal residue capable of para-glutamate formation; and a residue in a region that overlaps between a Chothia-defined variable heavy chain CDR1 and a Kabat-defined first heavy chain framework.

20. The binding protein according to embodiment 19, wherein said key residue comprises (a) at least one heavy chain sequence position selected from the group consisting of: 1, 2, 68, 70, 72, 76, 85, 89 and 95; (b) at least one light chain sequence position selected from the group consisting of: 11, 13, 43, 49, 58, 70 and 87; or (c) combinations of (a) and (b).

21. The binding protein of any one of the preceding embodiments, wherein the binding protein is a consensus human variable domain.

22. The binding protein of any one of the embodiments 16 to 21, wherein said human acceptor framework comprises at least one framework region amino acid substitution, as for example 1 to 20, 1 to 15, 1 to 10, or 2, 3, 4, 5, 6, 7, 8 or 9 substitutions, wherein the amino acid sequence of the framework is at least 65% identical to the sequence of said human acceptor framework and comprises at least 70 amino acid residues identical to said human acceptor framework.

23. The binding protein of any one of the preceding embodiments, wherein said binding protein comprises (a) at least one framework mutation at a position selected from the group consisting of: 62, 67, 68 and 69; (b) at least one light chain framework mutation at a position selected from the group consisting of: 63, 64, 65 and 66; or (c) combinations of (a) and (b).

24. The binding protein of embodiment 23, wherein said binding protein comprises two variable domains, wherein said two variable domains have amino acid sequences from one of the below groups of amino acid sequences:
(a) SEQ ID NOs: 62 and 63; 62 and 64; 62 and 65; or 62 and 66;
(b) SEQ ID NOs: 67 and 63; 67 and 64; 67 and 65; or 67 and 66; or
(c) SEQ ID NOs: 68 and 63; 68 and 64; 68 and 65; or 68 and 66.

25. The binding protein of any one of the preceding embodiments, wherein said binding protein is capable of binding a target, selected from RAGE molecules.

26. The binding protein of any one of the preceding embodiments capable of binding to human RAGE.

27. The binding protein of embodiment 26, having at least one of the following additional functional characteristics: binding to mouse and rat RAGE.

28. The binding protein of any one of the preceding embodiments, wherein the binding protein is capable of modulating, in particular neutralizing, a biological function of a target, selected from RAGE molecules.

29. The binding protein of embodiment 28, wherein said binding protein modulates, in particular inhibits, the ability of RAGE to bind to at least one of its ligands.

30. The binding protein of embodiment 29, wherein said binding protein modulates, in particular inhibits, at least one of the following interactions: binding of human RAGE to Aβ peptides, Aβ-globulomers, S100b and amphoterin.

31. The binding protein of any one of the preceding embodiments, wherein said binding protein is capable of neutralizing a RAGE biological activity, as for example, Aβ-induced cleavage of dynamin in primary neurons, Globulomer induced synaptic deficits in hippocampal slices, or Aβ-induced decrease in CBV.

32. The binding protein of embodiment 31, wherein the RAGE molecule is RAGE or a RAGE fragment, such as sRAGE.

33. The binding protein of embodiment 32, wherein the RAGE is selected from the group consisting of: human, rat and mouse.

34. The binding protein of any one of the preceding embodiments, wherein said binding protein has an on rate constant ($k_{on}$) to said target selected from the group consisting of: at least about $10^2 M^{-1}s^{-1}$; at least about $10^3 M^{-1}s^{-1}$; at least about $10^4 M^{-1}s^{-1}$; at least about $10^5 M^{-1}s^{-1}$; at least about $10^6 {}_M^{-1}{}_s^{-1}$, and at least about $10^7 {}_M^{-1}{}_s^{-1}$ as measured by surface plasmon resonance.

35. The binding protein of any one of the preceding embodiments, wherein said binding protein has an off rate constant ($k_{off}$) to said target selected from the group consisting of: at most about $10^{-2}s^{-1}$; at most about $10^{-3}s^{-1}$; at most about $10^{-4}s^{-1}$; at most about $10^{-5}s^{-1}$; and at most about $10^{-6}s^{-1}$, as measured by surface plasmon resonance.

36. The binding protein of any one of the preceding embodiments, wherein said binding protein has a dissociation constant ($K_D$) to said target selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M.

37. An antibody construct comprising a binding protein described in any one of the preceding embodiments, said antibody construct further comprising a linker polypeptide or an immunoglobulin constant domain.

38. The antibody construct according to embodiment 37, wherein said binding protein is selected from the group consisting of an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, a dual variable domain immunoglobulin, and a bispecific antibody.

39. The antibody construct according to any on of the embodiments 37 and 38, wherein said binding protein comprises a heavy chain immunoglobulin constant domain selected from the group consisting of a human IgM constant domain, a human IgG1 constant domain, a human IgG2 constant domain, a human IgG3 constant domain, a human IgG4 constant domain, a human IgE constant domain, a human IgD constant domain, a human IgA1 constant domain, a human IgA2 constant domain, a human IgY constant domain and corresponding mutated domains.

40. The antibody construct according to any on of the embodiments 37 to 39, comprising an immunoglobulin constant domain having an amino acid sequence selected from the group consisting of: SEQ ID NOs: 25, 41, 42, and 26.

41. An antibody conjugate comprising an antibody construct described in any one of embodiments 37 to 40, said antibody conjugate further comprising an agent selected from the group consisting of: an immunoadhesion molecule, an imaging agent, a therapeutic agent, and a cytotoxic agent.

42. The antibody conjugate according to embodiment 41, wherein said agent is an imaging agent selected from the group consisting of a radiolabel, an enzyme, a fluorescent label, a luminescent label, a bioluminescent label, a magnetic label, and biotin.

43. The antibody conjugate according to embodiment 42, wherein said imaging agent is a radiolabel selected from the group consisting of: $^{3}H$, $^{14}C$, $^{35}S$, $^{90}Y$, $^{99}Tc$, $^{111}In$, $^{125}I$, $^{131}I$, $^{177}Lu$, $^{166}Ho$, and $^{153}Sm$.

44. The antibody conjugate according to embodiment 41, wherein said agent is a therapeutic or cytotoxic agent selected from the group consisting of: an anti-metabolite, an alkylating agent, an antibiotic, a growth factor, a cytokine, an anti-angiogenic agent, an anti-mitotic agent, an anthracycline, toxin, and an apoptotic agent.

45. The antibody construct according to any on of the embodiments 37 to 40, wherein said binding protein possesses a human glycosylation pattern.

46. The antibody conjugate according to any on of the embodiments 41 to 45, wherein said binding protein possesses a human glycosylation pattern.

47. The binding protein according to any one of the embodiments 1 to 36, wherein said binding protein exists as a crystal.

48. The antibody construct according to any one of the embodiments 37 to 40, wherein said antibody construct exists as a crystal.

49. The antibody conjugate according to any one of the embodiments 41 to 44, wherein said antibody construct exists as a crystal.

50. The binding protein according to embodiment 47, wherein said crystal is a carrier-free pharmaceutical controlled release crystal.

51. The antibody construct according to embodiment 50, wherein said crystal is a carrier-free pharmaceutical controlled release crystal.

52. The antibody conjugate according to embodiment 51, wherein said crystal is a carrier-free pharmaceutical controlled release crystal.

53. The binding protein according to embodiment 50, wherein said binding protein has a greater half life in vivo than the soluble counterpart of said binding protein.

54. The antibody construct according to embodiment 51, wherein said antibody construct has a greater half life in vivo than the soluble counterpart of said antibody construct.

55. The antibody conjugate according to embodiment 52, wherein said antibody conjugate has a greater half life in vivo than the soluble counterpart of said antibody conjugate.

56. The binding protein according to embodiment 53, wherein said binding protein retains biological activity.

57. The antibody construct according to embodiment 54, wherein said antibody construct retains biological activity.

58. The antibody conjugate according to embodiment 55, wherein said antibody conjugate retains biological activity.

59. An isolated nucleic acid encoding a binding protein amino acid sequence of any one of embodiments 1-36.

60. An isolated nucleic acid encoding an antibody construct amino acid sequence of any one of embodiments 37-40.

61. An isolated nucleic acid encoding an antibody conjugate amino acid sequence of any one of embodiments 41-44.

62. A vector comprising an isolated nucleic acid according to any one of embodiments 59 to 61.

63. The vector of embodiment 62 wherein said vector is selected from the group consisting of pcDNA, pTT, pTT3, pEFBOS, pBV, pJV, pHybE, and pBJ.

64. A host cell comprising a vector according to any one of embodiments 62 and 63.

65. The host cell according to embodiment 64, wherein said host cell is a prokaryotic cell.

66. The host cell according to embodiment 65, wherein said host cell is *E. coli*.

67. The host cell according to embodiment 66, wherein said host cell is a eukaryotic cell.

68. The host cell according to embodiment 67, wherein said eukaryotic cell is selected from the group consisting of protist cell, animal cell, plant cell and fungal cell.

69. The host cell according to embodiment 68, wherein said eukaryotic cell is an animal cell selected from the group consisting of: a mammalian cell, an avian cell, and an insect cell.

70. The host cell according to embodiment 69, wherein said host cell is selected from the group consisting of: HEK Cells, CHO cells COS cells and yeast cells.

71. The host cell according to embodiment 70, wherein said yeast cell is *Saccharomyces cerevisiae*.

72. The host cell according to embodiment 70, wherein said host cell is an insect Sf9 cell.

73. A method of producing a protein capable of binding RAGE, comprising culturing a host cell of any one of embodiments 64 to 72 in culture medium under conditions sufficient to produce a binding protein capable of binding RAGE.

74. A protein produced according to the method of embodiment 73.

75. A composition for the release of a binding protein said composition comprising
(a) a formulation, wherein said formulation comprises a crystallized product protein according to any one of embodiments 47 to 52, and an ingredient; and
(b) at least one polymeric carrier.

76. The composition according to embodiment 75, wherein said polymeric carrier is a polymer selected from one or more of the group consisting of: poly(acrylic acid), poly(cyanoacrylates), poly(amino acids), poly(anhydrides), poly(depsipeptide), poly(esters), poly(lactic acid), poly(lactic-co-glycolic acid) or PLGA, poly(b-hydroxybutryate), poly(caprolactone), poly(dioxanone); poly(ethylene glycol), poly((hydroxypropyl) methacrylamide, poly[(organo) phosphazene], poly(ortho esters), poly(vinyl alcohol), poly(vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polyeaccharides, blends and copolymers thereof.

77. The composition according to embodiment 75, wherein said ingredient is selected from the group consisting of albumin, sucrose, trehalose, lactitol, gelatin, hydroxypropyl-β-cyclodextrin, methoxypolyethylene glycol and polyethylene glycol.

78. A method for treating a mammal comprising the step of administering to the mammal an effective amount of the composition according to any one of the embodiments 75 and 76.

79. A pharmaceutical composition comprising the product of any one of embodiments 1 to 61, and a pharmaceutically acceptable carrier.

80. The pharmaceutical composition of embodiment 79, wherein said pharmaceutically acceptable carrier functions as adjuvant useful to increase the absorption, or dispersion of said binding protein.

81. The pharmaceutical composition of embodiment 80, wherein said adjuvant is hyaluronidase.

82. The pharmaceutical composition of embodiment 81 further comprising at least one additional therapeutic agent for treating a disorder in which RAGE activity is detrimental.

83. The pharmaceutical composition of embodiment 82, wherein said additional agent is selected from the group consisting of: therapeutic agent, imaging agent, cytotoxic agent, angiogenesis inhibitors; kinase inhibitors; co-stimulation molecule blockers; adhesion molecule blockers; anti-cytokine antibody or functional fragment thereof; methotrexate; cyclosporin; rapamycin; FK506; detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist. Further examples are: Dimebon, anti-Aβ-antibodies, beta-secretase inhibitors, tau-modulators, cognition enhancers like e.g. 5-HT6 antagonists, cholesterinase inhibitor (e.g., tactrine, donepezil, rivastigmine or galantamine), a partial NMDA receptor blocker (e.g., memantine), a glycosaminoglycan mimetic (e.g., Alzhemed), an inhibitor or allosteric modulator of gamma secretase (e.g., R-flurbiprofen), a luteinizing hormone blockade gonadotropin releasing hormone agonist (e.g., leuprorelin), a serotinin 5-HT1A receptor antagonist, a chelatin agent, a neuronal selective L-type calcium channel blocker, an immunomodulator, an amyloid fibrillogenesis inhibitor or amyloid protein deposition inhibitor (e.g., M266), another antibody (e.g., bapineuzumab), a 5-HT1a receptor antagonist, a PDE4 inhibitor, a histamine agonist, a receptor protein for advanced glycation end products, a PARP stimulator, a serotonin 6 receptor antagonist, a 5-HT4 receptor agonist, a human steroid, a glucose uptake stimulant which enhanced neuronal metabolism, a selective CB1 antagonist, a partial agonist at benzodiazepine receptors, an amyloid beta production antagonist or inhibitor, an amyloid beta deposition inhibitor, a NNR alpha-7 partial antagonist, a therapeutic targeting PDE4, a RNA translation inhibitor, a muscarinic agonist, a nerve growth factor receptor agonist, a NGF receptor agonist and a gene therapy modulator.

84. A method for reducing human RAGE activity comprising contacting human RAGE with the product of any one of embodiments 1 to 61 such that human RAGE activity is reduced.

85. A method for decreasing hRAGE binding to at least one ligand selected from Aβ peptides, globulomers, S100b and Amphoterin in a subject in need thereof, comprising the step of administering to the subject a product of any one of embodiments 1 to 61.

86. A method of treating a subject for a disorder associated with RAGE activity comprising the step of administering alone or in combination with other therapeutic agents a product of any one of embodiments 1 to 61.

87. A method of embodiment 86 where an RAGE therapeutic antibody is delivered systemically with effects in the peripheral nervous system.

88. A method for reducing RAGE activity in a subject suffering from a disorder in which RAGE activity is detrimental, comprising administering to the subject a product of any one of embodiments 1 to 61, alone or in combination with other therapeutic agents.

89. The method of embodiment 88, wherein the disorder comprises neurological diseases selected from the group comprising Amytropic Lateral Sclerosis, Brachial Plexus Injury, Brain Injury, including traumatic brain injury, Cerebral Palsy, Friedrich's Ataxia, Guillain Barre, Leukodystrophies, Multiple Sclerosis, Post Polio, Spina Bifida, Spinal Cord Injury, Spinal Muscle Atrophy, Spinal Tumors, Stroke, Transverse Myelitits, dementia, senile dementia, mild cognitive impairment, Alzheimer-related dementia, Huntington's chorea, tardive dyskinesia, hyperkinesias, manias, Morbus Parkinson, steel-Richard syndrome, Down's syndrome, myasthenia gravis, nerve trauma, vascular amyloidosis, cerebral hemorrhage I with amyloidosis, brain inflammation, Friedrich's ataxia, acute confusion disorder, amyotrophic lateral sclerosis, glaucoma, Alzheimer's disease, diabetic nephropathy, sepsis, rheumatoid arthritis and related inflammatory diseases; Diabetes and resulting complications like diabetic retinopathy, nephropathy, neuropathy, vascular complications; atherosclerotic complications, pulmonary fibrosis, Cancer especially melanomas, other amyloidoses, and chronic pain.

90. An isolated CDR of a binding protein as defined in any one of the embodiments 1 to 36.

91. An isolated binding protein that specifically interacts to at least one epitope of a Receptor of Advanced Glycation Endproducts (RAGE) protein.

92. The isolated binding protein of embodiment 91, wherein the isolated protein is a monoclonal antibody or antigen binding fragment thereof.

93. The monoclonal antibody or antigen binding fragment according to embodiment 92, which comprises a VH and a VL domain.

94. The monoclonal antibody according to embodiment 92 wherein said monoclonal antibody diminishes the ability of RAGE to bind to its ligands.

95. The ligands according to embodiment 94, wherein the ligands comprise Aβ peptides, globulomers, S100b and amphoterin.

96. The monoclonal antibody according to embodiment 92 wherein said antibody is capable of blocking the binding of Aβ globulomer to RAGE.

97. The monoclonal antibody or antigen binding fragment thereof according to embodiment 92 wherein the antibody or antigen binding fragment comprises:

a heavy chain variable region having an amino acid sequence selected from the group consisting of SEQ ID NO: 1, SEQ ID NO: 9, and SEQ ID NO: 17;
a light chain variable region having an amino acid sequence selected from the group consisting of SEQ ID NO: 5, SEQ ID NO: 13, and SEQ ID NO: 21;
a human Immunoglobulin gamma 1 heavy chain constant region with amino acid sequence SEQ ID NO: 25; and
a human Immunoglobulin kappa light chain constant region with amino acid sequence SEQ ID NO: 26.

98. The monoclonal antibody of embodiment 93, wherein the antigen binding domain comprises at least one complementarity determining region (CDR) comprising an amino acid sequence with at least 90% homology with the sequence selected from the group consisting of SEQ ID NOs: 2, 3, 4, 6, 7, 8, 10, 11, 12, 14, 15, 16, 18, 19, and 20.

99. The monoclonal antibody according to embodiment 93 wherein said VH domain comprises a heavy chain variable region having an amino acid sequence that has at least 90% homology with the sequence selected from the group consisting of SEQ ID NO 1, SEQ ID NO 9, and SEQ ID NO 17.

100. The monoclonal antibody according to embodiment 99 wherein said VH domain comprises at least one CDR region comprising an amino acid sequence with at least 90% homology with the sequence selected from the group consisting of SEQ ID NOs: 2, 3, 4, 10, 11, 12, 18, 19, and 20.

101. The monoclonal antibody according to embodiment 100 wherein said VH domain comprises at least three CDR regions selected from the set of SEQ ID NOs: 2, 3, and 4; SEQ ID NOs: 10, 11, and 12; or SEQ ID NOs: 18, 19, and 20.

102. The monoclonal antibody according to embodiment 93 wherein said VL domain comprises a light chain variable region having an amino acid sequence that has at least 90% homology with the sequence selected from the group consisting of SEQ ID NO: 5, SEQ ID NO: 13, and SEQ ID NO: 21.

103. The monoclonal antibody according to embodiment 102 wherein said VL domain comprises at least one CDR region comprising an amino acid sequence with at least 90% homology with the sequence selected from the group consisting of SEQ ID NOs: 6, 7, 8, 14, 15, 16, 22, 23, and 24.

104. The monoclonal antibody according to embodiment 103 wherein said VL domain comprises at least three CDR regions selected from at least one set of SEQ ID NOs: 6, 7, and 8; SEQ ID NOs: 14, 15 and 16; or SEQ ID NOs: 22, 23, and 24.

105. The antibody or antigen-binding fragment of embodiment 92, wherein said antibody or antigen-binding fragment is a mouse antibody, a humanized antibody, a fully human, a chimeric antibody, an antigen-binding fragment of a humanized antibody, or an antigen-binding fragment of a chimeric antibody.

106. The antibody or antigen-binding fragment of embodiment 92, wherein said antibody or antigen-binding fragment is an antigen-binding fragment selected from the group consisting of a Fab fragment, a Fab' fragment, a F(ab')$_2$ fragment and a Fv fragment.

107. A hybridoma cell line that produces a monoclonal antibody or antigen-binding fragment thereof according to embodiment 96.

108. The hybridoma cell line of embodiment 107, wherein the hybridoma is selected from the group consisting of mouse, human, rat, sheep, pig, cattle, goat, and horse hybridoma.

109. A hybridoma cell line that produces a monoclonal antibody, which specifically binds to at least one epitope of a RAGE protein.

110. The hybridoma cell line of embodiment 107, wherein the hybridoma is selected from the group consisting of mouse and human hybridoma.

111. The hybridoma cell line of embodiment 107, wherein the hybridoma is selected from the group consisting of rat, sheep, pig, cattle, goat, and horse hybridoma.

112. A vector comprising the isolated nucleic acid comprising the isolated nucleic acid that encodes any of the amino acid sequences of embodiment 97, wherein said vector is selected from the group consisting of pcDNA; pTT; pTT3; pEFBOS; pBV; pJV; and pBJ.

113. A host cell transformed with the vector according to embodiment 112, wherein the host cell is selected from the group consisting of protist cell, animal cell, plant cell and fungal cell.

114. The host cell of embodiment 113 wherein the animal cell is a mammalian cell selected from the group comprising HEK293, CHO and COS.

115. A method of producing the isolated binding protein according to embodiment 91, comprising culturing a host cell in a culture medium under conditions sufficient to produce the binding protein, collecting the culture media, and purifying the produced isolated binding protein.

116. A pharmaceutical composition comprising the monoclonal antibody or antigen-binding portion according to any of embodiments 99 or 102 and a pharmaceutically acceptable carrier.

117. A method of treating a disease or disorder comprising administering the monoclonal antibodies of embodiments 99 or 102 that bind to the C2-domain in RAGE.

118. The method of embodiment 117 wherein the disorder comprises neurological diseases selected from the group consisting of: Amytropic Lateral Sclerosis, Brachial Plexus Injury, Brain Injury, including traumatic brain injury, Cerebral Palsy, Friedrich's Ataxia, Guillain Barre, Leukodystrophies, Multiple Sclerosis, Post Polio, Spina Bifida, Spinal Cord Injury, Spinal Muscle Atrophy, Spinal Tumors, Stroke, Transverse Myelitits, dementia, senile dementia, mild cognitive impairment, Alzheimer-related dementia, Huntington's chorea, tardive dyskinesia, hyperkinesias, manias, Morbus Parkinson, steel-Richard syndrome, Down's syndrome, myasthenia gravis, nerve trauma, vascular amyloidosis, cerebral hemorrhage I with amyloidosis, brain inflammation, Friedrich's ataxia, acute confusion disorder, amyotrophic lateral sclerosis, glaucoma, Alzheimer's disease, diabetic nephropathy, sepsis, rheumatoid arthritis and related inflammatory diseases.

119. The antibody of embodiment 105, comprising at least one VH region comprising an amino acid sequence selected from the group consisting of: SEQ ID NOs: 56 and 57.

120. The antibody of embodiment 105, comprising at least one VL region comprising an amino acid sequence selected from the group consisting of: SEQ ID NO: 58 and 59.

121. The antibody of embodiment 119 or 120, additionally modified by 1 to 10 mutations in an VH or VL sequence.

122. The antibody of embodiment 121, wherein the mutations are selected from the group consisting of: framework back mutations and mutations of Vernier and VH/VL interfacing residues.

123. An antibody or binding protein of one of the preceding embodiments which inhibits the binding of RAGE to an HMGB1-CpG DNA complex; or an antibody or binding protein of one of the preceding embodiments which does not inhibit the binding of RAGE to an HMGB1-CpG DNA complex.

124. A method for treating pain, comprising the step of administering to a mammal in need thereof an effective amount of a composition comprising an isolated binding protein, antibody construct, antibody conjugate or antibody as defined in any one of the above embodiments 1 to 58, 91 to 94, 96 to 106 or 119 to 123.

125. A method of embodiment 124, comprising the step of administering to a mammal in need thereof an effective amount of a composition comprising a monoclonal antibody comprising an antigen binding domain, said antibody capable of binding an epitope of a human RAGE molecule, said antigen binding domain comprising at least one CDR comprising an amino acid sequence selected from:
  a) the CDR-H3 group of amino acid sequences selected from the group consisting of SEQ ID NOs: 4, 12 and 20; modified CDR amino acid sequences having a sequence identity of at least 50% to one of said sequences; and/or
  b) the CDR-L3 group of amino acid sequences selected from the group consisting of SEQ ID NOs: 8, 16 and 24; and modified CDR amino acid sequences having a sequence identity of at least 50% to one of said sequences.

126. The method according to embodiment 125, wherein the antibody construct, antibody conjugate or antibody further comprises at least one CDR comprising an amino acid sequence selected from the CDR-H1 group consisting of SEQ ID NOs: 2, 10 and 18; or selected from the CDR-H2 group consisting of SEQ ID NOs: 3, 11 and 19; or selected from the CDR-L1 group consisting of SEQ ID NOs: 6, 14, 22; or selected from the CDR-L2 group consisting of SEQ ID NOs: 7, 15, and 23; and modified CDR amino acid sequences having a sequence identity of at least 50% to one of said sequences.

127. The method according to embodiment 126, wherein the antibody construct, antibody conjugate or antibody further comprises at least 3 CDRs which are selected from a variable domain CDR set comprising:

| VH 11E6 set | | |
| --- | --- | --- |
| VH 11E6 CDR-H1 | Residues 31-35 of SEQ ID NO: 9 | SEQ ID NO: 10 |
| VH 11E6 CDR-H2 | Residues 50-66 of SEQ ID NO: 9 | SEQ ID NO: 11 |
| VH 11E6 CDR-H3 | Residues 99-109 of SEQ ID NO: 9 | SEQ ID NO: 12 |
| VL 11E6 set | | |
| VL 11E6 CDR-L1 | Residues 24-34 of SEQ ID NO: 13 | SEQ ID NO: 14 |
| VL 11E6 CDR-L2 | Residues 50-56 of SEQ ID NO: 13 | SEQ ID NO: 15 |
| VL 11E6 CDR-L3 | Residues 89-97 of SEQ ID NO: 13 | SEQ ID NO: 16 |
| VH 4E5 set | | |
| VH 4E5 CDR-H1 | Residues 31-35 of SEQ ID NO: 17 | SEQ ID NO: 18 |
| VH 4E5 CDR-H2 | Residues 50-66 of SEQ ID NO: 17 | SEQ ID NO: 19 |
| VH 4E5 CDR-H3 | Residues 99-109 of SEQ ID NO: 17 | SEQ ID NO: 20 |

-continued

| VL 4E5 set | | |
|---|---|---|
| VL 4E5 CDR-L1 | Residues 24-34 of SEQ ID NO: 21 | SEQ ID NO: 22 |
| VL 4E5 CDR-L2 | Residues 50-56 of SEQ ID NO: 21 | SEQ ID NO: 23 |
| VL 4E5 CDR-L3 | Residues 89-97 of SEQ ID NO: 21 | SEQ ID NO: 24 | or a variable domain set wherein at least one of said 3 CDRs is a modified CDR amino acid sequence having a sequence identity of at least 50% to the parent sequence.

128. The method according to embodiment 127, wherein said at least two variable domain CDR sets are from at least one of the below sets:
  (a) VH 4E5 set and VL 4E5 set; or
  (b) VH 11E6 set and VL 11E6 set.

129. The method according to embodiment 125, wherein the antibody construct, antibody conjugate or antibody further comprises a human acceptor framework.

130. The method of embodiment 125, wherein the antibody construct, antibody conjugate or antibody comprises at least one heavy chain variable domain selected from the group consisting of: SEQ ID NOs: 56 and 57; and/or at least one light chain variable domain selected from the group consisting of: SEQ ID NOs: 58 and 59.

131. The method according to embodiment 130, wherein said binding protein comprises (a) at least one heavy chain sequence mutation selected from the group consisting of: 1, 2, 68, 70, 72, 76, 85, 89 and 95; (b) at least one light chain sequence mutation selected from the group consisting of: 11, 13, 43, 49, 58, 70 and 87; or (c) combinations of (a) and (b).

132. The method of embodiment 125, wherein the antibody construct, antibody conjugate or antibody comprises (a) at least one framework mutation at a position selected from the group consisting of: 62, 67, 68 and 69; (b) at least one light chain framework mutation at a position selected from the group consisting of: 63, 64, 65 and 66; or (c) combinations of (a) and (b).

133. The method of embodiment 125, wherein the antibody construct, antibody conjugate or antibody is selected from the group consisting of antibodies 11E6 and 4E5.

134. The method of embodiment 125, wherein the composition comprises a formulation, wherein said formulation comprises the antibody of embodiment 1 in crystallized form as an ingredient; and at least one polymeric carrier.

135. The method of embodiment 134, wherein the composition comprises 11E6.

136. The method of one of the embodiments 124 to 135, wherein said pain is selected from the group consisting of chronic and acute pain.

137. The method of embodiment 136, wherein said pain is selected from the group consisting of peripheral or central neuropathic pain, nociceptive pain (like superficial somatic pain, deep somatic pain and visceral pain); and psychogenic pain.

138. The method of embodiment 125, wherein said pain is inflammatory pain.

139. A binding protein, antibody construct, antibody conjugate or antibody as defined in any one of the above embodiments 1 to 58, 91 to 94, 96 to 106 or 119 to 123 for use in treating pain.

140. The binding protein, antibody construct, antibody conjugate or antibody for the use of embodiment 139, wherein said pain is selected from the group consisting of chronic or acute pain.

141. The binding protein antibody construct, antibody conjugate or antibody for the use of embodiment 140, wherein said pain is selected from the group consisting of peripheral or central neuropathic pain, nociceptive pain (like superficial somatic pain, deep somatic pain and visceral pain); and psychogenic pain.

142. The binding protein, antibody construct, antibody conjugate or antibody for the use of embodiment 141, wherein said pain is inflammatory pain.

143. The use of a binding protein, antibody construct, antibody conjugate or antibody as defined in any one of the above embodiments 1 to 58, 91 to 94, 96 to 106 or 119 to 123 for preparing a pharmaceutical composition for treating pain.

144. The use of embodiment 143, wherein said pain is selected from the group consisting of chronic and acute pain.

145. The use of embodiment 144, wherein said pain is selected from the group consisting of peripheral or central neuropathic pain, nociceptive pain (like superficial somatic pain, deep somatic pain and visceral pain); and psychogenic pain.

146. The binding protein, antibody construct, antibody conjugate or antibody of embodiment 125, wherein said pain is inflammatory pain.

147. The method as in embodiments 124-135, wherein said pain is neuropathic pain.

148. The method as in embodiment 147, wherein said neuropathic pain is peripheral or central neuropathic pain.

149. The method as in embodiments 143, wherein said pain is neuropathic pain.

150. The method as in embodiment 149, wherein said neuropathic pain is peripheral or central neuropathic pain.

3. Generation of Anti-RAGE Antibodies 3.1. General

Antibodies of the application can be generated by immunization of a suitable host (e.g., vertebrates, including humans, mice, rats, sheep, goats, pigs, cattle, horses, reptiles, fishes, amphibians, and in eggs of birds, reptiles and fish). To generate the antibodies of the present application, the host is immunized with an immunogenic RAGE polypeptide or fragment thereof of the invention. The term "immunization" refers herein to the process of presenting an antigen to an immune repertoire whether that repertoire exists in a natural genetically unaltered organism, or a transgenic organism, including those modified to display an artificial human immune repertoire. Similarly, an "immunogenic preparation" is a formulation of antigen that contains adjuvants or other additives that would enhance the immunogenicity of the antigen.

Immunization of animals may be done by any method known in the art. See, e.g., Harlow and Lane, Antibodies: A Laboratory Manual, New York: Cold Spring Harbor Press, 1990. Methods for immunizing non-human animals such as mice, rats, sheep, goats, pigs, cattle and horses are well known in the art. See, e.g., Harlow and Lane (supra) and U.S. Pat. No. 5,994,619. In a particular embodiment, the RAGE antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Particularly, if a polypeptide is being administered, the immunization schedule will involve two or more administrations of the polypeptide, spread out over several weeks.

It is contemplated that the animal host is immunized with the antigen associated with the cell membrane of an intact or disrupted cell and antibodies of the present application are identified by binding to an immunogenic polypeptide of the invention. After immunization of the animal host with the antigen, antibodies may be obtained from the animal. The antibody-containing serum is obtained from the animal by bleeding or sacrificing the animal. The serum may be used as it is obtained from the animal, an immunoglobulin fraction may be obtained from the serum, or the antibodies may be purified from the serum. Serum or immunoglobulins obtained in this manner are polyclonal, thus having a heterogeneous array of properties.

3.2 Anti-RAGE Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, particularly, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. Briefly, mice can be immunized with an RAGE antigen. In a particular embodiment, the RAGE antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Particularly, if a polypeptide is being administered, the immunization schedule will involve two or more administrations of the polypeptide, spread out over several weeks.

Once an immune response is detected, e.g., antibodies specific for the antigen RAGE are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding RAGE. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a particular embodiment, the myeloma cells do not secrete immunoglobulin polypeptides (a non-secretory cell line). After fusion and antibiotic selection, the hybridomas are screened using RAGE or a portion thereof, or a cell expressing RAGE. In a particular embodiment, the initial screening is performed using an enzyme-linked immunoassay (ELISA) or a radioimmunoassay (RIA), particularly an ELISA. An example of ELISA screening is provided in WO 00/37504, herein incorporated by reference.

Anti-RAGE antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a particular embodiment, the hybridomas are mouse hybridomas, as described above. In another particular embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-RAGE antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain.

3.3 Anti-RAGE Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052, WO 92/02551 and Babcock, J. S. et al. (1996) *Proc. Natl. Acad. Sci. USA* 93:7843-7848. In this method, single cells secreting antibodies of interest, e.g., lymphocytes derived from any one of the immunized animals described above, are screened using an antigen-specific hemolytic plaque assay, wherein the antigen RAGE, a subunit of RAGE, or a fragment thereof, is coupled to sheep red blood cells using a linker, such as biotin, and used to identify single cells that secrete antibodies with specificity for RAGE. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to RAGE. The amplified immunoglobulin sequences further can be manipulated in vitro, such as by in vitro affinity maturation methods such as those described in WO 97/29131 and PCT Publication WO 00/56772.

3.4 Anti-RAGE Monoclonal Antibodies Using Transgenic Animals

In another embodiment of the instant invention, antibodies are produced by immunizing a non-human animal comprising some, or all, of the human immunoglobulin locus with an RAGE antigen. In a particular embodiment, the non-human animal is a XENOMOUSE transgenic mouse, an engineered mouse strain that comprises large fragments of the human immunoglobulin loci and is deficient in mouse antibody production. See, e.g., Green et al. *Nature Genetics* 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00/09560, published Feb. 24, 2000 and WO 00/037504, published Jun. 29, 2000. The XENOMOUSE transgenic mouse produces an adult-like human repertoire of fully human antibodies, and generates antigen-specific human Mabs. The XENOMOUSE transgenic mouse contains approximately 80% of the human antibody repertoire through introduction of megabase sized, germline configuration YAC fragments of the human heavy chain loci and x light chain loci. See Mendez et al., *Nature Genetics* 15:146-156 (1997), Green and Jakobovits *J. Exp. Med.* 188:483-495 (1998), the disclosures of which are hereby incorporated by reference.

3.5 Anti-RAGE Monoclonal Antibodies Using Recombinant Antibody Libraries

In vitro methods also can be used to make the antibodies of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, US patent application publication 2003/0186374, and PCT Publication No. WO 97/29131, the contents of each of which are incorporated herein by reference.

The recombinant antibody library may be from a subject immunized with RAGE, or a portion of RAGE. Alternatively, the recombinant antibody library may be from a naïve subject, i.e., one who has not been immunized with RAGE, such as a human antibody library from a human subject who has not been immunized with human RAGE. Antibodies of the invention are selected by screening the recombinant antibody library with the peptide comprising human RAGE to thereby select those antibodies that recognize RAGE. Methods for conducting such screening and selection are well known in the art, such as described in the references in the preceding paragraph. To select antibodies of the invention having particular binding affinities for hRAGE, such as those that dissociate from human RAGE with a particular $k_{off}$ rate constant, the art-known method of surface plasmon resonance can be used to select antibodies having the desired $K_{off}$ rate constant. To select antibodies of the invention having a particular neutralizing activity for hRAGE, such as those with a particular an $IC_{50}$, standard methods known in the art for assessing the inhibition of hRAGE activity may be used.

In one aspect, the invention pertains to an isolated antibody, or an antigen-binding portion thereof, that binds human RAGE. Particularly, the antibody is a neutralizing antibody. In various embodiments, the antibody is a recombinant antibody or a monoclonal antibody.

For example, the antibodies of the present invention can also be generated using various phage display methods known in the art. In phage display methods, functional antibody domains are displayed on the surface of phage particles, which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., Science 240:1041-1043 (1988) (said references incorporated by reference in their entireties). Examples of techniques, which can be used to produce single-chain Fvs and antibodies include those described in U.S. Pat. Nos. 4,946,778 and 5,258,498; Huston et al., *Methods in*

*Enzymology* 203:46-88 (1991); Shu et al., *PNAS* 90:7995-7999 (1993); and Skerra et al., *Science* 240:1038-1040 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed Wittrup, et al. U.S. Pat. No. 6,699,658 incorporated herein by reference.

4. Production of Particular Recombinant RAGE Antibodies of the Invention

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Particular mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P.A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, in particular, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a particular system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

4.1 Anti RAGE Antibodies

Table 4 is a list of amino acid sequences of VH and VL regions of particular anti-hRAGE antibodies of the invention.

TABLE 4A

List of Amino Acid Sequences of VH and VL regions of anti-huRAGE antibodies

| Seq. ID No. | Protein Region | | Sequence<br>12345678901234567890123456789 01 |
|---|---|---|---|
| 9 | VH 11E6 | | QIQLVQSGPELKKPGETVKISCKASGYTFTN<br>FGMNWVKQAPGKGLKWMGYINTNTGESIYSE<br>EFKGRFAFSLETSASTAYLQINNLKNEDTAT<br>YFCARSRMVTAYGMDYWGQGTSVTVSS |
| | VH 11E6<br>CDR-H1 | Residues<br>31-35 of<br>SEQ ID NO: 9 | NFGMN |
| | VH 11E6<br>CDR-H2 | Residues<br>50-66 of<br>SEQ ID NO: 9 | YINTNTGESIYSEEFKG |
| | VH 11E6<br>CDR-H3 | Residues<br>99-109 of<br>SEQ ID NO: 9 | SRMVTAYGMDY |
| 13 | VL<br>11E6 | | DIVMTQSQKFMSTSVGDRVSITCKASQNVGT<br>AVAWYQQRPGQSPKLLIFSASNRYTGVPDRF<br>TGSGSGTDFTLTLSNMPEDLADYFCQQYSS<br>YPLTFGVGTKLELKR |
| | VL 11E6<br>CDR-L1 | Residues<br>24-34 of<br>SEQ ID NO: 13 | KASQNVGTAVA |
| | VL 11E6<br>CDR-L2 | Residues<br>50-56 of<br>SEQ ID NO: 13 | SASNRYT |
| | VL 11E6<br>CDR-L3 | Residues<br>89-97 of<br>SEQ ID NO: 13 | QQYSSYPLT |
| 17 | VH 4E5 | | QVQLQQSGAELVRPGTSVKVSCKASGYAFNN<br>YLIEWIKQRPGQGLEWIGVINPGSGGTNHNE<br>KFKVKATLTADKSSSTAYIQLSSLTSDDSAV<br>YFCARSAGTARARFAYWGQGTLVTVSA |
| | VH 4E5<br>CDR-H1 | Residues<br>31-35 of<br>SEQ ID NO: 17 | NYLIE |
| | VH 4E5<br>CDR-H2 | Residues<br>50-66 of<br>SEQ ID NO: 17 | VINPGSGGTNHNEKFKV |
| | VH 4E5<br>CDR-H3 | Residues<br>99-109 of<br>SEQ ID NO: 17 | SAGTARARFAY |
| 21 | VL 4E5 | | DIQMTQSPSSLSASLGERVSLTCRASQDIGS<br>SLNWLQQEPDGTIKRLIYATSSLDSGVPKRF<br>SGSRSGSDYSLTISSLESEDFVDYYCLQYAS<br>FPFTFGSGTKLEIKR |
| | VL 4E5<br>CDR-L1 | Residues<br>24-34 of<br>SEQ ID NO: 21 | RASQDIGSSLN |
| | VL 4E5<br>CDR-L2 | Residues<br>50-56 of<br>SEQ ID NO: 21 | ATSSLDS |
| | VL 4E5<br>CDR-L3 | Residues<br>89-97 of<br>SEQ ID NO: 21 | LQYASFPFT |

The foregoing isolated anti-RAGE antibody CDR sequences establish a novel family of RAGE binding proteins, isolated in accordance with this invention. To generate and to select CDR's of the invention having particular RAGE binding and/or neutralizing activity with respect to hRAGE, standard methods known in the art for generating binding proteins of the present invention and assessing the RAGE binding and/or neutralizing characteristics of those binding protein may be used, including but not limited to those specifically described herein.

The below humanized antibody 7F9 could also be useful as an anti-RAGE antibody.

TABLE 4B

Sequences for antibody 7F9

| Seq. ID No. | Protein Region | | Sequence 1234567890123456789012345678901 |
|---|---|---|---|
| 1 | VH 7F9* | | EEKLEESGGGLVQLGGSMKISCVASGFTLSN YWMDWVRQSPEKGLEWIAEIRLKSNYYSTHY AESVKGRFSISRDDSKGSVSLQMDNLTAEDT GIYFCARNAYWYFDVWGTGTTVTVSS |
| | VH 7F9 CDR-H1 | Residues 31-35 of SEQ ID NO: 1 | NYWMD |
| | VH 7F9 CDR-H2 | Residues 50-68 of SEQ ID NO: 1 | EIRLKSNYYSTHYAESVKG |
| | VH 7F9 CDR-H3 | Residues 101-108 of SEQ ID NO: 1 | NAYWYFDV |
| 5 | VL 7F9 | | DIVMTQSHKFMSTSVGDRVSATCKASQDVGT SVAWYQQKLGQSPKLLIYWTSTRHTGVPDRF TGSGSGTDFTLTISNVQSEDLADYFCQQYNN YPLTFGDGTKLELKR |
| | VL 7F9 CDR-L1 | Residues 24-34 of SEQ ID NO: 5 | KASQDVGTSVA |
| | VL 7F9 CDR-L2 | Residues 50-56 of SEQ ID NO: 5 | WTSTRHT |
| | VL 7F9 CDR-L3 | Residues 89-97 of SEQ ID NO: 5 | QQYNNYPLT |

4.2 Anti RAGE Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science* 229:1202 (1985); Oi et al., *BioTechniques* 4:214 (1986); Gillies et al., (1989) *J. Immunol. Methods* 125:191-202; U.S. Pat. Nos. 5,807,715; 4,816,567; and 4,816,397, which are incorporated herein by reference in their entireties. In addition, techniques developed for the production of "chimeric antibodies" (Morrison et al., 1984, *Proc. Natl. Acad. Sci.* 81:851-855; Neuberger et al., 1984, *Nature* 312:604-608; Takeda et al., 1985, *Nature* 314:452-454 which are incorporated herein by reference in their entireties) by splicing genes from a mouse antibody molecule of appropriate antigen specificity together with genes from a human antibody molecule of appropriate biological activity can be used.

In one embodiment, the chimeric antibodies of the invention are produced by replacing the heavy chain constant region of the murine monoclonal anti human RAGE antibodies described herein with a human IgG1 constant region.

4.3 Anti RAGE CDR Grafted Antibodies

CDR-grafted antibodies of the invention comprise heavy and light chain variable region sequences from a human antibody wherein one or more of the CDR regions of $V_H$ and/or $V_L$ are replaced with CDR sequences of non-human, as for example, murine antibodies of the invention. A framework sequence from any human antibody may serve as the template for CDR grafting. However, straight chain replacement onto such a framework often leads to some loss of binding affinity to the antigen. The more homologous a human antibody is to the original murine antibody, the less likely the possibility that combining the murine CDRs with the human framework will introduce distortions in the CDRs that could reduce affinity. Therefore, it is preferable that the human variable framework that is chosen to replace the murine variable framework apart from the CDRs have at least a 65% sequence identity with the murine antibody variable region framework. It is more preferable that the human and murine variable regions apart from the CDRs have at least 70% sequence identify. It is even more preferable that the human and murine variable regions apart from the CDRs have at least 75% sequence identity. It is most preferable that the human and murine variable regions apart from the CDRs have at least 80% sequence identity. Methods for producing CDR-grafted antibodies are known in the art (Jones et al., *Nature* 321:522-525 (1986); U.S. Pat. No. 5,225,539).

In a specific embodiment the invention provides CDR grafted antibodies with $V_H$ and/or $V_L$ chains as described in Table 5.

TABLE 5

CDR Grafted antibodies

| SEQ ID NO | Protein region | Sequence 123456789012345678901234567890 |
|---|---|---|
| 56 | VH 11E6.1-GL | QVQLVQSGSELKKPGASVKVSCKASGYTFT |
| (43) | (VH7-4.1/JH6 FR1) | NFGMNWVRQAPGQGLEWMGYINTNTGESIY |
| (44) | (VH7-4.1/JH6 FR2) | SEEFKGRFVFSLDTSVSTAYLQICSLKAED |

TABLE 5-continued

CDR Grafted antibodies

| SEQ ID NO | Protein region | Sequence 12345678901234567890123456789 0 |
|---|---|---|
| (45) | (VH7-4.1/JH6 FR3) | TAVYYCARSRMVTAYGMDYWGQGTTVTVSS |
| (46) | (VH7-4.1/JH6 FR4) | |
| 57 | VH 11E6.2-GL | QVQLVQSGAEVKKPGASVKVSCKASGYTFT |
| (47) | (VH1-2/JH6 FR1) | NFGMNWVRQAPGQGLEWMGYINTNTGESIY |
| (44) | (VH1-2/JH6 FR2) | SEEFKGRVTMTRDTSISTAYMELSRLRSDD |
| (48) | (VH1-2/JH6 FR3) | TAVYYCARSRMVTAYGMDYWGQGTTVTVSS |
| (46) | (VH1-2/JH6 FR4) | |
| 58 | VL 11E6.1-GL | DIQMTQSPSSVSASVGDRVTITCKASQNVG |
| (49) | (1-12/L5/JK2 FR1) | TAVAWYQQKPGKAPKLLIYSASNRYTGVPS |
| (50) | (1-12/L5/JK2 FR2) | RFSGSGSGTDFTLTISSLQPEDFATYYCQQ |
| (51) | (1-12/L5/JK2 FR3) | YSSYPLTFGQGTKLEIKR |
| (52) | (1-12/L5/JK2 FR4) | |
| 59 | VL 11E6.2-GL | EIVMTQSPATLSVSPGERATLSCKASQNVG |
| (53) | (3-15/L2/JK2 FR1) | TAVAWYQQKPGQAPRLLIYSASNRYTGIPA |
| (54) | (3-15/L2/JK2 FR2) | RFSGSGSGTEFTLTISSLQSEDFAVYYCQQ |
| (55) | (3-15/L2/JK2 FR3) | YSSYPLTFGQGTKLEIKR |
| (52) | (3-15/L2/JK2 FR4) | |

CDR sequences derived from mAb 11E6 are stated in bold letters. Reference is also made to the specific framework sequences (FR1 to FR4) by stating the corresponding SEQ ID NOs: (see also Tables 2 and 3).

4.4 Anti RAGE Humanized Antibodies

Humanized antibodies are antibody molecules from non-human species antibody that binds the desired antigen having one or more complementarity determining regions (CDRs) from the non-human species and framework regions from a human immunoglobulin molecule. Known human Ig sequences are disclosed, e.g., www.ncbi.nlm.nih.gov/entrez/query.fcgi; www.atcc.org/phage/hdb.html; www.sciquest.com/; www.abcam.com/; www.antibodyresource.com/onlinecomp.html; www.public.iastate.edu/.about.pedro/research_tools.html; www.mgen.uni-heidelberg.de/SD/IT/IT.html; www.whfreeman.com/immunology/CH-05/kuby05.htm; www.library.thinkquest.org/12429/Immune/Antibody.html; www.hhmi.org/grants/lectures/1996/vlab/; www.path.cam.ac.uk/.about.mrc7/mikeimages.html; www.antibodyresource.com/; mcb.harvard.edu/BioLinks/Immunology.html.www.immunologylink.com/; pathbox.wustl.edu/.about.hcenter/index.-html; www.biotech.ufl.edu/.about.hcl/; www.pebio.com/pa/340913/340913.html-; www.nal.usda.gov/awic/pubs/antibody/; www.m.ehime-u.acjp/.about.yasuhito-/Elisa.html; www.biodesign.com/table.asp; www.icnet.uk/axp/facs/davies/lin-ks.html; www.biotech.ufl.edu/.about.fccl/protocol.html; www.isac-net.org/sites_geo.html; aximtl.imt.uni-marburg.de/.about.rek/AEP-Start.html; baserv.uci.kun.nl/.about.jraats/linksl.html; www.recab.uni-hd.de/immuno.bme.nwu.edu/; www.mrc-cpe.cam.ac.uk/imt-doc/pu-blic/INTRO.html; www.ibt.unam.mx/vir/V_mice.html; imgt.cnusc.fr:8104/; www.biochem.ucl.ac.uk/.about.martin/abs/index.html; antibody.bath.ac.uk/; abgen.cvm.tamu.edu/lab/wwwabgen.html; www.unizh.ch/.about.honegger/AHOsem-inar/Slide01.html; www.cryst.bbk.ac.uk/.about.ubcg07s/; www.nimr.mrc.ac.uk/CC/ccaewg/ccaewg.htm; www.path.cam.ac.uk/.about.mrc7/humanisation/TAHHP.html; www.ibt.unam.mx/vir/structure/stat_aim.html; www.biosci.missouri.edu/smithgp/index.html; www.cryst.bioc.cam.ac.uk/.abo-ut.fmolina/Web-pages/Pept/spottech.html; www.jerini.de/froducts.htm; www.patents.ibm.com/ibm.html.Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, particularly improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO 90/14443, WO 90/14424, WO 90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, each entirely incorporated herein by reference, included references cited therein.

5. Further Embodiments of Antibodies of the Invention

5.1 Fusion Antibodies and Immunoadhesins

The present application also describes a fusion antibody or immunoadhesin that may be made which comprises all or a portion of a RAGE antibody of the present application linked to another polypeptide. In some embodiments, only the variable region of the RAGE antibody is linked to the polypeptide. In other embodiments, the VH domain of a RAGE antibody of this application is linked to a first polypeptide, while the VL domain of the antibody is linked to a second polypeptide that associates with the first polypeptide in a manner that permits the VH and VL domains to interact with one another to form an antibody binding site. In other embodiments, the VH domain is separated from the VL domain by a linker that permits the VH and VL domains to interact with one another (see below under Single Chain Antibodies). The VH-linker-VL antibody is then linked to a polypeptide of interest. The fusion antibody is useful to directing a polypeptide to a cell or tissue that expresses a RAGE. The polypeptide of interest may be a therapeutic agent, such as a toxin, or may be a diagnostic agent, such as an enzyme; that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

One embodiment provides a labelled binding protein wherein an antibody or antibody portion of the present application is derivatized or linked to another functional molecule (e.g., another peptide or protein). For example, a labelled binding protein of the present application can be derived by functionally linking an antibody or antibody portion of the present application (by chemical coupling, genetic fusion, noncovalent association or otherwise) to one or more other molecular entities, such as a nucleic acid, another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

Useful detectable agents with which an antibody or antibody portion of the present application may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a nucleic acid, biotin, and detected through indirect measurement of avidin or streptavidin binding.

5.2 Single Chain Antibodies

The present application includes a single chain antibody (scFv) that binds an immunogenic RAGE of the invention. To produce the scFv, VH- and V-encoding DNA is operatively linked to DNA encoding a flexible linker, e.g., encoding the amino acid sequence (Gly4-Ser), such that the VH and VL sequences can be expressed as a contiguous single-chain protein, with the VL and VH regions joined by the flexible linker (see e.g., Bird et al. (1988) *Science* 242:423-42 6; Huston et al. (1988) *Proc. Natl. Acad. Sci. USA* 85: 5879-5883; McCafferty et al., 30 *Nature* (1990) 34 8: 552-554). The single chain antibody may be monovalent, if only a single VH and VL are used, bivalent, if two VH and VL are used, or polyvalent, if more than two VH and VL are used. Two of said scFv fragments coupled via a linker are called "diabody" which form is also encompassed by the invention.

5.3 Bispecific Antibodies

The present application further includes a bispecific antibody or antigen-binding fragment thereof in which one specificity is for an immunogenic RAGE polypeptide of the present application. For example, a bispecific antibody can be generated that specifically binds to an immunogenic RAGE polypeptide of the invention through one binding domain and to a second molecule through a second binding domain In addition, a single chain antibody containing more than one VH and VL may be generated that binds specifically to an immunogenic polypeptide of the invention and to another molecule that is associated with attenuating myelin mediated growth cone collapse and inhibition of neurite outgrowth and sprouting. Such bispecific antibodies can be generated using techniques that are well known for example, Fanger et al. *Immunol Methods* 4: 72-81 (1994).

In some embodiments, the bispecific antibodies are prepared using one or more of the variable regions from an antibody of the invention. In another embodiment, the bispecific antibody is prepared using one or more CDR regions from said antibody.

5.4 Derivatized and Labeled Antibodies

An antibody or an antigen-binding fragment of the present application can be derivatized or linked to another molecule (e.g., another peptide or protein). In general, the antibody or antigen-binding fragment is derivatized such that binding to an immunogenic polypeptide of the invention is not affected adversely by the derivatization or labeling.

For example, an antibody or antibody portion of the present application can be functionally linked (by chemical coupling, genetic fusion, noncovalent association or otherwise) to one or more other molecular entities, such as another antibody (e.g., a bispecific antibody or a diabody), a detection reagent, a cytotoxic agent, a pharmaceutical agent, and/or a protein or peptide that can mediate association of the antibody or antigen-binding fragment with another molecule (such as a streptavidin core region or a polyhistidine tag). Still further, an antibody or antigen-binding portion thereof may be part of a larger immunoadhesion molecule, formed by covalent or non-covalent association of the antibody or antibody portion with one or more other or different proteins or peptides. Examples of such immunoadhesion molecules include use of the streptavidin core region to make a tetrameric scFv molecule (Kipriyanov et al. (1995) *Human Antibodies and Hybridomas* 6:93-101) and use of a cysteine residue, a marker peptide and a C-terminal polyhistidine tag to make bivalent and biotinylated scFv molecules (Kipriyanov et al. (1994) *Molecular Immunology* 31:1047-1058). Antibody portions, such as Fab and F(ab')₂ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

A derivatized antibody may be produced by crosslinking two or more antibodies (of the same type or of different types, e.g., to create bispecific antibodies). Suitable crosslinkers include those that are heterobifunctional, having two distinctly reactive groups separated by an appropriate spacer (e.g. m-maleimidobenzoyl-N-hydroxysuccinimide ester) or homobifunctional (e.g., disuccinimidyl suberate). Such linkers are available from Pierce Chemical Company, Rockford, Ill.

A derivatized antibody may also be a labeled antibody. For instance, detection agents with which an antibody or antibody portion of the invention may be derivatized are fluorescent compounds, including fluorescein, fluorescein isothiocyanate, rhodamine, 5-dimethylamine-1-napthalenesulfonyl chloride, phycoerythrin, lanthanide phosphors and the like. An antibody also may be labeled with enzymes that are useful for detection, such as horseradish peroxidase, galactosidase, luciferase, alkaline phosphatase, glucoseoxidase and the like. In embodiments that are labeled with a detectable enzyme, the antibody is detected by adding additional reagents that the enzyme uses to produce a detectable reaction product. For example, horseradish peroxidase with hydrogen peroxide and diaminobenzidine. An antibody also may be labeled with biotin, and detected through indirect measurement of avidin or streptavidin binding. An antibody may also be labeled with a predetermined polypeptide epitope recognized by a secondary reporter (e.g., leucine zipper pair sequences, binding sites for secondary antibodies, metal binding domains, epitope tags). An RAGE antibody or an antigen fragment thereof also may be labeled with a radio-labeled amino acid. The radiolabel may be used for both diagnostic and therapeutic purposes. The radio-labeled RAGE antibody may be used diagnostically, for example, for determining RAGE receptor levels in a subject. Further, the radio-labeled RAGE antibody may be used therapeutically for treating spinal cord injury.

Examples of labels for polypeptides include, but are not limited to, the following radioisotopes or radionucleotides $^{15}N$, $^{35}S$, $^{90}Y$, $^{99}Tc$, $^{111}In$, $^{125}I$, $^{131}I$, $^{177}Lu$, $^{166}Ho$, $^{153}Sm$. A RAGE antibody or an antigen fragment thereof may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding. Also, a label for polypeptides can include a nucleic acid, for example DNA for detection by PCR, or enhancing gene expression, or siRNA to suppress gene expression in RAGE-bearing cells or tissues.

The class and subclass of RAGE antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various classes and subclasses of immunoglobulins, and determining the class and subclass of the antibodies.

5.5 Dual Variable Domain Immunoglobulins

Dual variable domain (DVD) binding proteins or immunoglobulins as used herein, are binding proteins that comprise two or more antigen binding sites and are tetravalent or multivalent binding proteins, as for example divalent and tetravalent. The term "multivalent binding protein" is used in this specification to denote a binding protein comprising two or more antigen binding sites. The multivalent binding protein is particularly engineered to have the two or more antigen binding sites, and is generally not a naturally occurring antibody. The term "multispecific binding protein" refers to a binding protein capable of binding two or more related or unrelated targets. Such DVDs may be monospecific, i.e capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. patent application Ser. No. 11/507,050 and incorporated herein by reference. It is intended that the present invention comprises a DVD binding protein comprising binding proteins capable of binding RAGE. Particularly the DVD binding protein is capable of binding RAGE and a second target. The second target is selected from the group consisting of anti inflammatory MAB activities (IL-1, IL-6, IL-8, IL-11, IL-12, IL-17, IL-18, IL-23,TNF alpha/beta, IFN-beta, gamma, LIF, OSM, CNTF, PF-4, Platelet basic protein (PBP), NAP-2, beta-TG, MIP-1, MCP2/3, RANTES, lymphotactin), of transport-mediating proteins (insulin receptor, transferrin receptor, thrombin receptor, leptin receptor, LDL receptor), of other neuroregenerative MABs (NgR, Lingo, p75, CSPG (e.g. NG-2, neurocan, brevican, versican, aggrecan) hyaluronic acid, mAG, tenascin, NI-35, NI-250, IMP, perlecan, neurocan, phosphacan, nogo-A, OMGP, Sema4D, Sema 3A, ephrin B3, ephrin A2, ephrin A5, MAG, EphA4, plexin B1, TROY, wnts, ryk rec., BMP-2, BMP-4, BMP-7), of neuroprotective MAB activities (EGF, EGFR, Sema 3), of anti-amyloid beta MABs (e.g. m266, 3D6 (bapineuzumab), anti-globulomer MABs 7C6), of CNS located receptors and transporters (serotonin receptors, dopamine receptors, DAT, Asc-1, GlyT1).

5.6 Dual-Specific Antibodies

The present application also describes "dual-specific antibody" technology. Dual-specific antibodies may serve as agonists, antagonists, or both in different combinations. Dual-specific antibodies are antibodies in which the VH chain binds to a first antigen and the VL chain binds to another antigen as exemplified in WO 2008/082651.

5.7 Crystallized Antibodies

Another embodiment of the present application provides a crystallized binding protein. The term "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, *Crystallization of Nucleic Acids and Proteins*, a Practical Approach, $2^{nd}$ ed., pp. 201-16, Oxford University Press, New York, N.Y., (1999).

Particularly the present application describes crystals of whole RAGE antibodies and fragments thereof as disclosed herein, and formulations and compositions comprising such crystals. In one embodiment the crystallized binding protein has a greater half-life in vivo than the soluble counterpart of the binding protein. In another embodiment the binding protein retains biological activity after crystallization.

Crystallized binding protein of the invention may be produced according methods known in the art and as disclosed in WO 02/072636, incorporated herein by reference.

5.8 Glycosylated Antibodies

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO J.* (1991) 10:2717 2723).

One aspect of the present invention is directed to generating glycosylation site mutants in which the O- or N-linked glycosylation site of the binding protein has been mutated. One skilled in the art can generate such mutants using standard well-known technologies. Glycosylation site mutants that retain the biological activity but have increased or decreased binding activity are another object of the present invention.

In still another embodiment, the glycosylation of the antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO 2003/016466A2, and U.S. Pat. Nos. 5,714,350 and 6,350,861, each of which is incorporated herein by reference in its entirety.

Additionally or alternatively, a modified antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (eg., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Particularly the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent applications 20040018590 and 20020137134 and PCT publication WO 2005/100584 A2).

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Particularly, the protein having a particularly selected novel glycosylation pattern exhibits improved or altered biological properties.

5.9 Anti-Idiotypic Antibodies

In addition to the binding proteins, the present invention is also directed to an anti-idiotypic (anti-Id) antibody specific for such binding proteins of the invention. An anti-Id antibody is an antibody, which recognizes unique determinants generally associated with the antigen-binding region of another antibody. The anti-Id can be prepared by immunizing an animal with the binding protein or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

6. Pharmaceutical Compositions

The invention also provides pharmaceutical compositions comprising an antibody, or antigen-binding portion thereof, of the invention and a pharmaceutically acceptable carrier. The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which RAGE activity is detrimental. Particularly, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, *J. Biol. Chem.* 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidurala administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissel®), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see Langer, supra; Sefton, 1987, *CRC Crit. Ref. Biomed. Eng.* 14:20; Buchwald et al., 1980, *Surgery* 88:507; Saudek et al., 1989, *N. Engl. J. Med.* 321:574). In another embodiment, polymeric materials can be used to achieve controlled or sustained release of the therapies of the invention (see e.g., *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J., Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. No. 5,679,377; U.S. Pat. No. 5,916,597; U.S. Pat. No. 5,912, 015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in *Medical Applications of Controlled Release*, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526, 938, PCT publication WO 91/05548, PCT publication WO 96/20698, Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science &Technology* 50:372-397, Cleek et al., 1997, "Biodegradable Polymeric Carriers for a bFGF Antibody for Cardiovascular Application," *Pro. Int'l. Symp. Control. Rel. Bioact. Mater.* 24:853-854, and Lam et al., 1997, "Microencapsulation of Recombinant Humanized Monoclonal Antibody for Local Delivery," *Proc. Intl. Symp. Control Rel. Bioact. Mater.* 24:759-760, each of which is incorporated herein by reference in their entireties.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well known to one of skill in the art. See, e.g., *Remington's Pharmaceutical Sciences and Introduction to Pharmaceutical Dosage Forms,* 19th ed., Mack Pub. Co., Easton, Pa. (1995). For non-sprayable topical dosage forms, viscous to semi-solid or solid forms comprising a carrier or one or more excipients compatible with topical application and having a dynamic viscosity particularly greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, particularly in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Particularly, one or more of the prophylactic or therapeutic agents or pharmaceutical compositions of the invention is supplied as a dry sterile lyophilized powder in a hermetically sealed container at a unit dosage of at least 5 mg, more particularly at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, particularly within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Particularly, the liquid form of the administered composition is supplied in a hermetically sealed container at least 0.25 mg/ml, more particularly at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies and antibody-portions of the invention can be incorporated into a pharmaceutical composition suitable for parenteral administration. Particularly, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies and antibody-portions of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (see WO 2004/078140, US2006104968 incorporated herein by reference).

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The particular form depends on the intended mode of administration and therapeutic application. Typical particular compositions are in the form of injectable or infusible solutions, such as compositions similar to those used for passive immunization of humans with other antibodies. A particular mode of administration is parenteral (e.g., intravenous, subcutaneous, intraperitoneal, intramuscular). In a particular embodiment, the antibody is administered by intravenous infusion or injection. In another particular embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, particular methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody-portions of the present invention can be administered by a variety of methods known in the art, although for many therapeutic applications, a particular route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which RAGE activity is detrimental. For example, an anti-RAGE antibody or antibody portion of the invention may be coformulated and/or coadministered with one or more additional antibodies that bind other targets (e.g., antibodies that bind cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody to RAGE or fragment thereof is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In a specific embodiment, nucleic acid sequences comprising nucleotide sequences encoding an antibody of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody or prophylactic or therapeutic agent of the invention that mediates a prophylactic or therapeutic effect.

Any of the methods for gene therapy available in the art can be used according to the present invention. For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, *Science* 260:926-932 (1993); and Morgan and Anderson, 1993, *Ann. Rev. Biochem.* 62:191-217; May, 1993, TIBTECH 11(5):155-215. Methods commonly known in the art of recombinant DNA technology which can be used are described in Ausubel et al. (eds.), *Current Protocols in Molecular Biology*, John Wiley &Sons, NY (1993); and Kriegler, *Gene Transfer and Expression, A Laboratory Manual*, Stockton Press, NY (1990). Detailed description of various methods of gene therapy are disclosed in US20050042664 A1 which is incorporated herein by reference.

RAGE plays a critical role in the pathology associated with a variety of diseases as defined herein above. Infusion of amyloid Aβ-peptides into animals leads to responses like inflammatory responses in arteriolose, decrease in cerebral blood flow. These effects could be prevented by antibodies against RAGE (Rhodin, J. et al. *World Congress for Microcirculation*, submitted Papers, 7th, Sydney, Australia, Aug. 19-22, 2001, 543-547; Deane et al. Nature Med. 2003). RAGE is upregulated in the microvasculature of AD patients and in transgenice mice where the human APP gene has been overexpressed (Deane et al. *Nature Med.* 2003). Using double-transgenic mice where the human APP gene is expressed and RAGE is overexpressed it was shown that overexpression of the normal RAGE gene leads to impairment in learning, increase in plaques whereas overexpression of a dominant-negative signalling defective RAGE variant leads to improvement in learning and lower plaque levels (Arancio et al. 2004 *EMBO J.* 2004). Experimentation in animal models of both Type 1 and 2 diabetes reveals that antagonism of the ligand-RAGE axis suppresses the development and progression of vascular and inflammatory cell perturbation in the diabetic milieu, e.g. RAGE knock-out mice and Anti-RAGE antibodies have been used to show an improvement in animal models for e.g. diabetic nephropathy (Ravichandran R. et al. *Canadian Journal of Diabetes* 2006;

30(4):422, Myint Khin et al. *Diabetes* (2006), 55(9), 2510; De-Vriese et al. *Journal of the American Society of Nephrology* 2003, 14/8, 2109, Jensen et al), and diabetic neuropathy (Bierhaus, A. *J Clin Invest.* 2004 December; 114(12):1741-51). Renal effects of a neutralising RAGE-antibody in long-term streptozotocin-diabetic mice. *The Journal of Endocrinology,* 2006, 188, 493). Positive long-term renal effects of a neutralizing RAGE antibody in obese type 2 diabetic mice were shown by Flyvbjerg et al (*Diabetes,* 2004, 53, 1, p. 166-72). RAGE knock-out mice were used to show an involvement of RAGE in sepsis (Birgit Liliensiek et al. *J Clin Invest.* 2004 June 1; 113(11): 1641-1650; Receptor for advanced glycation end products (RAGE) regulates sepsis but not the adaptive immune response). Blocking F(ab)$_2$ fragments derived from anti-RAGE IgG reduces the inflammatory response in MOG or MBP-induced EAE (Yan, S. S., et al. 2003. *Nat. Med.* 9:287-293.) Involvement of RAGE in cancer was shown (Abe-R et al. *Journal of Investigative Dermatology,* 2004, 122/2 (461-467). In tumor-bearing mice, survival rates were prolonged, and spontaneous pulmonary metastases were inhibited by treatment using anti-RAGE neutralizing antibodies.

The antibodies, and antibody portions of the invention can be used to treat humans suffering from such a diseases.

It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent, which affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

Non-limiting examples of therapeutic agents for multiple sclerosis with which an antibody, or antibody portion, of the invention can be combined include the following: corticosteroids; prednisolone; methylprednisolone; azathioprine; cyclophosphamide; cyclosporine; methotrexate; 4-aminopyridine; tizanidine; interferon-β1a (AVONEX; Biogen); interferon-β1b (BETASERON; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-23, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD19, CD20, CD25, CD28, CD30, CD40, CD45, CD69, CD80, CD86, CD90 or their ligands. The antibodies of the invention, or antigen binding portions thereof, may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFalpha or IL-1 (e.g. IRAK, NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFbeta).

Particular examples of therapeutic agents for multiple sclerosis in which the antibody or antigen binding portion thereof can be combined to include interferon-beta, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

Particularly, the binding proteins and antibodies of the present invention may be utilized to treat an amyloidosis, for example, Alzheimer's disease and Down's syndrome. It should be understood that the binding proteins and antibodies of the invention can be used alone or in combination with at least one additional agents suitable for treating one of the above diseases. Said at least one additional agent may be selected by the skilled artisan for its intended purpose. For example, the additional agent can be a therapeutic agent such as a cholesterinase inhibitor (e.g., tactrine, donepezil, rivastigmine or galantamine), a partial NMDA receptor blocker (e.g., memantine), a glycosaminoglycan mimetic (e.g., Alzhemed), an inhibitor or allosteric modulator of gamma secretase (e.g., R-flurbiprofen), a luteinizing hormone blockade gonadotropin releasing hormone agonist (e.g., leuprorelin), a serotinin 5-HT1A receptor antagonist, a chelatin agent, a neuronal selective L-type calcium channel blocker, an immunomodulator, an amyloid fibrillogenesis inhibitor or amyloid protein deposition inhibitor (e.g., M266), another antibody (e.g., bapineuzumab), a 5-HT1a receptor antagonist, a PDE4 inhibitor, a histamine agonist, a receptor protein for advanced glycation end products, a PARP stimulator, a serotonin 6 receptor antagonist, a 5-HT4 receptor agonist, a human steroid, a glucose uptake stimulant which enhanced neuronal metabolism, a selective CB1 antagonist, a partial agonist at benzodiazepine receptors, an amyloid beta production antagonist or inhibitor, an amyloid beta deposition inhibitor, a NNR alpha-7 partial antagonist, a therapeutic targeting PDE4, a RNA translation inhibitor, a muscarinic agonist, a nerve growth factor receptor agonist, a NGF receptor agonist and a gene therapy modulator (i.e., those agents currently recognized, or in the future being recognized, as useful to treat the disease or condition being treated by the antibody or binding protein of the present invention). The additional agent also can be an agent that imparts a beneficial attribute to the therapeutic composition e.g., an agent that affects the viscosity of the composition.

The antibodies of the invention, or antigen binding portions thereof, may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists, IL-4 agonists.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more particularly 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

Example 1

Anti-huRAGE Antibodies 1.1 Production of Hybridomas and Antibodies.

Balb/c and A/J mice, 4-6 weeks of age, were immunized and boosted subcutaneously with human RAGE. Animals were injected every three weeks, beginning with a primary injection of 30 µg in complete Freund's adjuvant and injection boosts of 30 µg in Incomplete Freund's Adjuvant. Mice selected for fusion were injected intravenously with 10 µg hRAGE in saline, four days prior to fusion. Spleens from immunized animals were removed and single cell suspensions were prepared. SP2/0 myeloma cells were harvested from culture and washed. Spleen cells and tumor cells were mixed at a ratio of 5:1 and fused using 50% PEG 3000 using standard techniques (Kohler and Milstein, 1975). Fused cells were seeded in 96 well plates in selective media, at a density of $2.5 \times 10^5$ spleen cells per well. Fusions were incubated at 37° C. for 7-10 days. When macroscopic colonies were observed, supernatants were removed and tested in the hRAGE ELISA.

Hybridomas that were producing mAbs with desired characteristics were subcloned by the limiting dilution method. Supernatant containing subclones were assayed for binding to hRAGE by ELISA. Heavy and light chain subclasses of the mAbs were determined using the Zymed EIA Isotyping kit.

1.2. Determination of the Amino Acid Sequence of the Variable Region for Each Murine Anti-Human RAGE mAb.

For each amino acid sequence determination, approximately $10 \times 10^6$ hybridoma cells were isolated by centrifugation and processed to isolate total RNA with Trizol (Gibco BRL/Invitrogen, CA.) following manufacturer's instructions. Total RNA was subjected to first strand DNA synthesis using the SuperScript First-Strand Synthesis System (Invitrogen, CA) per the manufacturers instructions. Oligo(dT) was used to prime first-strand synthesis to select for poly(A)$^+$ RNA. The first-strand cDNA product was then amplified by PCR with primers designed for amplification of murine immunoglobulin variable regions (Ig-Primer Sets, Novagen, Wis.). PCR products were resolved on an agarose gel, excised, purified, and then subcloned with the TOPO Cloning kit into pCR2.1-TOPO vector (Invitrogen, CA) and transformed into TOP10 chemically competent E. coli (Invitrogen, CA). Colony PCR was performed on the transformants to identify clones containing insert. Plasmid DNA was isolated from clones containing insert using a QIAprep Miniprep kit (Qiagen, Valencia, Calif.). Inserts in the plasmids were sequenced on both strands to determine the variable heavy or variable light chain DNA sequences using M13 forward and M13 reverse primers (Fermentas Life Sciences, Hanover Md.). Variable heavy and variable light chain sequences of the 3 monoclonal antibodies 7F9, 11E6 and 4E5 and their three variable heavy chain CDRs and three variable light chain CDRs are listed in Table 4, above.

1.3. Construction and Expression of Recombinant Anti Human RAGE Antibodies

The DNA encoding the heavy chain constant region of murine anti-human RAGE monoclonal antibodies 7F9, 11E6 and 4E5 was replaced by a cDNA fragment encoding the human IgG1 constant region by homologous recombination in bacteria. The light chain constant region of each of these antibodies was replaced by a human kappa constant region (Table 1, above). Full-length chimeric antibodies were transiently expressed in COS cells or 293 cells by co-transfection of chimeric heavy and light chain cDNAs ligated into the pBOS or pTT3 expression plasmid (Mizushima and Nagata, Nucleic Acids Research 1990, Vol 18, pg 5322). Cell supernatants containing recombinant chimeric antibody were purified by Protein A Sepharose chromatography and bound antibody was eluted by addition of acid buffer. Antibodies were neutralized and dialyzed into PBS.

1.4. ELISA Binding of Recombinant Anti-Human RAGE mAbs and of Hybridoma-Derived Anti-Human RAGE mAbs.

Figure 1B:
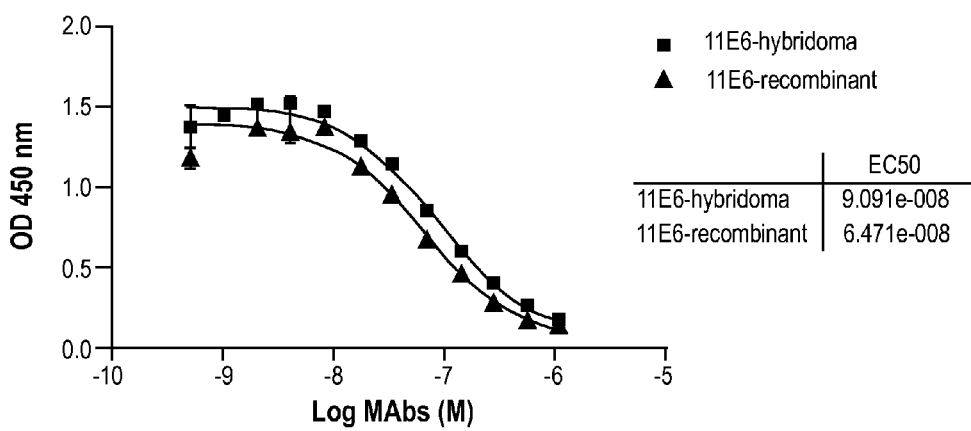
Figure 1C:
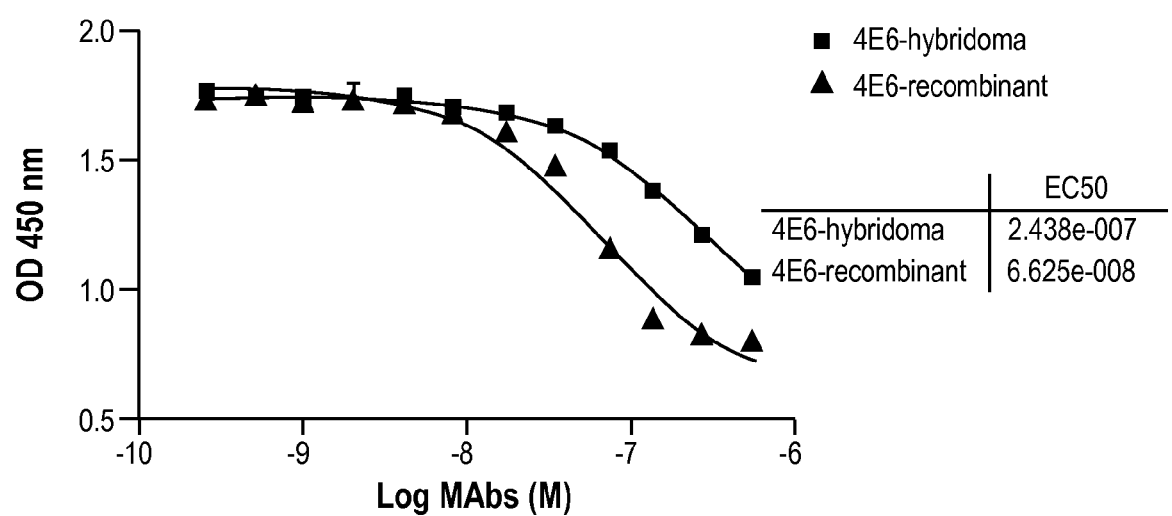

The purified chimeric anti-human RAGE monoclonal antibodies were tested for their ability to bind human RAGE in a competition ELISA. Recombinant chimeric anti-human RAGE monoclonal antibodies or hybridoma-derived anti-human RAGE monoclonal antibodies were diluted in PBST+10% Superblock (Pierce Biotech, Rockford, Ill.) and made up as a 2× stock at various concentrations ranging from 320 µg/mL to 0.0156 µg/mL (7F9 and 11E6) and from 160 µg/mL to 0.0078 µg/mL (4E5). Biotinylated hybridoma-derived anti-human RAGE monoclonal antibodies (7F9-biotin, 11E6-biotin and 4E5-biotin) were prepared at 8 µg/mL in PBST+10% Superblock. Equal volumes (50 µL) of each recombinant chimeric anti-human RAGE monoclonal antibodies or hybridoma-derived anti-human RAGE monoclonal antibodies and each corresponding biotinylated hybridoma-derived anti-RAGE mAbs were mixed. 50 µL, of this mixture was then added to ELISA plates pre-coated with recombinant human RAGE at 2 µg/mL and incubated for 1.5 hours at room temperature. Wells were washed three times with PBS+0.05% Tween-20. Streptavidin HRP (1 mg/mL) was diluted 1:16000 in PBST+10% Superblock; 50 L/well was added and the plates incubated for 1 hour at room temperature. Plates were washed 3 times with PBS+0.05% Tween-20. 50 µL of TMB solution (Sigma, St Louis, Mo.) was added to each well and incubated for 10 minutes at room temperature. The reaction was stopped by addition of 1N sulphuric acid. Plates were read spectrophotometrically at a wavelength of 450 nm Results are shown in FIGS. 1A, 1B, and 1C.

Example 2

Generation of Recombinant Human sRAGE (husRAGE)

Recombinant husRAGE protein 293/6.1 sRAGE His 6 was expressed and purified in HEK293 cell (ATCC CRL-1573). The expression vector used for the generation of the stable expression was "pcDNA3 (−) 6.1 C HIS A".

Molecular biological standard techniques were used according to Sambrook and Russel (Molecular Cloning: A Laboratory Manual, 3rd edition, Cold Spring Harbor Laboratory Press. 2001). Total RNA from human lymphocytes (PBL) was reverse transcribed into cDNA using Superscript RT-PCR system (Invitrogen, Carlsbad USA). Using the oligonucleotide primers RAGE-SE: CCG AAT TCC GGA AGC AGG ATG GCA GCC G (SEQ ID NO: 81) and RAGE-AS: CCC TCG AGC CCC TCA AGG CCC TCA GTA CTA CT (SEQ ID NO: 82), the RAGE cDNA was amplified from the cDNA (obtained above) yielding the RAGE cDNA as described in reference sequence NM-001136. The PCR-fragment was run on an agarose gel, purified and extracted with QIAquick Gelextraction Kit (Qiagen GmbH, Germany). Afterwards the cDNA was cut with restriction endonucleases EcoR1 and XhoI. The resulting fragment was gel purified and ligated into vector pcDNA 3 (Invitrogen, USA) which had been precut with XhoI/EcoR1. After transformation into E. coli XL-1 blue cells (Invitrogen, USA) a positive recombinant clone was identified. The sequence of this clone was verified and the pcDNA3/RAGE 2.6 plasmid DNA isolated using plasmid mini-Kit (Qiagen, Germany). The coding region for the extracellular part of RAGE, husRAGE, was amplified from pcDNA3/RAGE 2.6 using PCR and primers N-SE A: AGT AAC GGC CGC CAG TGT GCT GGA ATT CGG A (SEQ ID NO: 83) and C-SE B: CCG GTA CCA CCT GCA GTT GGC CCC TCC TCG CC (SEQ ID NO: 84). The resulting PCR product was cut with restriction endonucleases EcoR1 and Kpn1, gel purified as described above and ligated into "pcDNA3.1(−) Myc HIS" (Invitrogen, USA) which had been precut with EcoR1/Kpn1. The resulting plasmid "pcDNA 3 (−) 6.1 C HIS A" was transfected into HEK293 cells using Superfect (Qiagen, Germany) according to manufacturers instructions. Selection of resistant cells was done using 800 µg/ml G418 in MEM Medium (#M4528, Sigma, Germany)+10% FCS, 2 mM L-Glutamin, 100 U/ml Pennicillin/Streptavidin (Invitrogen, USA). Cloning of single cells through serial dilutions of cell suspensions lead to the identification of a clone "293/6.1 sRAGE His 6" that secreted husRAGE into the cell culture medium as confirmed by Western Blot using a RAGE specific antibody (Santa Cruz; # sc5563). For expression and purification of sufficient amounts of husRAGE protein this clone was grown in serum containing cell culture medium (see above) in cell factories (Nunc, Germany). Cells were then switched to serum-free medium Pro293a-CDM (#12-764Q, BioWhittaker, Belgiun) and incubated for 3 days at 37° C. 80 liters of cell free medium was harvested and concentrated using Hemoflow F-Series High-Flux columns (Fresenisus Medical Care AG, Germany) to a volume of 1400 ml.

Protein purification was done using immobilized metal ion affinity chromatography (IMAC) by Diarect AG (Freiburg, Germany) and sepharose FF for chelation (Amersham-Bioscience, Sweden). Equilibration of the column and binding of the hexa-His containing protein from cell supernatants to the matrix were done according to instructions by the manufacturer. Elution of the protein was done using step gradients with increasing concentrations of imidazole. Eluted fractions were analyzed for protein containing hexa-His using Western Blots and anti HIS antibodies. Purified husRAGE eluted specifically at 250-500 mM imidazole. Positive fractions were combined, concentrated and dialyzed 3 times against PBS (2×4 h, 1×16 h).

A N-terminal shortened version of husRAGE (102-331-sRAGE-HIS) missing the first 101 amino acids of human RAGE was generated by standard techniques in molecular biology as described above for the husRAGE protein. This protein was generated by the same basic procedure used for husRAGE (1-331). Using the plasmid described above (pcDNA3/RAGE 2.6) and two primers (CGA AGC TTG ATG AAC AGG AAT GGA AAG GAG ACC AAG (SEQ ID NO: 85) and TCC TCG AGC ACC TGC AGT TGG CCC CTC CTC GCC T (SEQ ID NO: 86)) the shorter version of the DNA for husRAGE was amplified by PCR. After agarose gel and elution of the fragment the resulting pure fragment was cleaved with restriction endonucleases HindIII and XhoI and purified again using agarose gel and elution. The fragment was ligated into psecTAG 2A (Invitrogen, USA) that was precut with restriction endonucleases HindIII and XhoI. After transformation into E. coli "TOP10 One Shot" cells (Invitrogen, USA) a positive clone was picked and the plasmid DNA isolated. The DNA in the expression vector was transfected into HEK293 F cells using the Freestyle expression system (Invitrogen, USA). After 96 hours of expression the cell free supernatant was used for the purification using Ni-NTA Superflow beads (Quiagen, Germany). Equilibration and binding were done according to instruction by the manufacturer. Bound protein was eluted in buffer (PBS, 160 mM NaCl, 150 mM Imidazole, pH8.0). Fractions containing protein were combined and dialyzed over night at 4° C. against TBS (Tris-buffered saline; pH 7,4). Purified husRAGE (102-331) concentrations were determined spectrophotometrically.

A C-terminal shortened version of husRAGE-fusion protein (1-130-sRAGE-Fc) missing the amino acids following amino acid 130 of human RAGE was generated by standard techniques in molecular biology as described above for the husRAGE protein. Using the plasmid described above (pcDNA3/RAGE 2.6) and two primers (GCACCATG-GCAGCCGGAACAGCAGTTG (SEQ ID NO: 87) and GAGTCTCGAGGCAGAATCTACAATTTCTG (SEQ ID NO: 88)) the shorter version of the DNA for husRAGE was amplified by PCR. After agarose gel and elution of the fragment the resulting pure fragment was cleaved with restriction endonucleases NcoI and XhoI and purified again using agarose gel and elution. The fragment was then ligated into the plasmid pENTR4 that was precut with restriction endonucleases NcoI and XhoI. The ligation mixtures were transformed into E. coli "TOP10 One Shot" cells (Invitrogen, USA) to generate pENTR4-RAGE 1-130. A positive clone was picked and the plasmid DNA isolated. Using site specific recombination and the gateway cloning system (Invitrogen, Carlsbad, USA; attL×attR) with DNA of the clone pENTR4 hRAGE 1-130 and DNA of the vector pcDNA3.1(+)Zeo hIgG lambda hc 257-Stop a plasmid was constructed (see below) that after transformation into "TOP10 One Shot" cells (Invitrogen, USA) and purification encoded for husRAGE-1-130-Fc (plasmid called: pEXP hRAGE 1-130/hIgG lambda hc 257-Stop). Expression of this plasmid using the Freestyle Expression system and 293F cells (Example 2.1) and purification of the resulting protein from the cell supernatant using Protein G-beads (Example 2.2) resulted in a protein with >95% purity.

Example 3

Construction of pcDNA3.1(+)Zeo hIgG lambda hc 257-Stop 2 oligonucleotide primers (gtacgatatcgagggacgaatggatc-caccgtgcccagcacc (SEQ ID NO: 91); ctagtctagatcatttacccg-gagacagggag (SEQ ID NO: 92)) were used to amplify the DNA sequence for hIgG lambda heavy chain from a human placenta cDNA Library (Clontech # HL5014a) using EasyA Polymerase in a PCR, polymerase chain reaction. The resulting DNA was gel purified (as described above), cloned into pcDNA3.1 V5-His TOPO Vektor (pcDNA3.1/V5/His TOPO TA Expression Kit Invitrogen #K4800-01) using instruction from the manufacturer and transformed into E. coli TOP10 cells as described above. Positive clones were identified and the resulting plasmid DNA purified (named: pcDNA3.1 (V5His) FC/hIgG lambda hc Nr.2/7) using PCR and oligo-nucleotide primers (gtacgatatcgagggacgaatggatc-caccgtgcccagcacc (SEQ ID NO: 93); ctagtctagatcatttacccg-gagacagggag (SEQ ID NO: 94)). The hIgG lambda hc part of the DNA was amplified, cut with EcoRV/XbaI, ligated to EcoRV/XbaI precut pcDNA3.1(+)Zeo vector DNA and transformed into E. coli TOP10 cells. The resulting plasmid was named: pcDNA3.1(+)Zeo hIgG lambda hc 257-Stop and used for further work to express proteins N-terminally fused in frame to a C-terminal part of immunoglobulin IgG heavy chains.

3.1. Transfection and Expression of Proteins in HEK293F Cells

HEK 293F cells that had been grown in culture for 2-3 days in Free Style 293 Expression Medium were centrifuged at 400 g and the supernatant discarded. The cell pellet was resuspended in medium and adjusted to $3 \times 10^7$ cells in 28 ml fresh medium, transferred to a 125 ml Erlenmeyer and incubated in an incubator at 37° C., 8% CO2 on an orbital shaker at 150 rpm until the transfection mixture was set up.

Transfection mixtures with 293fectin-DNA complex were set up as follows:

(i) 30 µg of DNA were diluted with Opti-MEM Ito a total volume of 1000 µl (control 1000 µl Opti-MEM I) and mixed.

(ii) 35 µl of 293fectin (Invitrogen #12347-019; 1 ml) were diluted with Opti-MEM Ito a total volume of 1000 µl, mixed and incubated for 5 min at room temperature.

DNA mixture and 239fectin-solution from (i) and (ii) were transferred to a new tube, mixed slightly and after incubation for 25 minutes at room temperature were added to the cells in the Erlenmeyer.

Cells were incubated with this transfection mixture for the indicated time in an incubator at 37° C., 8% $CO_2$ on an orbital shaker at 150 rpm. Cell supernatants were harvested by centrifugation at 400 g for 10 minutes.

3.2. Purification of RAGE-Fc Fusion Proteins Using Protein G-Sepharose

To couple the protein from cell supernatants to beads, beads (protein G-sepharose 4 Fast Flow (Amersham Bioscience) were washed 3 times in PBS by suspending the beads in PBS and centrifugation at 13,500 rpm, discarding the supernatant. Beads were incubated with the respective cell supernatants (300 ml cell supernatants per ml beads) to be coupled for 1-2 hours on a rotator at room temperature. The beads were washed 3 times with PBS and incubated with the cell supernatants for 12 hours or overnight at 4° C. After incubation the beads were washed 3 times with PBS as above. Bound protein was eluted by adding 200 µl 140 mM NaCl+ 0.1M glycine to the bead pellet and incubating for 30 minutes on a rotator. After centrifugation the supernatant was immediately neutralized by adding 2 M Tris to adjust the pH to 7.1-pH 7.4. The bead pellet was discarded. Obtained Probes were dialyzed against PBS and stored frozen in aliquots at −20° C. RAGE-Fc fusion protein containing the full extracellular ectodomain of RAGE was obtained from R&D systems (no. 1145-RG; Recombinant Human RAGE/Fc Chimera).

3.3. Dot Blot Binding of Antibodies to Peptides or Fragments of RAGE in a Non Denatured Form Dot blots were used to evaluate the binding of antibodies to peptides or fragments of RAGE in a non-denatured form. Proteins used were either sRAGE-Protein (1-331 sRAGE-HIS) or a N-terminal shortened version (102-331-sRAGE-HIS). Peptides were ordered and synthesized by Biotrend according to standard methods (solid phases peptide synthesis on AMS 222 synthesizer using Fmoc/tBu-chemistry) containing a free carboxyl terminus Peptides were HPLC-purified and analysis of every peptide for purity was done using RP-HPLC. All peptides had a purity of >80%. The identities of peptides were verified by mass spectrometry.

Peptides used were 30mers spanning the extracellular region of the human RAGE protein. Net charge of most peptides was similar.

```
                                              (SEQ ID NO: 70)
NtermR31:     QNITARIGEPLVLKCKGAPKKPPQRLEWKLN
              Net charge: +7

(SEQ ID NO: 71)
Peptide 1:    KLNTGRTEAWKVLSPQGGGPWDSVARVLPN
              Net charge: +2
```

-continued

Peptide 2: LPNGSLFLPAVGIQDEGIFRCQAMNRNGKE (SEQ ID NO: 72)
Net charge: 0

Peptide 3: GKETKSNYRVRVYQIPGKPEIVDSASELTA (SEQ ID NO: 73)
Net charge: +1

Peptide 4: LTAGVPNKVGTCVSEGSYPAGTLSWKLDGK (SEQ ID NO: 74)
Net charge: +1

Peptide 5: DGKPLVPNEKGVSVKEQTRRHPETGLFTLQ (SEQ ID NO: 75)
Net charge: +2

Peptide 6: TLQSELMVTPARGGDPRPTFSCSFSPGLPR (SEQ ID NO: 76)
Net charge: +1

Peptide 7: LPRHRALRTAPIQPRVWEPVPLEEVQLVVE (SEQ ID NO: 77)
Net charge: +2

Peptide 8: VVEPEGGAVAPGGTVTLTCEVPAQPSPQIH (SEQ ID NO: 78)
Net charge: -2

Peptide 9: QIHWMKDGVPLPLPPSPVLILPEIGPQDQG (SEQ ID NO: 79)
Net charge: +0

Peptide 10: DQGTYSCVATHSSHGPQESRAVSISIIEPG (SEQ ID NO: 80)
Net charge: -1

Dots consisting of different amount of protein/peptide (30 ng, 10 ng, 3 ng, 1 ng, 0.3 ng, 0.1 ng, 0.03 ng, and 0.01 ng) in a volume of 1 μl in 1×PBS were spotted onto a Hybond-ECL Nitrocellulose Membrane (Amersham, RPN68D) in duplicates. Membranes were dried and unspecific binding was blocked by shaking the membranes for 1 hour at room temperature with Western Blocking reagent (Roche, no. 1921673). Blocking reagent was discarded and the membranes were incubated with antibodies in a concentration of 7.14 nM (shaking, 1 hour at room temperature). Monoclonal antibodies were ML37-7F9, ML37-11E6, ML37-4E5, commercially available antibodies from R&D systems (e.g. AF1145). Blots were washed 4 times (each time 5 minute incubation with shaking at room temperature) with 1×PBS. Blots were then incubated with goat anti mouse IgG AP secondary antibody (Sigma no. A-7434) diluted 1:2000 in Western Blocking Reagent (Roche, no. 192173). Incubation for 1 hour was as before (shaking, room temperature). The filters were washed 4 times (5 minutes each) in 1×PBS. Development of signals was according to manufacturers instructions with NBT/BCIP substrate solution (Roche, no. 1697471). Color development was stopped after 10 minutes with bi-distilled water. See FIG. 2.

Although husRAGE was detected in dot blots by all three monoclonal antibodies of the present invention and by polyclonal antibody AF1145 (from a commercial source, R&D) none of the peptides were detected by the monoclonal antibodies of the present invention. However the polyclonal antibody detected several peptides. Peptide 9, which did include the amino acid sequence used to generate polyclonal antibodies as described by Ostendorp et al. (EMBO J. 26, 3875, 2007), was clearly detected by the commercially available polyclonal antibody. These results indicate that the monoclonal antibodies of the present invention clearly recognize a different epitope than currently available antibodies.

Further characterization of the binding was done by analysis of RAGE mutants of human sRAGE expressed in E. coli. Monoclonal antibodies 11E6 and 4E5 bind to a region around the C2 domain, since binding is lost in deletion mutants lacking amino acids 235-336 and binding, is apparent in mutant RAGE protein consisting of the amino acids 235-336.

Example 4

Construction, Expression and Purification of the E. Coli RAGE Fragments 4.1. Preparation of Constructs The E. coli RAGE constructs listed in Table 6 were generated as follows. Construct 1 was created by PCR amplification from the template plasmid pcDNA 3 (−) 6.1 C HIS A using the forward primer (atgctacatatgaaaaagacagctatcgcgatt gcagtggcactggctggtttcgctaccg-tagcgcaggccgctcaaaacatcacagcc (SEQ ID NO: 89)) and reverse primer (atgctactcgagtcagtggtggtgg tggtggtgagttc-ccagccctgatcctcccacagagcctgcagttggcccctcc (SEQ ID NO: 90)) which introduced Nde I and Xho I restriction sites which were utilized for subcloning into the analogous sites of pET29. The remaining constructs (#2-#7, Table 6) were generated using Construct 1 as a template. Sequences encoding RAGE amino acid residues 24-129, 24-234, 24-336, 130-234, 130-336, 235-336 were PCR amplified from Construct 1. The resulting DNA fragments were run on a 1.0% agarose gel, and the DNA purified using the QIAquick Gel Extraction Kit from Qiagen. The DNA fragments were digested with NdeI and XhoI, and ligated into similarly digested pET28a. The ligation mix was transformed into Max Efficiency DH5a competent cells and plated onto LB agar plates containing 50 mg/L kanamycin. After overnight incubation at 37° C., three colonies for each clone were inoculated into 3 ml of LB broth containing 50 mg/L kanamycin and shaken overnight at 37° C. The DNA was isolated using the QIAprep Spin Miniprep Kit from Qiagen, and the insert sequenced using T7 promoter and T7 terminator specific primers. The DNA sequence of the plasmids encoding constructs #1-#7 are listed as SEQ ID NOs: 27-33, and the corresponding translated regions are listed as SEQ ID NOs: 34-40.

TABLE 6

| RAGE constructs | | | |
|---|---|---|---|
| Construct # | Protein Form Name | Protein SEQ ID | Plasmid SEQ ID |
| 1 | OmpA-[RAGE (23-340)]-6His | 34 | 27 |
| 2 | 6His-(Thr)-[RAGE (24-129)] | 35 | 28 |
| 3 | 6His-(Thr)-[RAGE (24-234)] | 36 | 29 |
| 4 | 6His-(Thr)-[RAGE (24-336)] | 37 | 30 |
| 5 | 6His-(Thr)-[RAGE (130-234)] | 38 | 31 |
| 6 | 6His-(Thr)-[RAGE (130-336)] | 39 | 32 |
| 7 | 6His-(Thr)-[RAGE (235-336)] | 40 | 33 |

E. coli strain BL21(DE3) was transformed with Construct #1 plasmid DNA, plated on LB plates containing kanamycin (50 mg/L), and incubated at 37° C. overnight. The next day 14 fernbach flasks, each containing 1 L of Terrific Broth with kanamycin (50 mg/L), were inoculated with a CFU and placed shaking (180 rpm) in an incubator at 37° C. When the cultures reached an $OD_{600nm}$ of 0.47, the flasks were transferred to a 30° C. incubator (still shaking at 180 rpm) and expression was induced by addition of 0.4 mM IPTG. Cells were harvested 4 hours after induction by centrifugation (15,900 g, 8 minutes, 4° C.), and the cell paste then frozen at −80° C. until purification.

Purification of RAGE Construct 1 proceeded by first thawing and resuspending an ~20 g cell pellet in 180 ml of lysis buffer [50 mM Tris pH 7.6, 300 mM NaCl, 10% glycerol, 0.1% Triton X-100, 0.5 mM $MgCl_2$, 20 mM imidazole, 1× Roche EDTA-free protease inhibitors, 20 U/ml DNase I]. Cells were lysed by passing the suspension three consecutive times through an Avestin Emulsiflex microfluidizer at 3° C. Clarified lysate was then loaded onto a 5 ml HiTrap IMAC-column (GE Healthcare, 17-5255-01) at 2 ml/min. The column was then washed with 10 CV of wash buffer [50 mM Tris pH 7.6, 300 mM NaCl, 10% glycerol, 20 mM imidazole]. Following the wash step, RAGE was gradient eluted using elution buffer [50 mM Tris pH 7.6, 300 mM NaCl, 10% glycerol, 500 mM imidazole]. Fractions containing RAGE were pooled and then dialyzed against 50 mM Tris pH 7.6, mM NaCl, 10% glycerol. Mass-spec analysis of the purified material confirmed the OmpA-leader had been processed off and that the purified material began with residue 23 of RAGE (i.e. the sequence A-Q-N- . . . ) as expected.

Plasmids encoding Constructs #2-#7 were separately transformed into *E. coli* strain BL21(DE3), plated onto LB plates containing kanamycin (50 mg/L), and incubated at 37° C. overnight. The next day 1 L of Overnight Express Instant TB Medium (Novagen) was inoculated with a colony and shaken for 19 hours at 30° C. The cells were pelleted by centrifugation (15,900×g, 10 minutes, 4° C.) and then frozen at −80° C. The pellets (5-6 grams each) were thawed and resuspended in 50 ml of lysis buffer [50 mM Tris, pH 8, 300 mM NaCl, 0.1% Triton X-100, 10% glycerol, 0.2 mg/ml lysozyme, 1 ml of protease inhibitor cocktail set III (Calbiochem), 20 U/ml benzonase, 5 mM B-mercaptoethanol]. The lysates were sonicated on a Vibra Cell Sonicator for 2 minutes, followed by centrifugation at 20K×g for 30 minutes. Econo-Pac 10 columns from Bio-Rad were filled with a 2 ml bed volume of ProBond Nickel Resin and equilibrated with lysis buffer. The clarified lysates were passed through the columns 3 consecutive times, followed by washing with 3×10 column volumes (60 ml total) of wash buffer [2×PBS, 20 mM imidazole, 10% glycerol, 5 mM B-mercaptoethanol]. The proteins were eluted off the columns with 5×1 column volume (10 ml total) of elution buffer [2×PBS, 500 mM imidazole, 10% glycerol, 5 mM B-mercaptoethanol]. The eluted material was transferred into PBS, 10% glycerol, and 1 mM DTT using Bio-Rad Econo-Pac 10DG Columns 4.2. Expression of Anti-RAGE Monoclonal Antibodies 11E6, 4E5 and 7F9

The media used for hybridoma cell expansion consisted of BD Cell MAb Quantum Yield Medium (Becton Dickenson—catalog #220511) containing 10% ultra low IgG fetal bovine serum (Invitrogen—catalog #16250-078). Briefly, multiple 300 ml seed cultures of the murine hybridoma cell line expressing RAGE monoclonal antibody 11E6 were expanded in a 2 L roller bottle shaking in an incubator (65 rpm, 8% $CO_2$, 37° C.) until reaching a density of $1.0 \times 10^6$ cell/ml. Cells were then seeded into 20 L of media at a density $0.06 \times 10^6$ cells/mL in a 25 L Wave BioReactor with operational settings of 14 rocks/minute, a rock angle of 6°, temperature of 37° C., and an 8% $CO_2$ sparge-rate of 0.15 Lpm. After two days, the culture was further expanded by addition of media to a final volume of 24 L, resulting in a new cell density of $0.43 \times 10^6$ cells/mL. The culture was harvested 12 days after being expanded to full volume. Cells were removed by continuous centrifugation (Carr ViaFuge, 6000 rpm, 1.7 Lpm). After addition of 5 mM $NaN_3$ (from a 1 M $NaN_3$ stock—Hampton Research) to the clarified media, the material immediately was utilized in the purification process.

The media used for hybridoma cell expansion consisted of BD Cell MAb Quantum Yield Medium (Becton Dickenson—catalog #220511) containing 10% ultra low IgG fetal bovine serum (Invitrogen—catalog #16250-078). Briefly, multiple 300 ml seed cultures of the murine hybridoma cell line expressing RAGE monoclonal antibody 4E5 were expanded in a 2 L roller bottle shaking in an incubator (65 rpm, 8% $CO_2$, 37° C.) until reaching a density of $1.0 \times 10^6$ cell/ml. Cells were then seeded into 5 L of media at a density $0.12 \times 10^6$ cells/mL in a 25 L Wave BioReactor with operational settings of 12 rocks/minute, a rock angle of 6°, temperature of 37° C., and an 8% $CO_2$ sparge-rate of 0.15 Lpm. After four days, the culture was further expanded by addition of media to a final volume of 24 L, resulting in a new cell density of $0.24 \times 10^6$ cells/mL. The rock-rate was increased to 14 rocks/minute. The culture was harvested 12 days after being expanded to full volume. Cells were removed by continuous centrifugation (Carr ViaFuge, 6000 rpm, 1.7 Lpm). After addition of 5 mM $NaN_3$ (from a 1 M $NaN_3$ stock—Hampton Research) to the clarified media, the material immediately was utilized in the purification process.

The media used for hybridoma cell expansion consisted of BD Cell MAb Quantum Yield Medium (Becton Dickenson—catalog #220511) containing 10% ultra low IgG fetal bovine serum (Invitrogen—catalog #16250-078). Briefly, multiple 300 ml seed cultures of the murine hybridoma cell line expressing RAGE monoclonal antibody 7F9 were expanded in a 2 L roller bottle shaking in an incubator (65 rpm, 8% $CO_2$, 37° C.) until reaching a density of $1.0 \times 10^6$ cell/ml. Cells were then seeded into 10 L of media at a density $0.05 \times 10^6$ cells/mL in a 25 L Wave BioReactor with operational settings of 12 rocks/minute, a rock angle of 6°, temperature of 37° C., and an 8% $CO_2$ sparge-rate of 0.15 Lpm. After four days, the culture was further expanded by addition of media to a final volume of 25 L, resulting in a new cell density of $0.25 \times 10^6$ cells/mL. The rock-rate was increased to 14 rocks/minute. The culture was harvested 10 days after being expanded to full volume. Cells were removed by continuous centrifugation (Carr ViaFuge, 6000 rpm, 1.7 Lpm). After addition of 5 mM $NaN_3$ (from a 1 M $NaN_3$ stock—Hampton Research) to the clarified media, the material immediately was utilized in the purification process.

4.3. Purification of Anti RAGE Monoclonal Antibodies 11E6, 4E5, 7F9

To the clarified hybridoma culture media, glycine and NaCl were added to final concentrations of 3M and 1.5M, respectively. The pH was adjusted to 8.0 with NaOH. Material is filtered using a 5 μm Pall Capsule #120 membrane filter and loaded onto a 200 mL BioSepra Protein A column. Protein solution was washed with 11 CV of wash buffer (20 mM sodium phosphate pH 8.0, 1 mM sodium azide) and eluted using a step gradient of 50 mM glycine (pH 3.0). Fractions of 100 mL size were collected and protein concentration determined by measuring the A280 nm. All column-processing steps were run at 4° C. Pooled material was dialyzed against 20 L of 10 mM Tris pH 8.0 overnight at 4° C. Further chromatographic polishing was achieved using a SartoBind Q strong basic anion exchanger Singlesep Mini cartridge (Sartorius) in flow through mode at 10 mL/min. The antibody does not bind the column and is collected as one pool. Following this step, the material was concentrated to 5 mg/ml using an Amicon stirred pressure cell (5000 MWCO membrane, 75 psi, 4° C.). Finally, the antibody was dialyzed two times against 20 L of PBS buffer (10 mM phophate, 0.138 M NaCl, 0.0027 M KCl, pH 7.4), each cycle for 24 h at 4° C.

4.4. ELISA Binding Experiments:

Antigens (purified construct #1-7 proteins) were diluted into Coating Buffer [100 mM NaHCO$_3$, pH 8.2] to 1 µg/ml, and 100 µl of the resulting solution was then aliquoted into a 96-well Nunc Immuno Plate (Maxi-Sorb Surface, flat bottom, catalog #439454). The plate was sealed with sealing film and incubated at 4° C. overnight. The next day, the plate wells were each washed 3 times with 150 µL PBST buffer [Sigma PBS+0.05% Tween 20]. Then 300 ul of blocking solution (3% NFDM in PBST) was added to each well. The plate was incubated for 2 hours at room temperature and shaking at 100 rpm. After the incubation step, each well was again washed three times with 150 µL PBST. 100 ul of the corresponding antibody to be tested (i.e. 7F9, 11E6, and 4E5) was added at various dilutions made in PBST/0.5% BSA. The plate was then sealed with sealing film and incubated for 2 hours at room temperature and shaking at 100 rpm. Next the antibody solution was drained out of the wells, and each well then washed three times with 200 ul PBST. To each well then 200 ul of a 1:5000 dilution (in PBST/1% NFDM) of conjugated secondary antibody [Donkey anti-mouse HRPO conjugate, Jackson Immuno Research, Catalog #715-035-150] was added. The plate was covered and allowed to incubate for 1 hour at room temperature while shaking at 100 rpm. Following this incubation, the solution was removed from the wells and each well was washed three times with 200 ul PBST. To each well 100 µL of HRPO substrate [3,3',5',5'-Tetramethylbenzidine Liquid Substrate (TMB), Supersensitive for ELISA, Sigma Catalog #T4444] solution was added and the plate incubated at room temperature for 10 minutes. Finally, 50 µL of 2M H$_2$SO$_4$ was added to each well to stop the reaction and the A$_{540nm}$ of each well was measured using a microtiter plate reader.

Figure 3C:
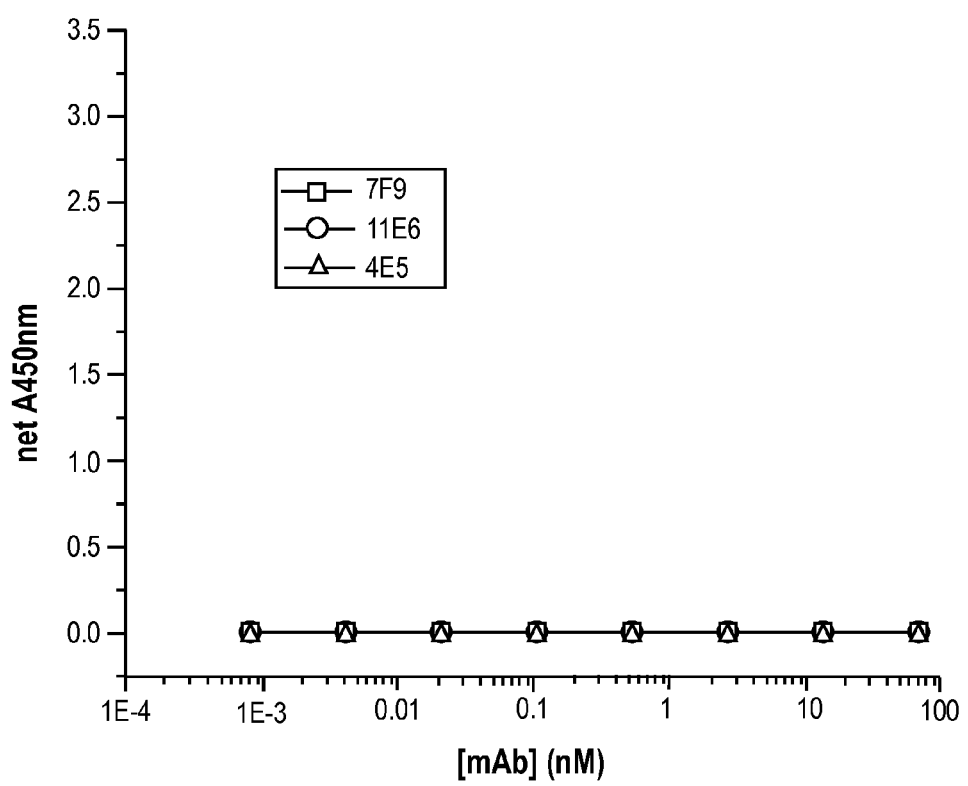
Figure 4A:
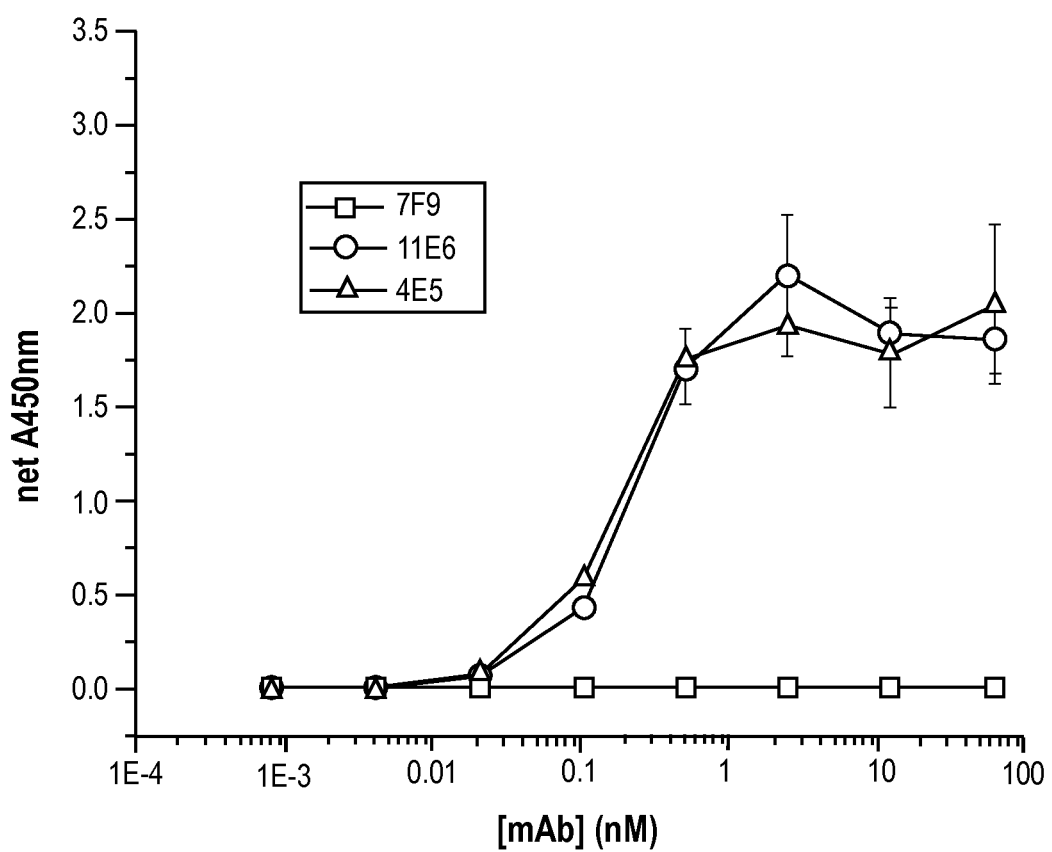
FIGS. 4A-4C show ELISA binding experiments of monoclonal antibodies of the invention to different RAGE fragments.
Figure 4B:
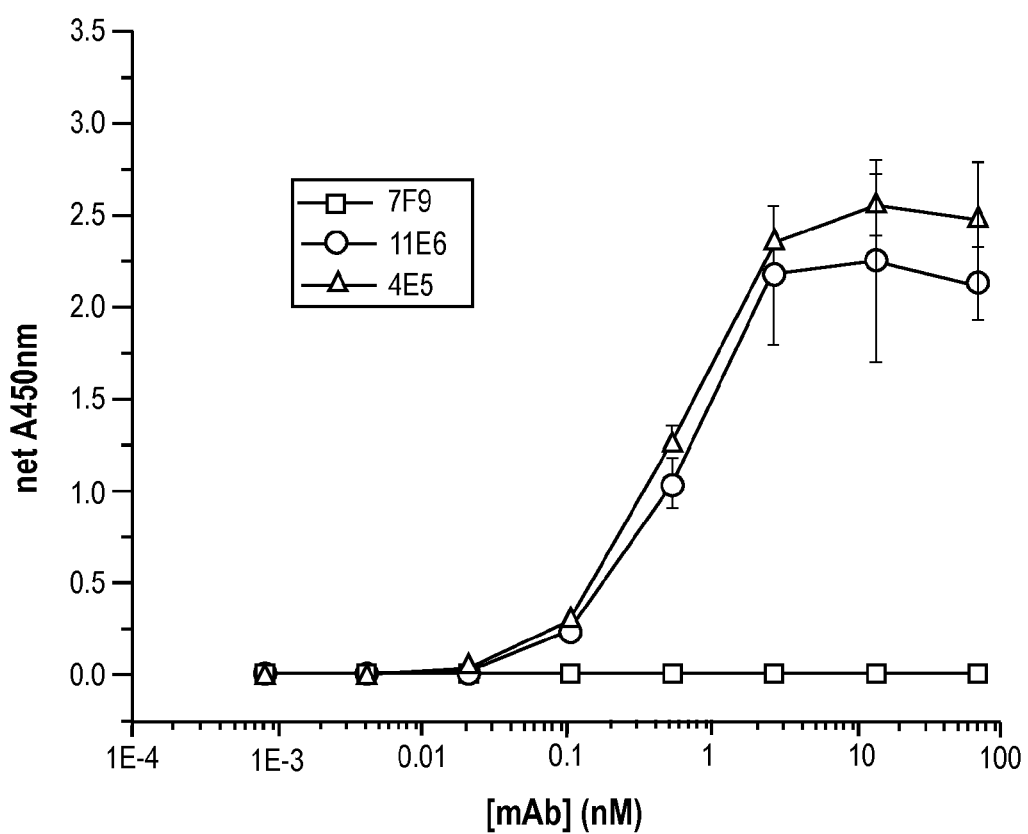
Figure 4C:
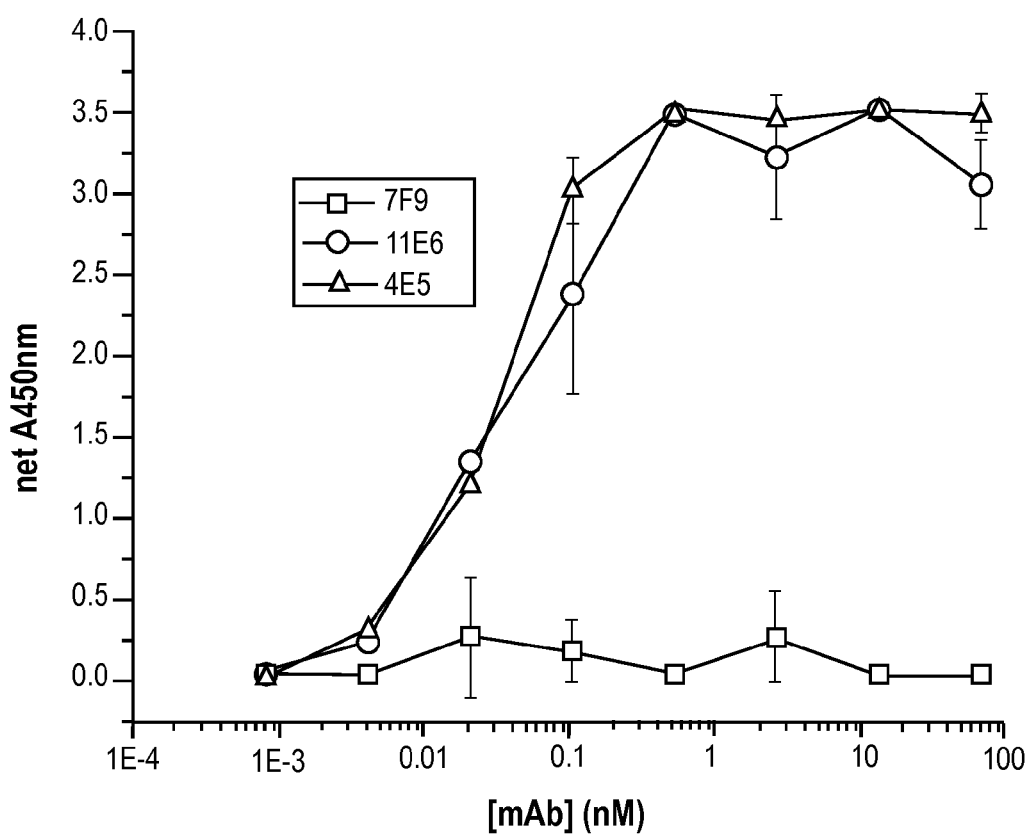

Results of these binding experiments are shown in FIGS. 3A, 3B and 3C, and FIGS. 4A, 4B, and 4C. FIGS. 3A, 3B, and 3C shows that RAGE residues 24-234 were not involved in binding of RAGE monoclonal antibodies 11E6, 4E5, or 7F9. Conversely, as shown in FIGS. 4A, 4B, and 4C, RAGE residues 235-336 were sufficient for binding of RAGE monoclonal antibodies 11E6 and 4E5. RAGE mAb 7F9 did not show any binding to any of these (*E. coli* expressed) RAGE fragments.

Example 5

Epitope Mapping

5.1. Immobilization of the 11E6, 4E5 and 7F9 Antibodies

Approximately 20 mg of CNBr-activated Sepharose fast flow resin was weighed into three compact reaction columns fitted with 35 µm frits. The resins were permitted to swell in 200 µL of 1 mM HCl before washing 3 times with 200 µL of 1 mM HCl. The resins were subsequently rinsed 3 times with 200 µL of 100 mM sodium bicarbonate buffer (pH 8.3) containing 500 mM sodium chloride (buffer A). Once completed, the solutions were flushed from the columns so that only a thin layer of buffer remained on the surface of each resin. Approximately 5.5 nmoles of the antibodies were immobilized to the resins, which required the addition of 235 µL of 7F9 (3.4 mg/mL), 500 µL of 11E6 (1.6 mg/mL), and 200 µL of 4E5 (3.75 mg/mL). For the 7F9 and 4E5 antibody immobilizations, 200 µL of buffer A was also included. The compact reaction columns were sealed and permitted to mix through inversion at room temperature for 4 hours. Once completed, the compact reaction columns were unsealed and flushed with three additions of 200 µL of buffer A to remove unbound antibody. After the flush, 200 µL of a buffer containing 100 mM Tris-HCl (pH 8) and 500 mM sodium chloride (buffer B) was added to each column. The columns were resealed and allowed to mix through inversion at room temperature to block unbound but activated sites on the resins. After 2 hours, the columns were unsealed and flushed first with 200 µL of 100 mM sodium acetate buffer (pH 4) containing 500 mM sodium chloride (buffer C) followed by 200 µL of buffer B. This process was repeated an additional two times to ensure complete removal of unbound antibody and to fully block the remaining sites of attachment on the resins. The resins were then washed four times with 200 µL of 100 mM sodium bicarbonate buffer (pH 8.3) containing 100 mM sodium chloride (buffer D) prior to coupling the antigen.

5.2. Proteolytic Excision of the *E. coli* and BacMam-Expressed sRAGE Antigens The sRAGE antigens were permitted to bind to the antibody columns by adding 75 µL of the *E. coli*-expressed antigen to the 11E6 and 4E5 resins and adding 125 µL of the BacMam-expressed antigen to the 11E6, 4E5 and 7E9 resins. The columns were sealed and the samples allowed to mix by inversion at room temperature for 2 hours. After this time, the columns were unsealed and flushed with 4 additions of 200 µL of buffer D. After flushing through the rinses, the resins were resuspended in 200 µL of buffer D as well as with the proteases, generated as 0.1 mg/mL solutions of either Trypsin, endoproteinase Glu-C or Chymotrypsin. The amounts of the proteases varied between the experiments to attenuate the digestions, but ranged from 200-400 fold excess of the antigen over the protease by weight. Proteolysis was permitted to occur at room temperature with mixing by inversion for 12 hours. After this time, the columns were unsealed and the proteolytic solution was flushed through and saved for further analysis. For samples subjected to dual digestion, the resins were resuspended in 200 µL of buffer D and a second protease before the next steps. For those samples not treated in a second protease, the columns were subjected to two individual 200 µL washes in buffer D followed by a 200 µL wash in buffer A then a final 200 µL wash in buffer D. Each wash was retained separately for later analysis. The epitope containing peptides were eluted from the column with three individual 200 µL washes in 2% formic acid. Each elution sample was retained separately for later analysis.

5.3. Mass Spectrometry Analysis of the Epitope-Containing Peptides

The samples were analyzed using both a Bruker Apex QE 7T Fourier-Transform Ion Cyclotron Resonance (FT-ICR) mass spectrometer as well as an Applied Biosystems Q-STAR Pulsar I mass spectrometer. For the FT-ICR mass spectrometric analysis, 8 µL of the epitope excision samples were injected onto a Jupiter C4 reversed phase column (0.5×150 mm, 5µ particle size, 300 Å pore size) by an Agilent series 1100 capillary HPLC. The samples were washed for 5 minutes in 90% water with 0.1% formic acid (solvent A)/10% acetonitrile with 0.1% formic acid (solvent B) at a 5 µL/min flow rate to desalt. The peptides were eluted into the mass spectrometer by changing the mobile phase composition to 5% solvent A/95% solvent B. Samples requiring direct infusion for tandem mass spectrometry were injected onto a protein Microtrap (Michrom) equilibrated in 98% water, 1% acetonitrile and 1% formic acid. The samples were washed with 1 mL of the equilibration solvent before being eluted in 300 µL of 60% acetonitrile, 40% water and 0.1% formic acid. The eluent was directly infused into the FT-ICR mass spectrometer at 2 µL/min. For the Q-STAR Pulsar mass spectrometer, between 5-30 µL of sample was injected onto a protein Microtrap (Michrom) by an Agilent series 1100 HPLC. The samples were washed in 95% solvent A/5% solvent B for 1 minute prior to elution of the bound peptides into the mass spectrometer in 5% solvent A/95% solvent B.

Proteolytic excision of the *E. coli*-expressed sRAGE bound to the 11E6 antibody and elution of epitope-containing peptides revealed the presence of a peptide with a mass of 12,204.5 Da. Mass selection and collisionally-activated dissociation of the 10$^+$ charge state confirmed the identity of this peptide, which corresponded to the residues Val$^{229}$-His$^{346}$ (this His residue is due to adding the Hexa-His-tag to the sRAGE protein). Further epitope mapping using Trypsin followed by Chymotrypsin proteolysis revealed cleavage of the C-terminal hexahistidine tag, thus refining the epitope to residues Val$^{229}$-His$^{341}$ (this His residue is due to adding the Hexa-His-tag to the sRAGE protein). No further refinement of this epitope could be obtained using proteolysis. Similarly executed proteolytic excision of the *E. coli*-expressed sRAGE bound to the 4E5 antibody revealed the same peptide of 12,204.5 Da that was observed for the 11E6 antibody epitope. Correspondingly, excision of the BacMam-expressed sRAGE bound to either the 11E6 or 4E5 antibody revealed two major epitope containing peptides of masses 10,671.9 Da and 10,614.0 Da. These peptides match to the C-terminal of the BacMam-expressed construct, spanning residues Val$^{229}$-Gly$^{331}$ and Val$^{229}$-Ala$^{330}$, respectively.

Proteolytic excision of the BacMam-expressed sRAGE bound to the 7F9 antibody and elution of epitope-containing peptides revealed multiple species representing several overlapping peptides. Deconvolution of the mass spectrum revealed peptides of masses 12,079.6 Da, 12,372.9 Da, 13,477.3 Da and 24,132.3 Da. These masses match to residues Asn$^{105}$-Arg$^{216}$, Asn$^{105}$-Arg$^{218}$, Asn$^{105}$-Arg$^{228}$ and Asn$^{105}$-Gly$^{331}$, respectively, suggesting a minimal epitope spanning residues Asn$^{105}$-Arg$^{216}$.

These results indicate that antibodies 11E6 and 4E5 possess epitopes on the C-termini of both *E. coli* and BacMam-expressed sRAGE, and that antibody 7F9 recognizes an epitope on the center domain of BacMam-expressed sRAGE.

Example 6

Biacore and Surface Plasmon Resonance Measurements

The affinity of the three monoclonal antibodies of the present invention, i.e. 7F9, 11E6 and 4E5, was measured using Biacore and surface plasmon resonance measurements.

6.1. Materials and Methods for Anti-RAGE Binding Kinetic Determinations:

Biacore 2000 instrument was used to measure mouse anti-RAGE mAb binding kinetics. The assay format for mAb affinity analysis was Fc-based capture via immobilized anti-Fc antibodies. A standard amine coupling protocol was employed to immobilize Fc-specific IgG via primary amines to the carboxy-methyl (CM) dextran surface of CM5 sensor-chips (Biacore). For the study of mouse anti-RAGE mAbs, anti-mouse Fc (Biacore, anti-mouse, BR-1005-14) was used as the immobilized capture reagent. An automated protocol, available on the Biacore 2000, was used to immobilize 8000-10000RU of capture reagent in all 4 flowcells of the sensor-chip. Briefly, the CM-dextran surfaces were activated by freshly prepared 1:1 50 mM N-hydroxysuccinimide (NHS): 200 mM 3-(N,N-dimethylamino) propyl-N-ethylcarbodiimide (EDC). Then the anti-Fc IgG capture reagent (20 ug/ml in 10 mM sodium acetate, pH4.5) was applied to the surface followed by deactivation of the surface and blocking of the residual reactive sites with 1M ethanolamine (pH 8.5).

The running buffer employed was HBS-EP+ [10 mM HEPES, pH 7.4, 150 mM NaCl, 3 mM EDTA, 0.05% P20 surfactant (Biacore)] for the mouse anti-RAGE mAbs. Each experimental cycle consisted of the following steps: 1) anti-RAGE mAbs were captured in flowcells 2, 3 or 4 to a level of 50-200RU (depending on the antigen). All measurements were referenced against flowcell 1 which had no captured anti-RAGE mAb. 2) Antigen was injected through all 4 flowcells, 180 ul at 60 ul/min. After the antigen injection, dissociation was monitored for 600 seconds at 60 ul/min. 3) The anti-Fc capture surface was regenerated with low pH glycine. For kinetic determinations, RAGE injections were a 2 fold dilution series from 20 nM-0.31 nM and buffer only in randomized duplicates.

6.2. Evaluation and Results

Data were processed using Biacore evaluation software. Briefly, the data were double referenced by first, subtracting the signal from the reference cell and second, by subtracting the signal from buffer-only injections. The double referenced data from the RAGE injection series were then fit globally to a 1:1 (Langmuir) binding model, which included a mass transfer term, to determine the binding kinetic rate constants, ka and kd, and the affinity, $K_D$.

Table 7 shows that 4E5 did not bind to mouse RAGE (Mu-RAGE). 11E6 and 4E5 cross-competed with each other for binding to RAGE. 7F9 does not bind to RAGE produced in *E. coli* lacking glycosylation.

Table 7 also shows the specific epitopes to which the three antibodies of the present invention bound to human RAGE, via epitope mapping using protection of human sRAGE from proteolytic digestion and identification of the protected peptides with mass spectrometry. MAb 7F9 bound to C1 (Asn$^{105}$-Pro$^{215}$); mAb 4E5 bound to C2 (Val$^{229}$-Thr$^{340}$ in *E. coli* RAGE; Val$^{229}$-Gly$^{331}$ in husRAGE produced in mammalian cells), and 11E6 bound to C2 (Val$^{238}$-Arg$^{314}$ in *E. coli* RAGE; Val$^{229}$-Gly$^{331}$ in husRAGE produced in mammalian cells).

TABLE 7

| Mab | Affinity (nM) | Epitope | Mouse-RAGE |
|---|---|---|---|
| 7F9 | 0.11 | C1; glycosylation sensitive | + |
| 11E6 | 0.29 | C2; overlap with 4E5 | + |
| 4E5 | 2.2 | C2; overlap with 11E6 | − | epitopes to which the antibodies are binding

Example 7

Construction of CDR-Grafted Antibodies

By applying standard methods well known in the art, the CDR sequences of VH and VL chains of monoclonal antibody 11E6 (see Table 4 above) are grafted into different different human heavy and light chain acceptor sequences. Based on sequence VH and VL alignments with the VH and VL sequences of monoclonal antibody 11E6 of the present invention the following known human sequences are selected:
  a) VH7-4.1 and VH1-2 as well as the joining sequences hJH6 for constructing heavy chain acceptor sequences (according to Table 2 above);
  b) 1-12/L5 and 3-15/L2 as well as hJK2 for constructing light chain acceptor sequences (according to Table 3 above).

By grafting the corresponding VH and VL CDRs of 11E6 into said acceptor sequences the following CDR grafted, humanized, modified VH and VL sequences were prepared (see also Table 5, above): VH 11E6.1-GL, VH 11E6.2-GL, VL 11E6.1-GL and VL 11E6.2-GL.

Example 8

Construction of Framework Back Mutations in CDR-Grafted Antibodies

To generate humanized antibody framework mutations, mutations are introduced into the CDR-grafted antibodies using de novo synthesis of variable domains and/or mutagenic primers and PCR, using methods well known in the art. Different combinations of back mutations and other mutations are constructed for each of the CDR-grafts as follows.

For heavy chain VH 11E6.1-GL one or more of the following Vernier and VH/VL interfacing residues are back mutated as follows: V2→I and/or Y95→F.

For heavy chain VH 11E6.2-GL one or more of the following Vernier and VH/VL interfacing residues are back mutated as follows: V2→I, V68→F, M70→F, R72→L, Y95→F.

For light chain VL 11E6.1-GL one or more of the following Vernier and VH/VL interfacing residues are back mutated as follows: A43→S, Y49→F, Y87→F.

For light chain VL 11E6.2-GL one or more of the following Vernier and VH/VL interfacing residues are back mutated as follows: A43→S, Y49→F, I58→V, Y87→F.

Additional mutations include the following:
for heavy chain
VH 11E6.1-GL, Q1→E, and for
VH 11E6.2-GL, Q1→E, I76→T, R85→S, D89→E;
for light chain
VL 11E6.1-GL, V11→L, and
VL 11E6.2-GL, V13→L, E70→D.

Example 9

Construction and Expression of Recombinant Humanized Anti RAGE Antibodies pHybE expression vectors harboring heavy and light chains containing framework back mutations were co-transfected into 293-6E cells to transiently produce full-length humanized antibodies. Mutations were introduced into the CDR-grafted antibody sequences as prepared according to Example 7, by de novo synthesis of the variable domain and/or using mutagenic primers and PCR, and methods well known in the art. The amino acid sequences of the VH and VL regions of the humanized antibodies are disclosed in Table 8.

TABLE 8

Expression of humanized antibodies

| SEQ ID NO | Protein region | Sequence 123456789012345678901234567890 |
|---|---|---|
| 62 | VH h11E6.1 | EVQLVQSGSELKKPGASVKVSCKASGYTFTNFGMNWVRQAPGQGLEWMGYINTNTGESIY SEEFKGRFVFSLDTSVSTAYLQICSLKAED TAVYYCARSRMVTAYGMDYWGQGTTVTSS |
| 63 | VL h11E6.1 | DIQMTQSPSSLSASVGDRVTITCKASQNVG TAVAWYQQKPGKAPKLLIYSASNRYTGVPS RFSGSGSGTDFTLTISSLQPEDFATYYCQQ YSSYPLTFGQGTKLEIKR |

TABLE 8-continued

Expression of humanized antibodies

| SEQ ID NO | Protein region | Sequence 123456789012345678901234567890 |
|---|---|---|
| 62 | VH h11E6.2 | EVQLVQSGSELKKPGASVKVSCKASGYTFTNFGMNWVRQAPGQGLEWMGYINTNTGESIY SEEFKGRFVFSLDTSVSTAYLQICSLKAED TAVYYCARSRMVTAYGMDYWGQGTTVTSS |
| 64 | VL h11E6.2 | DIQMTQSPSSLSASVGDRVTITCKASQNVG TAVAWYQQKPGKSPKLLIFSASNRYTGVPS RFSGSGSGTDFTLTISSLQPEDFATYFCQQ YSSYPLTFGQGTKLEIKR |
| 62 | VH h11E6.3 | EVQLVQSGSELKKPGASVKVSCKASGYTFTNFGMNWVRQAPGQGLEWMGYINTNTGESIY SEEFKGRFVFSLDTSVSTAYLQICSLKAED TAVYYCARSRMVTAYGMDYWGQGTTVTSS |
| 65 | VL h11E6.3 | EIVMTQSPATLSLSPGERATLSCKASQNVG TAVAWYQQKPGQAPRLLIYSASNRYTGIPA RFSGSGSGTDFTLTISSLQSEDFAVYYCQQ YSSYPLTFGQGTKLEIKR |
| 62 | VH h11E6.4 | EVQLVQSGSELKKPGASVKVSCKASGYTFTNFGMNWVRQAPGQGLEWMGYINTNTGESIY SEEFKGRFVFSLDTSVSTAYLQICSLKAED TAVYYCARSRMVTAYGMDYWGQGTTVTSS |
| 66 | VL h11E6.4 | EIVMTQSPATLSLSPGERATLSCKASQNVG TAVAWYQQKPGQSPRLLIFSASNRYTGVPA RFSGSGSGTDFTLTISSLQSEDFAVYFCQQ YSSYPLTFGQGTKLEIKR |
| 67 | VH h11E6.5 | EIQLVQSGSELKKPGASVKVSCKASGYTFTNFGMNWVRQAPGQGLEWMGYINTNTGESIY SEEFKGRFVFSLDTSVSTAYLQICSLKAED TAVYFCARSRMVTAYGMDYWGQGTTVTSS |
| 63 | VL h11E6.5 | DIQMTQSPSSLSASVGDRVTITCKASQNVG TAVAWYQQKPGKAPKLLIYSASNRYTGVPS RFSGSGSGTDFTLTISSLQPEDFATYYCQQ YSSYPLTFGQGTKLEIKR |
| 67 | VH h11E6.6 | EIQLVQSGSELKKPGASVKVSCKASGYTFTNFGMNWVRQAPGQGLEWMGYINTNTGESIY SEEFKGRFVFSLDTSVSTAYLQICSLKAED TAVYFCARSRMVTAYGMDYWGQGTTVTSS |
| 64 | VL h11E6.6 | DIQMTQSPSSLSASVGDRVTITCKASQNVG TAVAWYQQKPGKSPKLLIFSASNRYTGVPS RFSGSGSGTDFTLTISSLQPEDFATYFCQQ YSSYPLTFGQGTKLEIKR |
| 67 | VH h11E6.7 | EIQLVQSGSELKKPGASVKVSCKASGYTFTNFGMNWVRQAPGQGLEWMGYINTNTGESIY SEEFKGRFVFSLDTSVSTAYLQICSLKAED TAVYFCARSRMVTAYGMDYWGQGTTVTSS |
| 65 | VL h11E6.7 | EIVMTQSPATLSLSPGERATLSCKASQNVG TAVAWYQQKPGQAPRLLIYSASNRYTGIPA RFSGSGSGTDFTLTISSLQSEDFAVYYCQQ YSSYPLTFGQGTKLEIKR |
| 67 | VH h11E6.8 | EIQLVQSGSELKKPGASVKVSCKASGYTFTNFGMNWVRQAPGQGLEWMGYINTNTGESIY SEEFKGRFVFSLDTSVSTAYLQICSLKAED TAVYFCARSRMVTAYGMDYWGQGTTVTSS |
| 66 | VL h11E6.8 | EIVMTQSPATLSLSPGERATLSCKASQNVG TAVAWYQQKPGQSPRLLIFSASNRYTGVPA RFSGSGSGTDFTLTISSLQSEDFAVYFCQQ YSSYPLTFGQGTKLEIKR |
| 68 | VH h11E6.9 | EVQLVQSGAEVKKPGASVKVSCKASGYTFTNFGMNWVRQAPGQGLEWMGYINTNTGESIY SEEFKGRVTMTRDTSTSTAYMELSSLRSED TAVYYCARSRMVTAYGMDYWGQGSVTVSS |

TABLE 8-continued

Expression of humanized antibodies

| SEQ ID NO | Protein region | Sequence 123456789012345678901234567890 |
|---|---|---|
| 63 | VL h11E6.9 | DIQMTQSPSSLSASVGDRVTITCKASQNVGTAVAWYQQKPGKAPKLLIYSASNRYTGVPSRFSGSGSGTDFTLTISSLQPEDFATYYCQQYSSYPLTFGQGTKLEIKR |
| 68 | VH h11E6.10 | EVQLVQSGAEVKKPGASVKVSCKASGYTFTNFGMNWVRQAPGQGLEWMGYINTNTGESIYSEEFKGRVTMTRDTSTSTAYMELSSLRSEDTAVYYCARSRMVTAYGMDYWGQGTSVTVSS |
| 64 | VL h11E6.10 | DIQMTQSPSSLSASVGDRVTITCKASQNVGTAVAWYQQKPGKSPKLLIFSASNRYTGVPSRFSGSGSGTDFTLTISSLQPEDFATYFCQQYSSYPLTFGQGTKLEIKR |
| 68 | VH h11E6.11 | EVQLVQSGAEVKKPGASVKVSCKASGYTFTNFGMNWVRQAPGQGLEWMGYINTNTGESIYSEEFKGRVTMTRDTSTSTAYMELSSLRSEDTAVYYCARSRMVTAYGMDYWGQGTSVTVSS |
| 65 | VL h11E6.11 | EIVMTQSPATLSLSPGERATLSCKASQNVGTAVAWYQQKPGQAPRLLIYSASNRYTGIPARFSGSGSGTDFTLTISSLQSEDFAVYYCQQYSSYPLTFGQGTKLEIKR |
| 68 | VH h11E6.12 | EVQLVQSGAEVKKPGASVKVSCKASGYTFTNFGMNWVRQAPGQGLEWMGYINTNTGESIYSEEFKGRVTMTRDTSTSTAYMELSSLRSEDTAVYYCARSRMVTAYGMDYWGQGTSVTVSS |
| 66 | VL h11E6.12 | EIVMTQSPATLSLSPGERATLSCKASQNVGTAVAWYQQKPGQSPRLLIFSASNRYTGVPARFSGSGSGTDFTLTISSLQSEDFAVYFCQQYSSYPLTFGQGTKLEIKR |
| 69 | VH h11E6.13 | EIQLVQSGAEVKKPGASVKVSCKASGYTFTNFGMNWVRQAPGQGLEWMGYINTNTGESIYSEEFKGRFTFTLDTSTSTAYMELSSLRSEDTAVYFCARSRMVTAYGMDYWGQGTSVTVSS |
| 63 | VL h11E6.13 | DIQMTQSPSSLSASVGDRVTITCKASQNVGTAVAWYQQKPGKAPLLIYSASNRYTGVPSRFSGSGSGTDFTLTISSLQPEDFATYYCQQYSSYPLTFGQGTKLEIKR |
| 69 | VH h11E6.14 | EIQLVQSGAEVKKPGASVKVSCKASGYTFTNFGMNWVRQAPGQGLEWMGYINTNTGESIYSEEFKGRFTFTLDTSTSTAYMELSSLRSEDTAVYFCARSRMVTAYGMDYWGQGTSVTVSS |
| 64 | VL h11E6.14 | DIQMTQSPSSLSASVGDRVTITCKASQNVGTAVAWYQQKPGKSPKLLIFSASNRYTGVPSRFSGSGSGTDFTLTISSLQPEDFATYFCQQYSSYPLTFGQGTKLEIKR |
| 69 | VH h11E6.15 | EIQLVQSGAEVKKPGASVKVSCKASGYTFTNFGMNWVRQAPGQGLEWMGYINTNTGESIYSEEFKGRFTFTLDTSTSTAYMELSSLRSEDTAVYFCARSRMVTAYGMDYWGQGTSVTVSS |
| 65 | VL h11E6.15 | EIVMTQSPATLSLSPGERATLSCKASQNVGTAVAWYQQKPGQAPRLLIYSASNRYTGIPARFSGSGSGTDFTLTISSLQSEDFAVYYCQQYSSYPLTFGQGTKLEIKR |
| 69 | VH h11E6.16 | EIQLVQSGAEVKKPGASVKVSCKASGYTFTNFGMNWVRQAPGQGLEWMGYINTNTGESIYSEEFKGRFTFTLDTSTSTAYMELSSLRSEDTAVYFCARSRMVTAYGMDYWGQGTSVTVSS |
| 66 | VL h11E6.16 | EIVMTQSPATLSLSPGERATLSCKASQNVGTAVAWYQQKPGQSPRLLIFSASNRYTGVPARFSGSGSGTDFTLTISSLQSEDFAVYFCQQYSSYPLTFGQGTKLEIKR |

Specifically, for the heavy chains:

VH hi 1E6.1, VH hi 1E6.2, VH hi 1E6.3, and VH h11E6.4 contain VH 11E6.1-GL, with a Q1→E mutation.

VH h11E6.5, VH h11E6.6, VH h11E6.7 and VH h11E6.8 contain VH 11E6.1-GL, with a Q1→E mutation and the following Vernier and VH/VL interfacing residue back mutations: V2→I and Y95→F.

VH h11E6.9, VH h11E6.10, VH h11E6.11, and VH h11E6.12 contain VH 11E6.2-GL, with a Q1→E, I76→T, R85→S, and D89→E mutation.

VH h11E6.13, VH h11E6.14, VH h11E6.15, and VH h11E6.16 contain VH 11E6.2-GL, with a Q1→E, I76→T, R85→S, D89→E mutation and the following Vernier and VH/VL interfacing residue back mutations: V2→I, V68→F, M70→F, R72→L, and Y95→F.

For the light chains:

VL h11E6.1, VL h11E6.5, VL h11E6.9, and VL h11E6.13 contain VL 11E6.1-GL with a V11→L mutation.

VL h11E6.2, VL h11E6.6, VL h11E6.10, and VL h11E6.14 contain VL 11E6.1-GL with a V11→L mutation and the following Vernier and VH/VL interfacing residue back mutations: A43→S, Y49→F, and Y87→F.

VL h11E6.3, VL h11E6.7, VL h11E6.11, and VL h11E6.15 contain VL 11E6.2-GL with V13→L and E70→D mutations.

VL h11E6.4, VL h11E6.8, VL h11E6.12, and VL h11E6.16 contain VL 11E6.2-GL with V13→L and E70→D mutations and the following Vernier and VH/VL interfacing residue back mutations: A43→S, Y49→F, I58→V, and V87→F.

Example 10

Characterization of Humanized 11E6 Antibodies Using Competition ELISA

ELISA plates (Costar 3369) were coated overnight at 4° C. with 50 µl/well of 2 µg/ml hRAGE (1-331) in 0.2 M sodium carbonate-bicarbonate buffer, pH 9.4, washed with Wash Buffer (PBS containing 0.1% Tween 20), and blocked for 1 hr at room temperature with 200 µl/well of 2% nonfat dry milk in PBS. After washing with Wash Buffer, a mixture of a biotinylated m11E6 (0.3 µg/ml final concentration) and unlabelled competitor test antibody starting at 81 µg/ml final concentration and serially diluted 3-fold) in 50 µl/well of ELISA buffer was added in duplicate. After incubating the plates for 1 hr at room temperature, and washing with Wash Buffer, bound antibodies were detected using 100 µl/well of 1:10,000 dilution of HRP-conjugated streptavidin (Fitzgerald) in ELISA buffer. After incubating for 1 hr at room temperature, and washing with Wash Buffer, color development was performed by adding 100 µl/well of TMB Buffer (Zymed). After incubating for 15 min at room temperature, color development was stopped by adding 50 µl/well of 1N hydrochloric acid. Absorbance was read at 490 nm Table 9 shows the $IC_{50}$ values of humanized 11E6 antibodies obtained using the computer software GraphPad Prism (GraphPad Software Inc., San Diego, Calif.).

TABLE 9

$IC_{50}$ values of humanized 11E6 antibodies in a competitive ELISA

| Antibody | $IC_{50}$ (nM) | Antibody | $IC_{50}$ (nM) |
|---|---|---|---|
| h11E6.1 | 19.7 | h11E6.9 | 17.9 |
| h11E6.2 | N/A | h11E6.10 | N/A |
| h11E6.3 | 18.8 | h11E6.11 | 19.9 |
| h11E6.4 | 14.1 | h11E6.12 | 11.3 |
| h11E6.5 | 16.1 | h11E6.13 | 16.8 |
| h11E6.6 | N/A | h11E6.14 | N/A |
| h11E6.7 | 15.5 | h11E6.15 | 14.0 |
| h11E6.8 | 10.8 | h11E6.16 | 9.2 |

Example 11

Determination of Binding Constants for Anti-RAGE mAb Interaction with RAGE

Biacore 2000 and Biacore T100 instruments were used to measure anti-RAGE mAb binding kinetics. The assay format for mAb affinity analysis was Fc-based capture via immobilized anti-Fc antibodies. A standard amine coupling protocol was employed to immobilize Fc-specific IgG via primary amines to the carboxy-methyl (CM) dextran surface of CM5 sensorchips (Biacore). For the study of mouse anti-RAGE mAbs, anti-mouse Fc (Biacore, anti-mouse, BR-1005-14) was used as the immobilized capture reagent and for the study of humanized anti-RAGE mAbs, anti-human Fc (Pierce 31125) was used as the immobilized capture reagent. An automated protocol, available on the Biacore 2000 and Biacore T100, was used to immobilize 8000-10000 RU of capture reagent in all 4 flowcells of the sensorchip. Briefly, the CM-dextran surfaces were activated by freshly prepared 1:1 50 mM N-hydroxysuccinimide (NHS): 200 mM 3-(N,N-dimethylamino) propyl-N-ethylcarbodiimide (EDC). Then the anti-Fc IgG capture reagent (20 ug/ml in 10 mM sodium acetate, pH4.5) was applied to the surface followed by deactivation of the surface and blocking of the residual reactive sites with 1M ethanolamine (pH 8.5).

The running buffer employed was PBS-P [1×PBS (Sigma P3813), pH 7.4, 0.005% P20 surfactant (Biacore)] for the humanized antibodies. Each experimental cycle consisted of the following steps: 1) anti-RAGE mAbs were captured in flowcells 2, 3 or 4 to a level of 50-200 RU (depending on the antigen). All measurements were referenced against flowcell 1 which had no captured anti-RAGE mAb. 2) Antigen was injected through all 4 flowcells, 240 ul at 80 ul/min. After the antigen injection, dissociation was monitored for 600 seconds at 80 ul/min. 3) The anti-Fc capture surface was regenerated with low pH glycine. For kinetic determinations, antigen injections were a 3 fold dilution series from either 30 nM-0.12 nM (for sRAGE [RAGE (1-331)] and buffer only in randomized duplicates.

Data were processed using either Biacore evaluation software or Scrubber 2.0 software (BioLogic Software). Briefly, the data were double referenced by first, subtracting the signal from the reference cell and second, by subtracting the signal from buffer-only injections. The double referenced data for the RAGE injection series were then fit globally to a 1:1 (Langmuir) binding model, which included a mass transfer term, to determine the binding kinetic rate constants, $k_a$ and $k_d$, and the affinity, $K_D$ ($k_a=k_{on}$; $k_d=k_{off}$)

TABLE 10

Biacore data

| 11E6 mAb | $k_{on}$ (M$^{-1}$s$^{-1}$) | $k_{off}$(s$^{-1}$) | $K_D$ (pM) | Resid Stdev |
|---|---|---|---|---|
| h11E6.8 | 2.5E+07 | 8.4E−04 | 33 | 1.6 |
| h11E6.12 | 2.0E+07 | 1.7E−03 | 83 | 1.8 |
| h11E6.16 | 2.8E+07 | 1.4E−03 | 50 | 1.9 |
| mouse 11E6 | 1.8E+07 | 1.3E−03 | 68 | 1.4 |

The $K_D$ values are double-digit pM for all three mAbs and there does not seem to be a significant distinction between the three mAbs regarding their binding kinetics. In a concurrent experiment, the original mouse 11E6 mAb was evaluated with this antigen (human sRAGE 1-331, V#400) and was also double-digit pM $K_D$.

The original mouse 11E6 mAb was previously reported to be 290 pM. However those early experiments used a different buffer system (Biacore buffer HBS-EP+: 10 mM HEPES, pH 7.4, 150 mM NaCl, 3 mM EDTA, 0.05% P20). The buffer choice can, of course, affect the kinetics.

Example 12

Determination of Effect of RAGE Antibody on Chronic Constriction Injury Model of Neuropathic Pain in Mice 12.1 Animals Adult male mice, C57/B16 (Charles River Laboratories, Wilmington, Mass., 250-300 g, n=44) were used in experiments according to the internal Institutional Animal Care and Use Committee guidelines. Housing conditions were temperature-regulated, and under a controlled 12-h light-dark cycle. Food and water were available ad libitum, except during testing.

12.2 Chronic Constriction Injury Model of Neuropathic Pain

Chronic constriction injury (CCI) to the sciatic nerve was performed according to the method described by Bennett and Xie (1988). Mice were placed under isoflurane anesthesia and the right common sciatic nerve was isolated at mid-thigh level. The exposed sciatic nerve was loosely ligated by 4 chromic gut (5-0) ties separated by an interval of 1 mm. Behavioral testing for mechanical threshold was performed two weeks post CCI injury.

12.3 Behavioral Testing

Mechanical threshold was measured using calibrated von Frey monofilaments (Stoelting, Wood Dale, Ill.). Paw withdrawal threshold (PWT) was determined by increasing and decreasing stimulus intensity, and estimated using the Dixon's up-down method (Dixon et al., 1980). Mice were placed individually in inverted plastic containers (20×12.5×20 cm) on top of a suspended wire mesh with a 1 cm$^2$ grid to provide access to the ventral side of the hind paws. Mice were acclimated to the chambers prior to testing. Monofilaments were presented perpendicularly to the plantar surface of the selected hind paw with enough force to cause a slight bend in the filament. Threshold was defined by a withdrawal of the hind paw from the stimulus. CCI-injured mice with threshold scores $\leqq 0.13$ g were considered allodynic, and used in these experiments. Data are expressed as % effect, where 0% was equal to vehicle and 100% was equal to the response measured from the contralateral paw.

12.4 Treatment Groups and Dosing

Monoclonal antibody mAb ML39-11E6 (in PBS) was administered by i.p. injection to mice with allodynia from the chronic constriction injury. Mice received either 30 μg/mouse (n=11) or 100 μg/mouse (n=11) of ML39-11E6 i.p. or 100 μg/mouse of control IgG-1 H35C206 (in PBS, n=11) i.p. on days 1, 3, and 5 of the experiment. Mechanical threshold was measured sixty minutes after dosing on days 1 and 5. Mice were re-tested again on day 8, 72 hours following the last dose of ML39-11E6. Gabapentin (positive control, 100 mg/kg in water, i.p., n=11) was injected acutely 60 minutes prior to testing on days 1, 5, and 8.

12.5 Data Analysis

Data were analyzed and graphs were generated using Prism GraphPad (GraphPad Software, Inc., San Diego, Calif.). Data were analyzed using repeat measures one-way analysis of variance (ANOVA) test. Statistical significance was assumed if P<0.05 (on graph, *P<0.05, **P<0.01).

12.6 Results

Figure 5:
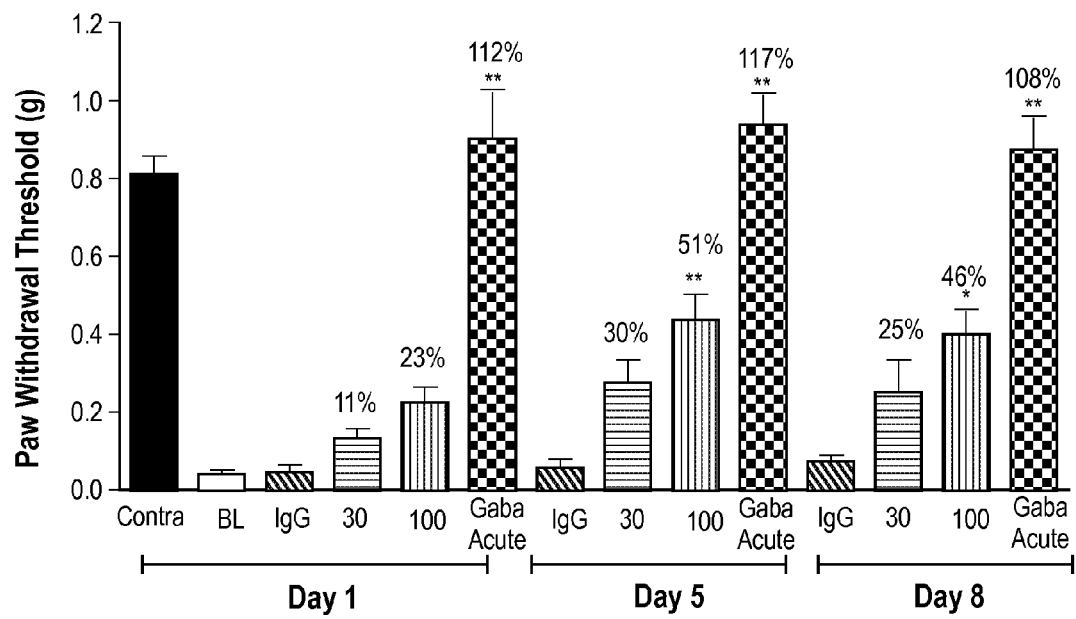
FIG. 5 shows effects of RAGE antibody on Chronic Constriction Injury Model of neuropathic pain in mice. In this FIG. 5, CONTRA refers to contralateral paw tested. BL refers to baseline test.

RAGE antibody, ML39-11E6 attenuated established mechanical allodynia in the chronic constriction injury model of neuropathic pain. The anti-nociceptive efficacy was dose-dependent, observed in a sub-chronic dosing paradigm, and efficacy was maintained 72 hours following the last dose. Anti-nociceptive efficacy of RAGE antibody in the CCI pain model was observed following systemic administration, with limited permeation of the blood-brain barrier, and is likely a peripheral mechanism of action. The results are further illustrated in FIG. 5.

Example 13

Figure 6:
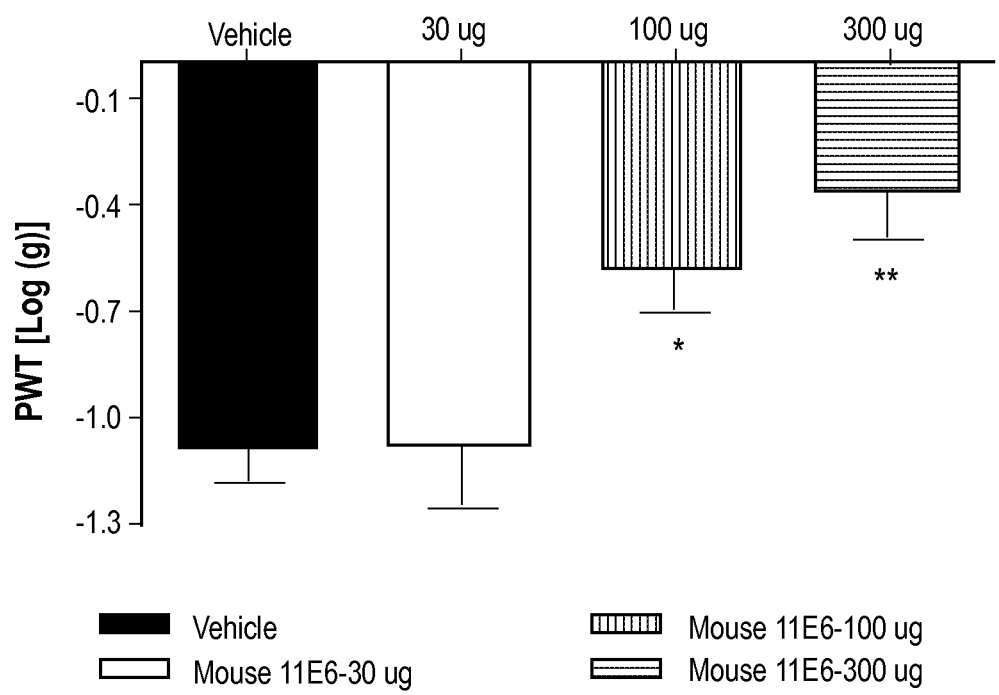
FIG. 6 shows the effects of RAGE antibody in a mouse model of inflammatory pain as described in Example 13. Specifically, as shown in this figure, RAGE mAB ML39-11E6 was dosed at 30, 100 and 300 μg per mouse (C57BL/6), ip; IgG-1 (KLH mAB H35C206) at 100 μg per mouse (C57BL/6), intraperitoneal (ip). Animals were dosed on day 1 post CFA and tested 60 minutes post dose. *p<0.05; **p<0.01 versus vehicle (n=10 per group).

Duration of Anti-Nociceptive Efficacy was Measured Following a Single Dose (30, 100 or 300 μg/Mouse) of Mouse 11E6 in Inflammatory and Neuropathic Pain Models Mice (C57BL/6—available from Charles River Laboratories, Inc., Wilmington, Mass. 250-300 g, N=10 per group) were injected with complete Freund's adjuvant (CFA) and inflammation developed over 24 hours. At 24 hours post-CFA, a single dose of mouse 11E6 (also known as ML39-11E6) (30, 100 or 300 μg/mouse), or negative control IgG (KLH mAB H35C206-100 μg/mouse was injected. Paw withdrawal threshold was measured using von Frey monofilaments (available from Stoetling Co., Wood Dale, Ill.) sixty minutes, post injection. Dose-dependent analgesic efficacy of mouse 11E6 was observed in the CFA model of inflammatory pain following acute dosing (sixty minutes). The results are shown in FIG. 6. The results in FIG. 6 show an effect on acute neurotransmission.

Example 14

Figure 7:
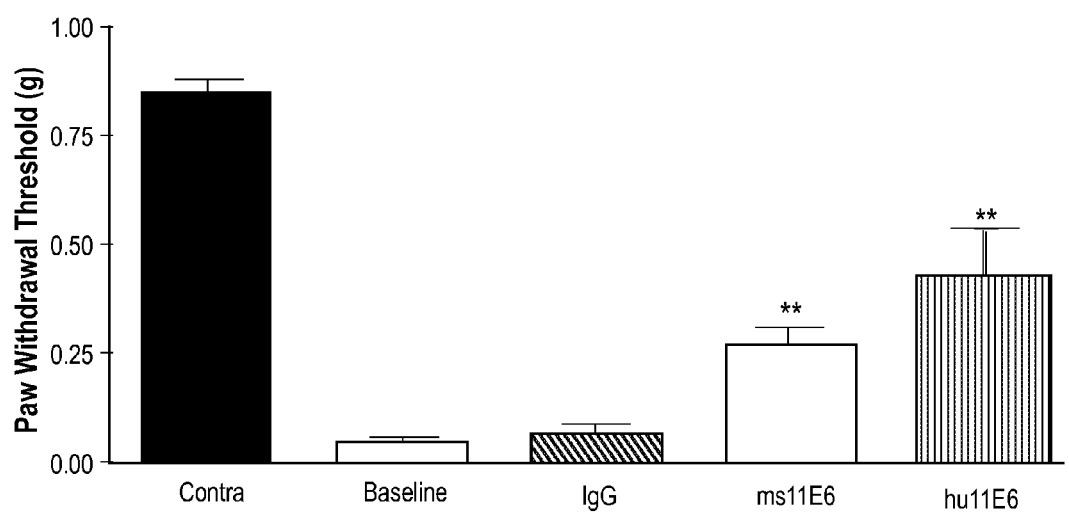
FIG. 7 shows the time course effects of human and mouse anti-RAGE antibodies in a mouse model of neuropathic pain as described in Example 14. Specifically, chronic constriction injury (Bennett model) surgeries were performed 7 days before this experiment was conducted. RAGE mAB 11E6 (which is also referred to herein as ms11E6, 11E6.50, A-992401.0 and ML39-11E6), hu11E6 (also referred to herein as 11E6.12hu and A-1175708.0) and human IgG were dosed at 300 ug in 200 μl/mouse once per mouse (C57BL/6), ip and tested 24 hours, following treatment. **p<0.01, versus vehicle, unpaired t-test (n=5; 24 hours). In this FIG. 7, CONTRA refers to contralateral paw tested.

Duration of Anti-Nociceptive Efficacy was Measured Following a Single Dose (300 μg/Mouse) of Mouse and Human 11E6, Anti-RAGE Antibodies, in the Chronic Constriction Injury Model Neuropathic Pain Chronic constriction injury (CCI) model of neuropathic pain was performed in mice (C57BL/6-250-300 g, N=5) and developed over 7 days. On the seventh day, mouse 11E6.50 (also known as ms11E6, A-992401.0 and 11E6.50) (300 μg/mouse), human mouse 11E6 (also known as hu11E6; A-1175708.0 and 11E6.12hu), (300 μg/mouse), or negative control IgG was injected. Paw withdrawal threshold was measured using von Frey monofilaments at 24 hours post injection. Analgesic efficacy of mouse (ms11E6) and human 11E6 (hu11E6) was observed in the CCI model of neuropathic pain at 24 hours following a single dose treatment). The results are shown in FIG. 7.

Documents as cited herein are incorporated by reference.

What is claimed is:

1. A method for treating pain, comprising the step of administering to a mammal in need thereof an effective amount of a composition comprising an isolated monoclonal antibody or antigen binding fragment thereof, wherein said said antibody or antigen binding fragment thereof binds an epitope of a human Receptor Advanced Glycation End products (RAGE) molecule, said antibody or antigen binding fragment thereof comprising an antigen binding domain comprising:
  a) a heavy chain variable domain comprising complementarity determining regions (CDR) 1, 2 and 3 wherein the CDR 1, CDR 2, CDR 3 comprise the sequences of SEQ ID NO: 10, SEQ ID NO: 11 and SEQ ID NO: 12, respectively; and
  b) a light chain variable domain comprising complementarity determining regions (CDR) 1, 2 and 3 wherein the CDR 1, CDR 2, CDR 3 comprise the sequences of SEQ ID NO: 14, SEQ ID NO: 15, and SEQ ID NO: 16, respectively.

2. The method according to claim 1, wherein the antibody further comprises a human acceptor framework.

3. The method of claim 1, wherein the antibody comprises at a heavy chain variable domain comprising the sequence of: SEQ ID NOs: 9, and a light chain variable domain comprising the sequence of: SEQ ID NOs: 13.

4. The method of claim 1, wherein the antibody comprises
  (a) at least one framework mutation in the framework region of the heavy chain variable domain wherein the sequence of the heavy chain variable domain comprises an amino acid sequence selected from the group consisting of: 62, 67, 68 and 69; and
  (b) at least one framework mutation in the framework region of the light chain variable domain wherein the sequence of the heavy chain variable domain comprises an amino acid sequence selected from the group consisting of: 63, 64, 65 and 66; or (c) combinations of (a) and (b).

5. The method of claim 1, wherein the composition comprises a formulation, wherein said formulation comprises the antibody of claim 1 in crystallized form as an ingredient; and at least one polymeric carrier.

6. The method of claim 1, wherein said pain is selected from the group consisting of chronic and acute pain.

7. The method of claim 1, wherein said pain is selected from the group consisting of:
  peripheral or central neuropathic pain, nociceptive pain; and psychogenic pain.

8. The method of claim 1, wherein said pain is nociceptive pain or psychogenic pain.

9. The method of claim 1, wherein said pain is neuropathic pain.

10. The method of claim 9, wherein said neuropathic pain is peripheral or central neuropathic pain.

11. The method of claim 1, wherein said pain is inflammatory pain.

12. A method for treating pain, comprising the step of administering to a mammal in need thereof an effective amount of a composition comprising an isolated monoclonal antibody or antigen binding fragment thereof, wherein said antibody or antigen binding fragment thereof specifically binds to the C2 domain of human Receptor Advanced Glycation End Products (RAGE) protein having the amino acid sequence of SEQ ID NO:60 and wherein said antibody does not bind an epitope of the V domain or the C1 domain of human RAGE; wherein said antibody
- a) is a neutralizing antibody that is able to neutralize in vivo the effect of Aβ1-40 on cerebral vasculature of mice;
- b) does not bind to an epitope selected from the group consisting of SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79 and SEQ ID NO:80; and
- c) binds a C2 epitope selected from the group consisting of amino acid residues 238-314, 229-340, 229-331 and 229-330 of the human RAGE protein having the amino acid sequence of SEQ ID NO:60.

* * * * *

UNITED STATES PATENT AND TRADEMARK OFFICE
CERTIFICATE OF CORRECTION

PATENT NO. : 8,420,083 B2  
APPLICATION NO. : 12/914426  
DATED : April 16, 2013  
INVENTOR(S) : Strakhova et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 113 days.

Signed and Sealed this  
Sixteenth Day of December, 2014

Michelle K. Lee  
*Deputy Director of the United States Patent and Trademark Office*

SEQUENCE LISTING

```
<160> NUMBER OF SEQ ID NOS: 97

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Glu Lys Leu Glu Glu Ser Gly Gly Gly Leu Val Gln Leu Gly Gly
1               5                   10                  15

Ser Met Lys Ile Ser Cys Val Ala Ser Gly Phe Thr Leu Ser Asn Tyr
            20                  25                  30

Trp Met Asp Trp Val Arg Gln Ser Pro Glu Lys Gly Leu Glu Trp Ile
        35                  40                  45

Ala Glu Ile Arg Leu Lys Ser Asn Tyr Tyr Ser Thr His Tyr Ala Glu
    50                  55                  60

Ser Val Lys Gly Arg Phe Ser Ile Ser Arg Asp Asp Ser Lys Gly Ser
65                  70                  75                  80

Val Ser Leu Gln Met Asp Asn Leu Thr Ala Glu Asp Thr Gly Ile Tyr
                85                  90                  95

Phe Cys Ala Arg Asn Ala Tyr Trp Tyr Phe Asp Val Trp Gly Thr Gly
            100                 105                 110
```

```
Thr Thr Val Thr Val Ser Ser
        115

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Tyr Trp Met Asp
1               5

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Ile Arg Leu Lys Ser Asn Tyr Tyr Ser Thr His Tyr Ala Glu Ser
1               5                   10                  15

Val Lys Gly

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Ala Tyr Trp Tyr Phe Asp Val
1               5

<210> SEQ ID NO 5
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Val Met Thr Gln Ser His Lys Phe Met Ser Thr Ser Val Gly
1               5                   10                  15

Asp Arg Val Ser Ala Thr Cys Lys Ala Ser Gln Asp Val Gly Thr Ser
            20                  25                  30

Val Ala Trp Tyr Gln Gln Lys Leu Gly Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Asn Tyr Pro Leu
                85                  90                  95

Thr Phe Gly Asp Gly Thr Lys Leu Glu Leu Lys Arg
            100                 105
```

```
<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Ala Ser Gln Asp Val Gly Thr Ser Val Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Thr Ser Thr Arg His Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Tyr Asn Asn Tyr Pro Leu Thr
1               5

<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Ala Pro Gly Lys Gly Leu Lys Trp Met
        35                  40                  45

Gly Tyr Ile Asn Thr Asn Thr Gly Glu Ser Ile Tyr Ser Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Ser Arg Met Val Thr Ala Tyr Gly Met Asp Tyr Trp Gly Gln
            100                 105                 110

Gly Thr Ser Val Thr Val Ser Ser
        115                 120

<210> SEQ ID NO 10
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 10

Asn Phe Gly Met Asn
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ile Asn Thr Asn Thr Gly Glu Ser Ile Tyr Ser Glu Glu Phe Lys
1               5                   10                  15

Gly

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Arg Met Val Thr Ala Tyr Gly Met Asp Tyr
1               5                   10

<210> SEQ ID NO 13
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
                20                  25                  30

Val Ala Trp Tyr Gln Gln Arg Pro Gly Gln Ser Pro Lys Leu Leu Ile
            35                  40                  45

Phe Ser Ala Ser Asn Arg Tyr Thr Gly Val Pro Asp Arg Phe Thr Gly
        50                  55                  60

Ser Gly Ser Gly Thr Asp Phe Thr Leu Thr Leu Ser Asn Met Gln Pro
65                  70                  75                  80

Glu Asp Leu Ala Asp Tyr Phe Cys Gln Gln Tyr Ser Ser Tyr Pro Leu
                85                  90                  95

Thr Phe Gly Val Gly Thr Lys Leu Glu Leu Lys Arg
            100                 105

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Lys Ala Ser Gln Asn Val Gly Thr Ala Val Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Ala Ser Asn Arg Tyr Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Tyr Ser Ser Tyr Pro Leu Thr
1               5

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Asn Asn Tyr
            20                  25                  30

Leu Ile Glu Trp Ile Lys Gln Arg Pro Gly Gln Gly Leu Glu Trp Ile
        35                  40                  45

Gly Val Ile Asn Pro Gly Ser Gly Gly Thr Asn His Asn Glu Lys Phe
    50                  55                  60

Lys Val Lys Ala Thr Leu Thr Ala Asp Lys Ser Ser Thr Ala Tyr
65                  70                  75                  80

Ile Gln Leu Ser Ser Leu Thr Ser Asp Asp Ser Ala Val Tyr Phe Cys
                85                  90                  95

Ala Arg Ser Ala Gly Thr Ala Arg Ala Arg Phe Ala Tyr Trp Gly Gln
            100                 105                 110

Gly Thr Leu Val Thr Val Ser Ala
        115                 120

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Asn Tyr Leu Ile Glu
1               5
```

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Val Ile Asn Pro Gly Ser Gly Gly Thr Asn His Asn Glu Lys Phe Lys
1               5                   10                  15

Val
```

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Ser Ala Gly Thr Ala Arg Ala Arg Phe Ala Tyr
1               5                   10
```

<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Phe Pro Phe
                85                  90                  95

Thr Phe Gly Ser Gly Thr Lys Leu Glu Ile Lys Arg
            100                 105
```

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Arg Ala Ser Gln Asp Ile Gly Ser Ser Leu Asn
1               5                   10
```

```
<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Thr Ser Ser Leu Asp Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Gln Tyr Ala Ser Phe Pro Phe Thr
1               5

<210> SEQ ID NO 25
<211> LENGTH: 330
<212> TYPE: PRT
<213> ORGANISM: Homo sapiens

<400> SEQUENCE: 25

Ala Ser Thr Lys Gly Pro Ser Val Phe Phe Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 106
<212> TYPE: PRT
<213> ORGANISM: Homo sapiens

<400> SEQUENCE: 26

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 27
<211> LENGTH: 6276
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta agggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaattat    600 tcatatcagg attatcaata ccatattttt gaaaagccg tttctgtaat gaaggagaaa    660
```

```
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
```

```
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacgcgggga tataacatga gctgtcttcg gtatcgtcgt    3780
atcccactac cgagatgtcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccacttt tcccgcgttt    4500 tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg tgtccggga    4680 tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatcga tctcgatccc    4980
gcgaaattaa tacgactcac tatagggaa ttgtgagcgg ataacaattc ccctctagaa    5040
ataattttgt ttaactttaa gaaggagata tacatatgaa aaagacagct atcgcgattg    5100
cagtggcact ggctggtttc gctaccgtag cgcaggccgc tcaaaacatc acagcccgga    5160
ttggcgagcc actggtgctg aagtgtaagg gggcccccaa gaaaccaccc cagcggctgg    5220
aatgaaaact gaacacaggc cggacagaag cttggaaggt cctgtctccc cagggaggag    5280
gcccctggga cagtgtggct cgtgtccttc ccaacggctc cctcttcctt ccggctgtcg    5340
ggatccagga tgaggggatt ttccggtgcc aggcaatgaa caggaatgga aaggagacca    5400
agtccaacta ccgagtccgt gtctaccaga ttcctgggaa gccagaaatt gtagattctg    5460
```

```
cctctgaact cacggctggt gttcccaata aggtggggac atgtgtgtca gagggaagct    5520
accctgcagg gactcttagc tggcacttgg atgggaagcc cctggtgcct aatgagaagg    5580
gagtatctgt gaaggaacag accaggagac accctgagac agggctcttc acactgcagt    5640
cggagctaat ggtgacccca gcccgggag gagatccccg tcccaccttc tcctgtagct     5700
tcagcccagg ccttccccga caccgggcct tgcgcacagc cccatccag cccgtgtct      5760 gggagcctgt gcctctggag gaggtccaat tggtggtgga gccagaaggt ggagcagtag    5820
ctcctggtgg aaccgtaacc ctgacctgtg aagtccctgc ccagccctct cctcaaatcc    5880
actggatgaa ggatggtgtg cccttgcccc ttcccccag ccctgtgctg atcctccctg     5940
agatagggcc tcaggaccag ggaacctaca gctgtgtggc cacccattcc agccacgggc    6000
cccaggaaag ccgtgctgtc agcatcagca tcatcgaacc aggcgaggag gggccaactg    6060
caggctctgt gggaggatca gggctgggaa ctcaccacca ccaccaccac tgactcgagc    6120
accaccacca ccaccactga gatccggctg ctaacaaagc ccgaaaggaa gctgagttgg    6180
ctgctgccac cgctgagcaa taactagcat aaccccttgg ggcctctaaa cgggtcttga    6240 ggggttttttt gctgaaagga ggaactatat ccggat                              6276

<210> SEQ ID NO 28
<211> LENGTH: 5617
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tcccctttagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgattc ggcctattgg ttaaaaatg agctgattta         420 acaaaaatt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat    1020
tttcacctga tcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
```

```
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttcc gaaggtaac tggcttcagc    1620 agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccggttg gactcaagac gatagttacc ggataaggcg      1800
cagcggtcgg gctgaacggg gggttcgtgc acacagccca gcttggagcg aacgacctac   1860
accgaactga atacctaca gcgtgagcta tgagaaagcg ccacgcttcc cgaagggaga     1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc ccgcgcccca   3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
```

```
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgggcagca gccatcatca tcatcatcac    5100
agcagcggcc tggtgccgcg cggcagccat atgcaaaaca tcacagcccg gattggcgag    5160
ccactggtgc tgaagtgtaa ggggccccc aagaaaccac cccagcggct ggaatggaaa    5220
ctgaacacag gccggacaga agcttggaag gtcctgtctc cccagggagg aggcccctgg    5280
gacagtgtgg ctcgtgtcct tcccaacggc tccctcttcc ttccggctgt cgggatccag    5340
gatgagggga ttttccggtg ccaggcaatg aacaggaatg gaaaggagac caagtccaac    5400
taccgagtcc gtgtctacca gattcctggg aagccagaaa ttgtagattc ttgactcgag    5460
caccaccacc accaccactg agatccggct gctaacaaag cccgaaagga agctgagttg    5520
gctgctgcca ccgctgagca ataactagca taaccccttg ggcctctaa acgggtcttg    5580 aggggttttt tgctgaaagg aggaactata tccggat                             5617
```

<210> SEQ ID NO 29
<211> LENGTH: 5932
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
tggcgaatgg gacgcgccct gtagcggcgc attaagcgcg gcgggtgtgg tggttacgcg      60
```

-continued

```
cagcgtgacc gctacacttg ccagcgccct agcgcccgct cctttcgctt tcttcccttc    120 cttttctcgcc acgttcgccg gctttccccg tcaagctcta aatcggggc tccctttagg    180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta tagggattt tgccgatttc ggcctattgg ttaaaaatg agctgattta      420 acaaaattt aacgcgaatt ttaacaaaat attaacgttt acaatttcag gtggcacttt     480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500 gatcctttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280 tatttttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
```

```
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccgaaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
```

```
cgagcccgat cttccccatc ggtgatgtcg gcgatatagg cgccagcaac cgcacctgtg   4920
gcgccggtga tgccgccac gatgcgtccg gcgtagagga tcgagatctc gatcccgcga    4980
aattaatacg actcactata ggggaattgt gagcggataa caattcccct ctagaaataa   5040
ttttgtttaa ctttaagaag gagatatacc atgggcagca gccatcatca tcatcatcac   5100
agcagcggcc tggtgccgcg cggcagccat atgcaaaaca tcacagcccg gattggcgag   5160
ccactggtgc tgaagtgtaa gggggccccc aagaaaccac cccagcggct ggaatggaaa   5220
ctgaacacag gccggacaga agcttggaag gtcctgtctc cccagggagg aggcccctgg   5280
gacagtgtgg ctcgtgtcct tcccaacggc tccctcttcc ttccggctgt cgggatccag   5340
gatgagggga ttttccggtg ccaggcaatg aacaggaatg aaaggagac caagtccaac    5400 taccgagtcc gtgtctacca gattcctggg aagccagaaa ttgtagattc tgcctctgaa   5460
ctcacggctg gtgttcccaa taaggtgggg acatgtgtgt cagagggaag ctaccctgca   5520
gggactctta gctggcactt ggatgggaag ccccctggtgc ctaatgagaa gggagtatct  5580
gtgaaggaac agaccaggag acaccctgag acagggctct tcacactgca gtcggagcta   5640
atggtgaccc cagcccgggg aggagatccc cgtcccacct tctcctgtag cttcagccca   5700
ggccttcccc gacaccgggc cttgcgcaca gccccatcc agcccgtgt ctgggagcct     5760 gtgccttgac tcgagcacca ccaccaccac cactgagatc cggctgctaa caaagcccga   5820
aaggaagctg agttggctgc tgccaccgct gagcaataac tagcataacc ccttggggcc   5880
tctaaacggg tcttgagggg ttttttgctg aaaggaggaa ctatatccgg at           5932
```

<210> SEQ ID NO 30
<211> LENGTH: 6238
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcggggc tcccttagg     180 gttccgattt agtgctttac ggcacctcga cccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta agggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa ccccatttg tttattttc taaatacatt caaatatgta    540
tccgctcatg aattaattct tagaaaaact catcgagcat caaatgaaac tgcaattat     600 tcatatcagg attatcaata ccatatttt gaaaaagccg tttctgtaat gaaggagaaa    660
actcaccgag gcagttccat aggatggcaa gatcctggta tcggtctgcg attccgactc   720
gtccaacatc aatacaacct attaatttcc cctcgtcaaa aataaggtta tcaagtgaga   780
aatcaccatg agtgacgact gaatccggtg agaatggcaa aagtttatgc atttctttcc   840
agacttgttc aacaggccag ccattacgct cgtcatcaaa atcactcgca tcaaccaaac   900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat   1020
```

```
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg caacgctac     1200 cttttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc  cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagactta    3000 cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
```

```
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgcggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgggcagca gccatcatca tcatcatcac   5100
agcagcggcc tggtgccgcg cggcagccat atgcaaaaca tcacagcccg gattggcgag   5160
ccactggtgc tgaagtgtaa gggggccccc aagaaccac cccagcggct ggaatgaaa   5220
ctgaacacag gccggacaga agcttggaag gtcctgtctc cccagggagg aggcccctgg   5280
gacagtgtgg ctcgtgtcct tcccaacggc tccctcttcc ttccggctgt cgggatccag   5340
gatgagggga ttttccggtg ccaggcaatg aacaggaatg gaaaggagac caagtccaac   5400
taccgagtcc gtgtctacca gattcctggg aagccagaaa ttgtagattc tgcctctgaa   5460
ctcacggctg gtgttcccaa taaggtgggg acatgtgtgt cagagggaag ctaccctgca   5520
gggactctta gctggcactt ggatgggaag cccctggtgc taatgagaa gggagtatct   5580
gtgaaggaac agaccaggag acaccctgag acagggctct tcacactgca gtcggagcta   5640
atggtgaccc cagccggggg aggagatccc cgtcccacct tctcctgtag cttcagccca   5700
ggccttcccc gacaccgggc cttgcgcaca gcccccatcc agcccgtgt ctgggagcct   5760
gtgcctctgg aggaggtcca attggtggtg gagccagaag gtggagcagt agctcctggt   5820
```

```
ggaaccgtaa ccctgacctg tgaagtccct gcccagccct ctcctcaaat ccactggatg      5880
aaggatggtg tgcccttgcc ccttcccccc agccctgtgc tgatcctccc tgagataggg      5940
cctcaggacc agggaaccta cagctgtgtg gccacccatt ccagccacgg gccccaggaa      6000
agccgtgctg tcagcatcag catcatcgaa ccaggcgagg aggggccaac tgcaggctct      6060
gtgggaggat catgactcga gcaccaccac caccaccact gagatccggc tgctaacaaa      6120
gcccgaaagg aagctgagtt ggctgctgcc accgctgagc aataactagc ataacccctt      6180
ggggcctcta acgggtctt gagggttttt ttgctgaaag gaggaactat atccggat        6238
```

<210> SEQ ID NO 31
<211> LENGTH: 5614
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
tggcgaatgg gacgcgccct gtagcggcgc attaagcgcg gcgggtgtgg tggttacgcg        60
cagcgtgacc gctacacttg ccagcgccct agcgcccgct cctttcgctt tcttcccttc       120
ctttctcgcc acgttcgccg gctttccccg tcaagctcta atcggggc tccctttagg        180 gttccgattt agtgctttac ggcacctcga ccccaaaaaa cttgattagg gtgatggttc       240
acgtagtggg ccatcgccct gatagacggt ttttcgccct ttgacgttgg agtccacgtt       300
ctttaatagt ggactcttgt tccaaactgg aacaacactc aaccctatct cggtctattc       360
ttttgattta aagggatttt gccgatttc ggcctattgg ttaaaaaatg agctgattta        420
acaaaaattt aacgcgaatt ttaacaaaat attaacgttt acaatttcag gtggcacttt       480
tcggggaaat gtgcgcggaa ccccatttg tttattttc taaatacatt caaatatgta        540
tccgctcatg aattaattct tagaaaaact catcgagcat caaatgaaac tgcaatttat       600
tcatatcagg attatcaata ccatatttt gaaaaagccg tttctgtaat gaaggagaaa       660
actcaccgag gcagttccat aggatggcaa gatcctggta tcggtctgcg attccgactc       720
gtccaacatc aatacaacct attaatttcc cctcgtcaaa aataaggtta tcaagtgaga      780
aatcaccatg agtgacgact gaatccggtg agaatggcaa aagtttatgc atttctttcc      840
agacttgttc aacaggccag ccattacgct cgtcatcaaa atcactcgca tcaaccaaac       900
cgttattcat tcgtgattgc gcctgagcga gacgaaatac gcgatcgctg ttaaaaggac       960
aattacaaac aggaatcgaa tgcaaccggc gcaggaacac tgccagcgca tcaacaatat      1020
tttcacctga atcaggatat tcttctaata cctggaatgc tgttttcccg gggatcgcag      1080
tggtgagtaa ccatgcatca tcaggagtac ggataaaatg cttgatggtc ggaagaggca      1140
taaattccgt cagccagttt agtctgacca tctcatctgt aacatcattg gcaacgctac      1200
ctttgccatg tttcagaaac aactctggcg catcgggctt cccatacaat cgatagattg      1260
tcgcacctga ttgcccgaca ttatcgcgag cccatttata cccatataaa tcagcatcca      1320
tgttggaatt taatcgcggc ctagagcaag acgtttcccg ttgaatatgg ctcataacac      1380
cccttgtatt actgtttatg taagcagaca gttttattgt tcatgaccaa atcccttaa       1440 cgtgagtttt cgttccactg agcgtcagac cccgtagaaa agatcaaagg atcttcttga      1500
gatccttttt ttctgcgcgt aatctgctgc ttgcaaacaa aaaaaccacc gctaccagcg      1560
gtggtttgtt tgccggatca agagctacca actctttttc cgaaggtaac tggcttcagc      1620
```

```
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100 gccttttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg cgcgcattg   3840 cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
```

| | |
|---|---|
| agacagaact taatgggccc gctaacagcg cgatttgctg gtgacccaat gcgaccagat | 4080 |
| gctccacgcc cagtcgcgta ccgtcttcat gggagaaaat aatactgttg atgggtgtct | 4140 |
| ggtcagagac atcaagaaat aacgccggaa cattagtgca ggcagcttcc acagcaatgg | 4200 |
| catcctggtc atccagcgga tagttaatga tcagcccact gacgcgttgc gcgagaagat | 4260 |
| tgtgcaccgc cgctttacag gcttcgacgc cgcttcgttc taccatcgac accaccacgc | 4320 |
| tggcacccag ttgatcggcg cgagatttaa tcgccgcgac aatttgcgac ggcgcgtgca | 4380 |
| gggccagact ggaggtggca acgccaatca gcaacgactg tttgcccgcc agttgttgtg | 4440 |
| ccacgcggtt gggaatgtaa ttcagctccg ccatcgccgc ttccactttt tcccgcgttt | 4500 |
| tcgcagaaac gtggctggcc tggttcacca cgcgggaaac ggtctgataa gagacaccgg | 4560 |
| catactctgc gacatcgtat aacgttactg gtttcacatt caccaccctg aattgactct | 4620 |
| cttccgggcg ctatcatgcc ataccgcgaa aggttttgcg ccattcgatg gtgtccggga | 4680 |
| tctcgacgct ctcccttatg cgactcctgc attaggaagc agcccagtag taggttgagg | 4740 |
| ccgttgagca ccgccgccgc aaggaatggt gcatgcaagg agatggcgcc caacagtccc | 4800 |
| ccggccacgg ggcctgccac catacccacg ccgaaacaag cgctcatgag cccgaagtgg | 4860 |
| cgagcccgat cttccccatc ggtgatgtcg gcgatatagg cgccagcaac cgcacctgtg | 4920 |
| gcgccggtga tgccggccac gatgcgtccg gcgtagagga tcgagatctc gatcccgcga | 4980 |
| aattaatacg actcactata ggggaattgt gagcggataa caattcccct ctagaaataa | 5040 |
| ttttgtttaa ctttaagaag gagatatacc atgggcagca gccatcatca tcatcatcac | 5100 |
| agcagcggcc tggtgccgcg cggcagccat atggcctctg aactcacggc tggtgttccc | 5160 |
| aataaggtgg ggacatgtgt gtcagaggga agctaccctg cagggactct tagctggcac | 5220 |
| ttggatggga agcccctggt gcctaatgag aagggagtat ctgtgaagga acagaccagg | 5280 |
| agacacctg agacagggct cttcacactg cagtcggagc taatggtgac ccagcccgg | 5340 |
| ggaggagatc cccgtcccac cttctcctgt agcttcagcc caggccttcc ccgacaccgg | 5400 |
| gccttgcgca cagcccccat ccagcccgt gtctgggagc ctgtgccttg actcgagcac | 5460 |
| caccaccacc accactgaga tccggctgct aacaaagccc gaaaggaagc tgagttggct | 5520 |
| gctgccaccg ctgagcaata actagcataa ccccttgggg cctctaaacg ggtcttgagg | 5580 |
| ggttttttgc tgaaaggagg aactatatcc ggat | 5614 |

<210> SEQ ID NO 32
<211> LENGTH: 5920
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 32

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta taagggattt tgccgatttc ggcctattgg ttaaaaaatg agctgattta | 420 |
| acaaaaattt aacgcgaatt ttaacaaaat attaacgttt acaatttcag gtggcacttt | 480 |

```
tcggggaaat gtgcgcggaa cccctatttg tttattttc taaatacatt caaatatgta       540
tccgctcatg aattaattct tagaaaaact catcgagcat caaatgaaac tgcaatttat       600
tcatatcagg attatcaata ccatattttt gaaaaagccg tttctgtaat gaaggagaaa       660
actcaccgag gcagttccat aggatggcaa gatcctggta tcggtctgcg attccgactc       720
gtccaacatc aatacaacct attaatttcc cctcgtcaaa ataaggttta tcaagtgaga       780
aatcaccatg agtgacgact gaatccggtg agaatggcaa aagtttatgc atttctttcc       840
agacttgttc aacaggccag ccattacgct cgtcatcaaa atcactcgca tcaaccaaac       900
cgttattcat tcgtgattgc gcctgagcga gacgaaatac gcgatcgctg ttaaaaggac       960
aattacaaac aggaatcgaa tgcaaccggc gcaggaacac tgccagcgca tcaacaatat      1020
tttcacctga atcaggatat tcttctaata cctggaatgc tgttttcccg gggatcgcag      1080
tggtgagtaa ccatgcatca tcaggagtac ggataaaatg cttgatggtc ggaagaggca      1140
taaattccgt cagccagttt agtctgacca tctcatctgt aacatcattg gcaacgctac      1200
ctttgccatg tttcagaaac aactctggcg catcgggctt cccatacaat cgatagattg      1260
tcgcacctga ttgcccgaca ttatcgcgag cccatttata cccatataaa tcagcatcca      1320
tgttggaatt taatcgcggc ctagagcaag acgtttcccg ttgaatatgg ctcataacac      1380
cccttgtatt actgtttatg taagcagaca gtttattgt tcatgaccaa aatcccttaa       1440
cgtgagtttt cgttccactg agcgtcagac cccgtagaaa agatcaaagg atcttcttga      1500
gatccttttt ttctgcgcgt aatctgctgc ttgcaaacaa aaaaaccacc gctaccagcg      1560
gtggtttgtt tgccggatca agagctacca actctttttc cgaaggtaac tggcttcagc      1620
agagcgcaga taccaaatac tgtccttcta gtgtagccgt agttaggcca ccacttcaag      1680
aactctgtag caccgcctac atacctcgct ctgctaatcc tgttaccagt ggctgctgcc      1740
agtggcgata gtcgtgtct taccggggttg gactcaagac gatagttacc ggataaggcg      1800
cagcggtcgg gctgaacggg gggttcgtgc acacagccca gcttggagcg aacgacctac      1860
accgaactga gatacctaca gcgtgagcta tgagaaagcg ccacgcttcc cgaagggaga      1920
aaggcggaca ggtatccggt aagcggcagg gtcggaacag gagagcgcac gagggagctt      1980
ccaggggaaa acgcctggta tctttatagt cctgtcgggt ttcgccacct ctgacttgag      2040
cgtcgatttt tgtgatgctc gtcagggggg cggagcctat ggaaaaacgc cagcaacgcg      2100
gcctttttac ggttcctggc cttttgctgg ccttttgctc acatgttctt tcctgcgtta      2160
tcccctgatt ctgtggataa ccgtattacc gcctttgagt gagctgatac cgctcgccgc      2220
agccgaacga ccgagcgcag cgagtcagtg agcgaggaag cggaagagcg cctgatgcgg      2280
tattttctcc ttacgcatct gtgcggtatt tcacaccgca tatatggtgc actctcagta      2340
caatctgctc tgatgccgca tagttaagcc agtatacact ccgctatcgc tacgtgactg      2400
ggtcatggct gcgccccgac acccgccaac acccgctgac gcgccctgac gggcttgtct      2460
gctcccggca tccgcttaca gacaagctgt gaccgtctcc gggagctgca tgtgtcagag      2520
gttttcaccg tcatcaccga aacgcgcgag gcagctgcgg taaagctcat cagcgtggtc      2580
gtgaagcgat tcacagatgt ctgcctgttc atccgcgtcc agctcgttga gtttctccag      2640
aagcgttaat gtctggcttc tgataaagcg ggccatgtta agggcggttt tttcctgttt      2700
ggtcactgat gcctccgtgt aagggggatt tctgttcatg ggggtaatga taccgatgaa      2760
acgagagagg atgctcacga tacgggttac tgatgatgaa catgcccggt tactggaacg      2820
ttgtgagggt aaacaactgg cggtatggat gcggcgggac cagagaaaaa tcactcaggg      2880
```

```
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag gtggtttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccgaaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgggcagca gccatcatca tcatcatcac   5100
agcagcggcc tggtgccgcg cggcagccat atggcctctg aactcacggc tggtgttccc   5160
aataaggtgg ggacatgtgt gtcagaggga agctaccctg cagggactct tagctggcac   5220
ttggatggga agcccctggt gcctaatgag aagggagtat ctgtgaagga acagaccagg   5280
```

| | |
|---|---|
| agacaccctg agacagggct cttcacactg cagtcggagc taatggtgac cccagcccgg | 5340 |
| ggaggagatc cccgtcccac cttctcctgt agcttcagcc caggccttcc ccgacaccgg | 5400 |
| gccttgcgca cagcccccat ccagcccgt gtctgggagc ctgtgcctct ggaggaggtc | 5460 |
| caattggtgg tggagccaga aggtggagca gtagctcctg gtggaaccgt aaccctgacc | 5520 |
| tgtgaagtcc ctgcccagcc ctctcctcaa atccactgga tgaaggatgg tgtgcccttg | 5580 |
| cccctttccc ccagccctgt gctgatcctc cctgagatag ggcctcagga ccagggaacc | 5640 |
| tacagctgtg tggccaccca ttccagccac gggcccagg aaagccgtgc tgtcagcatc | 5700 |
| agcatcatcg aaccaggcga ggagggggcca actgcaggct ctgtgggagg atcatgactc | 5760 |
| gagcaccacc accaccacca ctgagatccg gctgctaaca aagcccgaaa ggaagctgag | 5820 |
| ttggctgctg ccaccgctga gcaataacta gcataacccc ttggggcctc taaacgggtc | 5880 |
| ttgaggggtt ttttgctgaa aggaggaact atatccggat | 5920 |

```
<210> SEQ ID NO 33
<211> LENGTH: 5605
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
```

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcggggc tcccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta aagggatttt tgccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg aattaattct tagaaaaact catcgagcat caaatgaaac tgcaatttat | 600 |
| tcatatcagg attatcaata ccatatttt gaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga cgaaatac gcgatcgctg ttaaaaggac | 960 |
| aattacaaac aggaatcgaa tgcaaccggc gcaggaacac tgccagcgca tcaacaatat | 1020 |
| tttcacctga tcaggatat tcttctaata cctggaatgc tgtttttccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |
| tgttggaatt taatcgcggc ctagagcaag acgtttcccg ttgaatatgg ctcataacac | 1380 |

```
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatcctttt  ttctgcgcgt aatctgctgc ttgcaaacaa aaaaaccacc gctaccagcg   1560
gtggtttgtt tgccggatca agagctacca actcttttc  cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccaggggaa  acgcctggta tctttatagt cctgtcgggt ttcgccacct ctgacttgag   2040
cgtcgatttt tgtgatgctc gtcaggggg  cggagcctat ggaaaaacgc cagcaacgcg   2100
gcctttttac ggttcctggc cttttgctgg cctttgctc  acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac accgctgac  gcgccctgac gggcttgtct   2460
gctcccggca tccgcttaca gacaagctgt gaccgtctcc gggagctgca tgtgtcagag   2520
gttttcaccg tcatccgga  aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag tcgcagacg  ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
```

```
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccgacgcg agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa agacaccgg    4560 catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc aacagtccc    4800 ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgggcagca gccatcatca tcatcatcac   5100
agcagcggcc tggtgccgcg cggcagccat atgctggagg aggtccaatt ggtggtggag   5160
ccagaaggtg gagcagtagc tcctggtgga accgtaaccc tgacctgtga agtccctgcc   5220
cagccctctc ctcaaatcca ctggatgaag gatggtgtgc ccttgcccct tcccccagc    5280 cctgtgctga tcctccctga gatagggcct caggaccagg gaacctacag ctgtgtggcc   5340
acccattcca gccacgggcc ccaggaaagc cgtgctgtca gcatcagcat catcgaacca   5400
ggcgaggagg ggccaactgc aggctctgtg ggaggatcat gactcgagca ccaccaccac   5460
caccactgag atccggctgc taacaaagcc cgaaaggaag ctgagttggc tgctgccacc   5520
gctgagcaat aactagcata accccttggg gcctctaaac gggtcttgag ggttttttg    5580 ctgaaaggag gaactatatc cggat                                        5605
```

<210> SEQ ID NO 34
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Lys Lys Thr Ala Ile Ala Ile Ala Val Ala Leu Ala Gly Phe Ala
1               5                   10                  15

Thr Val Ala Gln Ala Ala Gln Asn Ile Thr Ala Arg Ile Gly Glu Pro
            20                  25                  30

Leu Val Leu Lys Cys Lys Gly Ala Pro Lys Lys Pro Pro Gln Arg Leu

```
                35                  40                  45
Glu Trp Lys Leu Asn Thr Gly Arg Thr Glu Ala Trp Lys Val Leu Ser
 50                  55                  60

Pro Gln Gly Gly Gly Pro Trp Asp Ser Val Ala Arg Val Leu Pro Asn
 65                  70                  75                  80

Gly Ser Leu Phe Leu Pro Ala Val Gly Ile Gln Asp Glu Gly Ile Phe
                 85                  90                  95

Arg Cys Gln Ala Met Asn Arg Asn Gly Lys Glu Thr Lys Ser Asn Tyr
                100                 105                 110

Arg Val Arg Val Tyr Gln Ile Pro Gly Lys Pro Glu Ile Val Asp Ser
                115                 120                 125

Ala Ser Glu Leu Thr Ala Gly Val Pro Asn Lys Val Gly Thr Cys Val
                130                 135                 140

Ser Glu Gly Ser Tyr Pro Ala Gly Thr Leu Ser Trp His Leu Asp Gly
145                 150                 155                 160

Lys Pro Leu Val Pro Asn Glu Lys Gly Val Ser Val Lys Glu Gln Thr
                165                 170                 175

Arg Arg His Pro Glu Thr Gly Leu Phe Thr Leu Gln Ser Glu Leu Met
                180                 185                 190

Val Thr Pro Ala Arg Gly Gly Asp Pro Arg Pro Thr Phe Ser Cys Ser
                195                 200                 205

Phe Ser Pro Gly Leu Pro Arg His Arg Ala Leu Arg Thr Ala Pro Ile
                210                 215                 220

Gln Pro Arg Val Trp Glu Pro Val Pro Leu Glu Glu Val Gln Leu Val
225                 230                 235                 240

Val Glu Pro Glu Gly Gly Ala Val Ala Pro Gly Gly Thr Val Thr Leu
                245                 250                 255

Thr Cys Glu Val Pro Ala Gln Pro Ser Pro Gln Ile His Trp Met Lys
                260                 265                 270

Asp Gly Val Pro Leu Pro Leu Pro Pro Ser Pro Val Leu Ile Leu Pro
                275                 280                 285

Glu Ile Gly Pro Gln Asp Gln Gly Thr Tyr Ser Cys Val Ala Thr His
                290                 295                 300

Ser Ser His Gly Pro Gln Glu Ser Arg Ala Val Ser Ile Ser Ile Ile
305                 310                 315                 320

Glu Pro Gly Glu Glu Gly Pro Thr Ala Gly Ser Val Gly Gly Ser Gly
                325                 330                 335

Leu Gly Thr His His His His His His
                340                 345

<210> SEQ ID NO 35
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Gly Ser Ser His His His His His His Ser Ser Gly Leu Val Pro
 1               5                  10                  15

Arg Gly Ser His Met Gln Asn Ile Thr Ala Arg Ile Gly Glu Pro Leu
                 20                  25                  30

Val Leu Lys Cys Lys Gly Ala Pro Lys Lys Pro Pro Gln Arg Leu Glu
                 35                  40                  45

Trp Lys Leu Asn Thr Gly Arg Thr Glu Ala Trp Lys Val Leu Ser Pro
```

```
                50                  55                  60
Gln Gly Gly Gly Pro Trp Asp Ser Val Ala Arg Val Leu Pro Asn Gly
 65                  70                  75                  80

Ser Leu Phe Leu Pro Ala Val Gly Ile Gln Asp Glu Gly Ile Phe Arg
                 85                  90                  95

Cys Gln Ala Met Asn Arg Asn Gly Lys Glu Thr Lys Ser Asn Tyr Arg
                100                 105                 110

Val Arg Val Tyr Gln Ile Pro Gly Lys Pro Glu Ile Val Asp Ser
            115                 120                 125

<210> SEQ ID NO 36
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Gly Ser Ser His His His His His His Ser Ser Gly Leu Val Pro
 1               5                  10                  15

Arg Gly Ser His Met Gln Asn Ile Thr Ala Arg Ile Gly Glu Pro Leu
                 20                  25                  30

Val Leu Lys Cys Lys Gly Ala Pro Lys Lys Pro Pro Gln Arg Leu Glu
             35                  40                  45

Trp Lys Leu Asn Thr Gly Arg Thr Glu Ala Trp Lys Val Leu Ser Pro
 50                  55                  60

Gln Gly Gly Gly Pro Trp Asp Ser Val Ala Arg Val Leu Pro Asn Gly
 65                  70                  75                  80

Ser Leu Phe Leu Pro Ala Val Gly Ile Gln Asp Glu Gly Ile Phe Arg
                 85                  90                  95

Cys Gln Ala Met Asn Arg Asn Gly Lys Glu Thr Lys Ser Asn Tyr Arg
                100                 105                 110

Val Arg Val Tyr Gln Ile Pro Gly Lys Pro Glu Ile Val Asp Ser Ala
            115                 120                 125

Ser Glu Leu Thr Ala Gly Val Pro Asn Lys Val Gly Thr Cys Val Ser
    130                 135                 140

Glu Gly Ser Tyr Pro Ala Gly Thr Leu Ser Trp His Leu Asp Gly Lys
145                 150                 155                 160

Pro Leu Val Pro Asn Glu Lys Gly Val Ser Val Lys Glu Gln Thr Arg
                165                 170                 175

Arg His Pro Glu Thr Gly Leu Phe Thr Leu Gln Ser Glu Leu Met Val
                180                 185                 190

Thr Pro Ala Arg Gly Gly Asp Pro Arg Pro Thr Phe Ser Cys Ser Phe
            195                 200                 205

Ser Pro Gly Leu Pro Arg His Arg Ala Leu Arg Thr Ala Pro Ile Gln
    210                 215                 220

Pro Arg Val Trp Glu Pro Val Pro
225                 230

<210> SEQ ID NO 37
<211> LENGTH: 334
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37
```

```
Met Gly Ser Ser His His His His His Ser Ser Gly Leu Val Pro
1               5                   10                  15

Arg Gly Ser His Met Gln Asn Ile Thr Ala Arg Ile Gly Glu Pro Leu
            20                  25                  30

Val Leu Lys Cys Lys Gly Ala Pro Lys Pro Pro Gln Arg Leu Glu
        35                  40                  45

Trp Lys Leu Asn Thr Gly Arg Thr Glu Ala Trp Lys Val Leu Ser Pro
50                  55                      60

Gln Gly Gly Gly Pro Trp Asp Ser Val Ala Arg Val Leu Pro Asn Gly
65              70                  75                  80

Ser Leu Phe Leu Pro Ala Val Gly Ile Gln Asp Glu Gly Ile Phe Arg
            85                  90                  95

Cys Gln Ala Met Asn Arg Asn Gly Lys Glu Thr Lys Ser Asn Tyr Arg
            100                 105                 110

Val Arg Val Tyr Gln Ile Pro Gly Lys Pro Glu Ile Val Asp Ser Ala
        115                 120                 125

Ser Glu Leu Thr Ala Gly Val Pro Asn Lys Val Gly Thr Cys Val Ser
130                 135                 140

Glu Gly Ser Tyr Pro Ala Gly Thr Leu Ser Trp His Leu Asp Gly Lys
145                 150                 155                 160

Pro Leu Val Pro Asn Glu Lys Gly Val Ser Val Lys Glu Gln Thr Arg
                165                 170                 175

Arg His Pro Glu Thr Gly Leu Phe Thr Leu Gln Ser Glu Leu Met Val
            180                 185                 190

Thr Pro Ala Arg Gly Gly Asp Pro Arg Pro Thr Phe Ser Cys Ser Phe
        195                 200                 205

Ser Pro Gly Leu Pro Arg His Arg Ala Leu Arg Thr Ala Pro Ile Gln
210                 215                 220

Pro Arg Val Trp Glu Pro Val Pro Leu Glu Glu Val Gln Leu Val Val
225                 230                 235                 240

Glu Pro Glu Gly Gly Ala Val Ala Pro Gly Gly Thr Val Thr Leu Thr
                245                 250                 255

Cys Glu Val Pro Ala Gln Pro Ser Pro Gln Ile His Trp Met Lys Asp
            260                 265                 270

Gly Val Pro Leu Pro Leu Pro Pro Ser Pro Val Leu Ile Leu Pro Glu
        275                 280                 285

Ile Gly Pro Gln Asp Gln Gly Thr Tyr Ser Cys Val Ala Thr His Ser
290                 295                 300

Ser His Gly Pro Gln Glu Ser Arg Ala Val Ser Ile Ser Ile Ile Glu
305                 310                 315                 320

Pro Gly Glu Glu Gly Pro Thr Ala Gly Ser Val Gly Gly Ser
                325                 330

<210> SEQ ID NO 38
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Gly Ser Ser His His His His His Ser Ser Gly Leu Val Pro
1               5                   10                  15

Arg Gly Ser His Met Ala Ser Glu Leu Thr Ala Gly Val Pro Asn Lys
            20                  25                  30
```

```
Val Gly Thr Cys Val Ser Glu Gly Ser Tyr Pro Ala Gly Thr Leu Ser
         35                  40                  45

Trp His Leu Asp Gly Lys Pro Leu Val Pro Asn Glu Lys Gly Val Ser
 50                  55                  60

Val Lys Glu Gln Thr Arg Arg His Pro Glu Thr Gly Leu Phe Thr Leu
 65                  70                  75                  80

Gln Ser Glu Leu Met Val Thr Pro Ala Arg Gly Gly Asp Pro Arg Pro
                 85                  90                  95

Thr Phe Ser Cys Ser Phe Ser Pro Gly Leu Pro Arg His Arg Ala Leu
                100                 105                 110

Arg Thr Ala Pro Ile Gln Pro Arg Val Trp Glu Pro Val Pro
                115                 120                 125

<210> SEQ ID NO 39
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Gly Ser Ser His His His His His His Ser Ser Gly Leu Val Pro
 1               5                  10                  15

Arg Gly Ser His Met Ala Ser Glu Leu Thr Ala Gly Val Pro Asn Lys
                 20                  25                  30

Val Gly Thr Cys Val Ser Glu Gly Ser Tyr Pro Ala Gly Thr Leu Ser
         35                  40                  45

Trp His Leu Asp Gly Lys Pro Leu Val Pro Asn Glu Lys Gly Val Ser
 50                  55                  60

Val Lys Glu Gln Thr Arg Arg His Pro Glu Thr Gly Leu Phe Thr Leu
 65                  70                  75                  80

Gln Ser Glu Leu Met Val Thr Pro Ala Arg Gly Gly Asp Pro Arg Pro
                 85                  90                  95

Thr Phe Ser Cys Ser Phe Ser Pro Gly Leu Pro Arg His Arg Ala Leu
                100                 105                 110

Arg Thr Ala Pro Ile Gln Pro Arg Val Trp Glu Pro Val Pro Leu Glu
                115                 120                 125

Glu Val Gln Leu Val Val Glu Pro Glu Gly Gly Ala Val Ala Pro Gly
 130                 135                 140

Gly Thr Val Thr Leu Thr Cys Glu Val Pro Ala Gln Pro Ser Pro Gln
145                 150                 155                 160

Ile His Trp Met Lys Asp Gly Val Pro Leu Pro Leu Pro Pro Ser Pro
                165                 170                 175

Val Leu Ile Leu Pro Glu Ile Gly Pro Gln Asp Gln Gly Thr Tyr Ser
                180                 185                 190

Cys Val Ala Thr His Ser Ser His Gly Pro Gln Glu Ser Arg Ala Val
                195                 200                 205

Ser Ile Ser Ile Ile Glu Pro Gly Glu Glu Gly Pro Thr Ala Gly Ser
         210                 215                 220

Val Gly Gly Ser
225

<210> SEQ ID NO 40
<211> LENGTH: 123
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 40

Met Gly Ser Ser His His His His His Ser Ser Gly Leu Val Pro
1               5                   10                  15

Arg Gly Ser His Met Leu Glu Glu Val Gln Leu Val Val Glu Pro Glu
            20                  25                  30

Gly Gly Ala Val Ala Pro Gly Gly Thr Val Thr Leu Thr Cys Glu Val
        35                  40                  45

Pro Ala Gln Pro Ser Pro Gln Ile His Trp Met Lys Asp Gly Val Pro
    50                  55                  60

Leu Pro Leu Pro Pro Ser Pro Val Leu Ile Leu Pro Glu Ile Gly Pro
65                  70                  75                  80

Gln Asp Gln Gly Thr Tyr Ser Cys Val Ala Thr His Ser Ser His Gly
                85                  90                  95

Pro Gln Glu Ser Arg Ala Val Ser Ile Ser Ile Glu Pro Gly Glu
            100                 105                 110

Glu Gly Pro Thr Ala Gly Ser Val Gly Gly Ser
        115                 120

<210> SEQ ID NO 41
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

-continued

```
Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 42
<211> LENGTH: 326
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255
```

```
Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Val Arg Gln Ala Pro Gly Gln Gly Leu Glu Trp Met Gly
1               5                   10

<210> SEQ ID NO 45
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Arg Phe Val Phe Ser Leu Asp Thr Ser Val Ser Thr Ala Tyr Leu Gln
1               5                   10                  15

Ile Cys Ser Leu Lys Ala Glu Asp Thr Ala Val Tyr Tyr Cys Ala Arg
            20                  25                  30

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Gly Gln Gly Thr Thr Val Thr Val Ser Ser
1               5                   10

<210> SEQ ID NO 47
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 49
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Tyr Gln Gln Lys Pro Gly Lys Ala Pro Lys Leu Leu Ile Tyr
1               5                   10                  15

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

-continued

```
<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Phe Gly Gln Gly Thr Lys Leu Glu Ile Lys Arg
1               5                   10

<210> SEQ ID NO 53
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Ile Val Met Thr Gln Ser Pro Ala Thr Leu Ser Leu Ser Pro Gly
1               5                   10                  15

Glu Arg Ala Thr Leu Ser Cys
            20

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Trp Tyr Gln Gln Lys Pro Gly Gln Ala Pro Arg Leu Leu Ile Tyr
1               5                   10                  15

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Ile Pro Ala Arg Phe Ser Gly Ser Gly Ser Gly Thr Asp Phe Thr
1               5                   10                  15

Leu Thr Ile Ser Ser Leu Gln Ser Glu Asp Phe Ala Val Tyr Tyr Cys
            20                  25                  30

<210> SEQ ID NO 56
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Gly Met Asn Trp Val Arg Gln Ala Pro Gly Gln Gly Leu Glu Trp Met
        35                  40                  45
```

Gly Tyr Ile Asn Thr Asn Thr Gly Glu Ser Ile Tyr Ser Glu Glu Phe
            50                  55                  60

Lys Gly Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
                 85                  90                  95

Ala Arg Ser Arg Met Val Thr Ala Tyr Gly Met Asp Tyr Trp Gly Gln
                100                 105                 110

Gly Thr Thr Val Thr Val Ser Ser
            115                 120

<210> SEQ ID NO 57
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Phe
                20                  25                  30

Gly Met Asn Trp Val Arg Gln Ala Pro Gly Gln Gly Leu Glu Trp Met
             35                  40                  45

Gly Tyr Ile Asn Thr Asn Thr Gly Glu Ser Ile Tyr Ser Glu Glu Phe
            50                  55                  60

Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Arg Met Val Thr Ala Tyr Gly Met Asp Tyr Trp Gly Gln
                100                 105                 110

Gly Thr Thr Val Thr Val Ser Ser
            115                 120

<210> SEQ ID NO 58
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Val Ser Ala Ser Val Gly
 1               5                  10                  15

Asp Arg Val Thr Ile Thr Cys Lys Ala Ser Gln Asn Val Gly Thr Ala
                20                  25                  30

Val Ala Trp Tyr Gln Gln Lys Pro Gly Lys Ala Pro Lys Leu Leu Ile
             35                  40                  45

Tyr Ser Ala Ser Asn Arg Tyr Thr Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Ser Tyr Pro Leu
                 85                  90                  95

Thr Phe Gly Gln Gly Thr Lys Leu Glu Ile Lys Arg
            100                 105

<210> SEQ ID NO 59
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Thr Ala
            20                  25                  30

Val Ala Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Ser Tyr Pro Leu
                85                  90                  95

Thr Phe Gly Gln Gly Thr Lys Leu Glu Ile Lys Arg
            100                 105

<210> SEQ ID NO 60
<211> LENGTH: 404
<212> TYPE: PRT
<213> ORGANISM: Homo sapiens

<400> SEQUENCE: 60

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys

```
              195                 200                 205
Ser Phe Ser Pro Gly Leu Pro Arg His Arg Ala Leu Arg Thr Ala Pro
            210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
            275                 280                 285

Pro Glu Ile Gly Pro Gln Asp Gln Gly Thr Tyr Ser Cys Val Ala Thr
290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Ser Val Gly Gly Ser
                325                 330                 335

Gly Leu Gly Thr Leu Ala Leu Ala Leu Gly Ile Leu Gly Gly Leu Gly
            340                 345                 350

Thr Ala Ala Leu Leu Ile Gly Val Ile Leu Trp Gln Arg Arg Gln Arg
            355                 360                 365

Arg Gly Glu Glu Arg Lys Ala Pro Glu Asn Gln Glu Glu Glu Glu Glu
    370                 375                 380

Arg Ala Glu Leu Asn Gln Ser Glu Glu Pro Glu Ala Gly Glu Ser Ser
385                 390                 395                 400

Thr Gly Gly Pro

<210> SEQ ID NO 61
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160
```

```
Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
                260                 265                 270

Lys Asp Gly Val Pro Leu Pro Leu Pro Pro Ser Pro Val Leu Ile Leu
            275                 280                 285

Pro Glu Ile Gly Pro Gln Asp Gln Gly Thr Tyr Ser Cys Val Ala Thr
        290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly
                325                 330
```

<210> SEQ ID NO 62
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Gly Met Asn Trp Val Arg Gln Ala Pro Gly Gln Gly Leu Glu Trp Met
        35                  40                  45

Gly Tyr Ile Asn Thr Asn Thr Gly Glu Ser Ile Tyr Ser Glu Glu Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Ser Arg Met Val Thr Ala Tyr Gly Met Asp Tyr Trp Gly Gln
            100                 105                 110

Gly Thr Thr Val Thr Val Ser Ser
        115                 120
```

<210> SEQ ID NO 63
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

-continued

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Leu Glu Ile Lys Arg
            100                 105

<210> SEQ ID NO 64
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ser Pro Lys Leu Leu Ile
        35                  40                  45

Phe Ser Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Leu
                85                  90                  95

Thr Phe Gly Gln Gly Thr Lys Leu Glu Ile Lys Arg
            100                 105

<210> SEQ ID NO 65
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Ile Val Met Thr Gln Ser Pro Ala Thr Leu Ser Leu Ser Pro Gly
1               5                   10                  15

Glu Arg Ala Thr Leu Ser Cys Lys Ala Ser Gln Asn Val Gly Thr Ala
            20                  25                  30

Val Ala Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Ser Ser Tyr Pro Leu

```
                85                  90                  95
Thr Phe Gly Gln Gly Thr Lys Leu Glu Ile Lys Arg
                100                 105

<210> SEQ ID NO 66
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Ile Val Met Thr Gln Ser Pro Ala Thr Leu Ser Leu Ser Pro Gly
1               5                   10                  15

Glu Arg Ala Thr Leu Ser Cys Lys Ala Ser Gln Asn Val Gly Thr Ala
            20                  25                  30

Val Ala Trp Tyr Gln Gln Lys Pro Gly Gln Ser Pro Arg Leu Leu Ile
        35                  40                  45

Phe Ser Ala Ser Asn Arg Tyr Thr Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Phe Cys Gln Gln Tyr Ser Ser Tyr Pro Leu
                85                  90                  95

Thr Phe Gly Gln Gly Thr Lys Leu Glu Ile Lys Arg
                100                 105

<210> SEQ ID NO 67
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Gly Met Asn Trp Val Arg Gln Ala Pro Gly Gln Gly Leu Glu Trp Met
        35                  40                  45

Gly Tyr Ile Asn Thr Asn Thr Gly Glu Ser Ile Tyr Ser Glu Glu Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Phe Cys
                85                  90                  95

Ala Arg Ser Arg Met Val Thr Ala Tyr Gly Met Asp Tyr Trp Gly Gln
                100                 105                 110

Gly Thr Val Thr Val Ser Ser
            115                 120

<210> SEQ ID NO 68
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 68

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Gly Met Asn Trp Val Arg Gln Ala Pro Gly Gln Gly Leu Glu Trp Met
        35                  40                  45

Gly Tyr Ile Asn Thr Asn Thr Gly Glu Ser Ile Tyr Ser Glu Glu Phe
    50                  55                  60

Lys Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Met Val Thr Ala Tyr Gly Met Asp Tyr Trp Gly Gln
            100                 105                 110

Gly Thr Ser Val Thr Val Ser Ser
        115                 120

<210> SEQ ID NO 69
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Gly Met Asn Trp Val Arg Gln Ala Pro Gly Gln Gly Leu Glu Trp Met
        35                  40                  45

Gly Tyr Ile Asn Thr Asn Thr Gly Glu Ser Ile Tyr Ser Glu Glu Phe
    50                  55                  60

Lys Gly Arg Phe Thr Phe Thr Leu Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ser Arg Met Val Thr Ala Tyr Gly Met Asp Tyr Trp Gly Gln
            100                 105                 110

Gly Thr Ser Val Thr Val Ser Ser
        115                 120

<210> SEQ ID NO 70
<211> LENGTH: 31
<212> TYPE: PRT
<213> ORGANISM: Homo sapiens

<400> SEQUENCE: 70

Gln Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn
            20                  25                  30

<210> SEQ ID NO 71
<211> LENGTH: 30
<212> TYPE: PRT

```
<213> ORGANISM: Homo sapiens

<400> SEQUENCE: 71

Lys Leu Asn Thr Gly Arg Thr Glu Ala Trp Lys Val Leu Ser Pro Gln
1               5                   10                  15

Gly Gly Gly Pro Trp Asp Ser Val Ala Arg Val Leu Pro Asn
            20                  25                  30

<210> SEQ ID NO 72
<211> LENGTH: 30
<212> TYPE: PRT
<213> ORGANISM: Homo sapiens

<400> SEQUENCE: 72

Leu Pro Asn Gly Ser Leu Phe Leu Pro Ala Val Gly Ile Gln Asp Glu
1               5                   10                  15

Gly Ile Phe Arg Cys Gln Ala Met Asn Arg Asn Gly Lys Glu
            20                  25                  30

<210> SEQ ID NO 73
<211> LENGTH: 30
<212> TYPE: PRT
<213> ORGANISM: Homo sapiens

<400> SEQUENCE: 73

Gly Lys Glu Thr Lys Ser Asn Tyr Arg Val Arg Val Tyr Gln Ile Pro
1               5                   10                  15

Gly Lys Pro Glu Ile Val Asp Ser Ala Ser Glu Leu Thr Ala
            20                  25                  30

<210> SEQ ID NO 74
<211> LENGTH: 30
<212> TYPE: PRT
<213> ORGANISM: Homo sapiens

<400> SEQUENCE: 74

Leu Thr Ala Gly Val Pro Asn Lys Val Gly Thr Cys Val Ser Glu Gly
1               5                   10                  15

Ser Tyr Pro Ala Gly Thr Leu Ser Trp Lys Leu Asp Gly Lys
            20                  25                  30

<210> SEQ ID NO 75
<211> LENGTH: 30
<212> TYPE: PRT
<213> ORGANISM: Homo sapiens

<400> SEQUENCE: 75

Asp Gly Lys Pro Leu Val Pro Asn Glu Lys Gly Val Ser Val Lys Glu
1               5                   10                  15

Gln Thr Arg Arg His Pro Glu Thr Gly Leu Phe Thr Leu Gln
            20                  25                  30

<210> SEQ ID NO 76
<211> LENGTH: 30
<212> TYPE: PRT
<213> ORGANISM: Homo sapiens

<400> SEQUENCE: 76

Thr Leu Gln Ser Glu Leu Met Val Thr Pro Ala Arg Gly Gly Asp Pro
1               5                   10                  15

Arg Pro Thr Phe Ser Cys Ser Phe Ser Pro Gly Leu Pro Arg
            20                  25                  30
```

<210> SEQ ID NO 77
<211> LENGTH: 30
<212> TYPE: PRT
<213> ORGANISM: Homo sapiens

<400> SEQUENCE: 77

Leu Pro Arg His Arg Ala Leu Arg Thr Ala Pro Ile Gln Pro Arg Val
1               5                   10                  15
Trp Glu Pro Val Pro Leu Glu Glu Val Gln Leu Val Val Glu
            20                  25                  30

<210> SEQ ID NO 78
<211> LENGTH: 30
<212> TYPE: PRT
<213> ORGANISM: Homo sapiens

<400> SEQUENCE: 78

Val Val Glu Pro Glu Gly Gly Ala Val Ala Pro Gly Gly Thr Val Thr
1               5                   10                  15
Leu Thr Cys Glu Val Pro Ala Gln Pro Ser Pro Gln Ile His
            20                  25                  30

<210> SEQ ID NO 79
<211> LENGTH: 30
<212> TYPE: PRT
<213> ORGANISM: Homo sapiens

<400> SEQUENCE: 79

Gln Ile His Trp Met Lys Asp Gly Val Pro Leu Pro Leu Pro Pro Ser
1               5                   10                  15
Pro Val Leu Ile Leu Pro Glu Ile Gly Pro Gln Asp Gln Gly
            20                  25                  30

<210> SEQ ID NO 80
<211> LENGTH: 30
<212> TYPE: PRT
<213> ORGANISM: Homo sapiens

<400> SEQUENCE: 80

Asp Gln Gly Thr Tyr Ser Cys Val Ala Thr His Ser Ser His Gly Pro
1               5                   10                  15
Gln Glu Ser Arg Ala Val Ser Ile Ser Ile Ile Glu Pro Gly
            20                  25                  30

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ccgaattccg gaagcaggat ggcagccg                                           28

<210> SEQ ID NO 82
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82

-continued ccctcgagcc cctcaaggcc ctcagtacta ct                32

<210> SEQ ID NO 83
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
agtaacggcc gccagtgtgc tggaattcgg a                 31

<210> SEQ ID NO 84
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ccggtaccac ctgcagttgg cccctcctcg cc                32

<210> SEQ ID NO 85
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cgaagcttga tgaacaggaa tggaaaggag accaag            36

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tcctcgagca cctgcagttg gcccctcctc gcct              34

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gcaccatggc agccggaaca gcagttg                      27

<210> SEQ ID NO 88
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gagtctcgag gcagaatcta caatttctg                    29

```
<210> SEQ ID NO 89
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
atgctacata tgaaaaagac agctatcgcg attgcagtgg cactggctgg tttcgctacc      60
gtagcgcagg ccgctcaaaa catcacagcc                                      90

<210> SEQ ID NO 90
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
atgctactcg agtcagtggt ggtggtggtg gtgagttccc agccctgatc ctcccacaga      60
gcctgcagtt ggcccctcc                                                  79

<210> SEQ ID NO 91
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gtacgatatc gagggacgaa tggatccacc gtgcccagca cc                         42

<210> SEQ ID NO 92
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ctagtctaga tcatttaccc ggagacaggg ag                                    32

<210> SEQ ID NO 93
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gtacgatatc gagggacgaa tggatccacc gtgcccagca cc                         42

<210> SEQ ID NO 94
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
```

```
ctagtctaga tcatttaccc ggagacaggg ag                                    32

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 95

His His His His His His
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

His His His His His His Thr
1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Gly Gly Ser
1               5
```